United States Patent
Machida et al.

(10) Patent No.: US 8,617,078 B2
(45) Date of Patent: Dec. 31, 2013

(54) ULTRASONIC TRANSDUCER AND ULTRASONIC DIAGNOSTIC DEVICE USING SAME

(75) Inventors: Shuntaro Machida, Kokubunji (JP); Taiichi Takezaki, Tachikawa (JP); Toshiyuki Mine, Fussa (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 13/577,816

(22) PCT Filed: Jan. 25, 2011

(86) PCT No.: PCT/JP2011/051344
§ 371 (c)(1),
(2), (4) Date: Aug. 8, 2012

(87) PCT Pub. No.: WO2011/111427
PCT Pub. Date: Sep. 15, 2011

(65) Prior Publication Data
US 2012/0316445 A1    Dec. 13, 2012

(30) Foreign Application Priority Data
Mar. 12, 2010  (JP) .............................. 2010-055270

(51) Int. Cl.
A61B 8/00 (2006.01)
(52) U.S. Cl.
USPC .......................................... 600/459; 310/311
(58) Field of Classification Search
USPC .......................................... 600/459; 310/311
See application file for complete search history.

(56) References Cited

U.S. PATENT DOCUMENTS

| 6,320,239 | B1 | 11/2001 | Eccardt et al. | |
|---|---|---|---|---|
| 7,512,038 | B2 * | 3/2009 | Machida et al. | 367/181 |
| 2005/0200241 | A1 | 9/2005 | Degertekin | |
| 2007/0299345 | A1 | 12/2007 | Adachi et al. | |
| 2008/0283945 | A1 | 11/2008 | Kobayashi et al. | |

FOREIGN PATENT DOCUMENTS

| JP | 2006-122188 | 5/2006 |
|---|---|---|
| JP | 2007-527285 | 9/2007 |
| JP | 2008/288813 | 11/2008 |
| JP | 2009-100460 | 5/2009 |
| JP | 2009-272824 | 11/2009 |
| WO | WO 2009/016606 A2 | 2/2009 |
| WO | WO 2009/041675 A1 | 4/2009 |

* cited by examiner

Primary Examiner — Jonathan Cwern
(74) Attorney, Agent, or Firm — Antonelli, Terry, Stout & Kraus, LLP.

(57) ABSTRACT

In an ultrasonic transducer comprising a first electrode, a first insulating film disposed on the first electrode, a hollow part provided above the first insulating film and disposed between surfaces above and below the hollow part, a second insulating film disposed above the hollow part, and a second electrode disposed on the second insulating film, a first conductive film disposed on a side of the surface below the hollow part and a second conductive film disposed on a side of the surface above the hollow part are provided, the first conductive film and the second conductive film are disposed so that they overlap with a region in which the surfaces above and below the hollow part contact with each other as seen from above when the transducer is driven, and they do not overlap with each other in the region as seen from above.

19 Claims, 45 Drawing Sheets

(a)

(b)

(a)

(b)

(a)

(b)

(a)

(b)

(a)

(b)

(a)

A ↓    A' ↓

200   2211   203  202  201

(b)

B ↓    B' ↓

200   203  202  201

(a)

(b)

(a)

(b)

(a)

(b)

(a)

(b)

(a)

(b)

(a)

(b)

(a)

(b)

(a)

(b)

US 8,617,078 B2

ULTRASONIC TRANSDUCER AND ULTRASONIC DIAGNOSTIC DEVICE USING SAME

TECHNICAL FIELD

The present invention relates to an ultrasonic transducer and an ultrasonic diagnostic device using the same. In particular, the present invention relates to an ultrasonic transducer produced by the micro electro mechanical system (MEMS) technology, and an ultrasonic diagnostic device using the same.

BACKGROUND ART

Ultrasonic transducers transmit and receive ultrasonic waves, and thus they are used for diagnosis of tumors etc. in human bodies, nondestructive tests of structures, and so forth. As the ultrasonic transducers, those utilizing vibration of piezoelectric substances have so far been used. However, with progress of the MEMS technology in recent years, capacitive micromachined ultrasonic transducers (CMUTs) comprising a vibration part formed on a silicon substrate have been actively developed aiming at practical use thereof. For example, U.S. Pat. No. 6,320,239 B1 (Patent document 1) discloses a single CMUT and a CMUT array.

In contrast to the conventional transducers utilizing piezoelectric substances, CMUTs have advantages of the wide frequency band of usable ultrasonic waves, high sensitivity, and so forth. Moreover, since they are produced by using LSI processing techniques, micro processing can be used. In particular, CMUTs is considered to be indispensable when ultrasonic devices are arranged in an array and independently controlled. This is because, while wiring for each device is needed and thus the number of the wiring in the array becomes a huge number, CMUTs are produced by using LSI processing techniques, and therefore the wiring is easy. Moreover, that is also because the CMUTS can be embedded on one chip of a circuit which processes signals from the ultrasonic transmission and reception part.

With reference to FIG. 1, fundamental structure and operation of CMUT will be explained below. Above a lower electrode 101, a hollow part 102 surrounded by an insulating film 103 is provided. Above the hollow part 102, an upper electrode 104 is disposed through the insulating film 103. If a direct voltage and an alternate voltage are superimposingly applied between the upper electrode 104 and the lower electrode 101, an electrostatic force is generated between the upper electrode 104 and the lower electrode 101, and a membrane 105 constituted by the insulating film 103 and the upper electrodes 104 above the hollow part 102 vibrates at the frequency of the applied alternate voltage to emit ultrasonic waves. Conversely, in the case of reception, the membrane 105 is vibrated by pressure of ultrasonic waves that arrive at the surface of the membrane 105. Then, the distance between the upper electrode 104 and the lower electrode 101 varies, and therefore ultrasonic waves can be detected as change of electrostatic capacitance. According to the aforementioned principle of operation, by applying a direct voltage between the upper electrode 104 and the lower electrode 101, an electrostatic force is generated between both the electrodes, and the membrane is deformed and stabilized at a deformation amount at which the spring restoring forth induced by the deformation and the electrostatic force are balanced.

CMUT is usually driven at such a direct voltage that the electrostatic force between the electrodes and the spring restoring forth are balanced. However, if a direct voltage larger than such a voltage that deformation amount of the membrane reaches about ⅓ of the distance between the electrodes, called collapse voltage, is applied, the electrostatic force between the electrodes becomes larger than the spring restoring force of the membrane, thus the membrane cannot be stabilized at a fixed position, and the surface 106 above the hollow part contacts with the surface 107 below the hollow part. If they contact with each other, there is produced a structure that the insulating film 103 is held between the upper electrode and the lower electrode without the hollow part. As a result, electric field intensity in the insulating film becomes large in the contacting region, and electrical charge is injected into the insulating film from the electrodes to generate fixed electrical charge in the insulating film. After the direct voltage is shut off, if a direct voltage is applied again between the two electrodes, the electric field between the electrodes is shielded by the fixed electrical charge in the insulating film, and the voltage used for optimal operation of CMUT fluctuates. Moreover, it is also possible that the insulating property of the insulating film may be degraded depending on the injection rate of electrical charge into the insulating film, and thereby the upper electrode and the lower electrode may be short-circuited. Therefore, the CMUT disclosed in Patent document 1 is usually used with a voltage significantly lower than the collapse voltage in order to prevent the surface above the hollow part from contacting with the surface below the hollow part.

Japanese Patent Unexamined Publication (KOKAI) No. 2009-272824 (Patent document 2) discloses a structure in which a floating electrode is embedded in an insulating film between electrodes in order to reduce the direct voltage for driving CMUT or make continuous application thereof unnecessary.

PRIOR ART REFERENCES

Patent Documents

Patent document 1: U.S. Pat. No. 6,320,239 B1
Patent document 2: Japanese Patent Unexamined Publication (KOKAI) No. 2009-272824

SUMMARY OF THE INVENTION

Object to be Achieved by the Invention

In order to improve reception sensitivity for ultrasonic waves, it is generally necessary to make the distance between the electrodes as short as possible at the time of use of CMUT, and therefore it is important to apply a voltage as close to the collapse voltage as possible between the electrodes. Moreover, in order to improve transmission sound pressure of the ultrasonic waves, it is desirable to maximize the vibration amplitude of the membrane 105. However, in order to prevent the surface 106 above the hollow part from contacting with the surface 107 below the hollow part during the vibration, which results in injection of electrical charge into the insulating film, the alternate voltage to be superimposed on the direct voltage must also be a voltage significantly lower than the voltage at which the surface 106 above the hollow part contacts with the surface 107 below the hollow part.

Patent document 2 discloses a structure that a floating electrode is embedded in an insulating film between upper and lower electrodes. This structure is configured so that CMUT is driven by a potential difference between the floating electrode having electrical charge accumulated beforehand and the upper electrode or lower electrode. However, in order to prevent dissipation of the electrical charge accumulated in the floating electrode, it is necessary to cover circumference of the floating electrode with an insulating film, that is, embed the floating electrode in an insulating film. Further, since electrical charge is accumulated in the floating electrode beforehand, when the surfaces above and below the hollow part contact with each other, accumulation of electrical charge in the insulating film between the floating electrode and the upper electrode or lower electrode and reduction of the insulation withstand voltage of the insulating film are unavoidable.

As described above, because of the problems caused by the contact of the surfaces above and below the hollow part, it is difficult to use a larger direct current voltage or alternate current voltage, i.e., improve reception sensitivity or transmission sound pressure, in the conventional transducers according to the conventional techniques.

Means for Achieving the Object

Brief explanations of the outlines of the representative embodiments of the present invention disclosed in this application are as follows.

The present invention relates to an ultrasonic transducer comprising a first electrode, a first insulating film disposed on the first electrode, a hollow part provided above the first insulating film, a second insulating film disposed above the hollow part, a second electrode disposed on the second insulating film, and an electrically isolated conductive film disposed between the first electrode and the second electrode, wherein the conductive film is disposed at such a position that, as seen from above, the conductive film overlaps with a region in which surfaces above and below the hollow part contact with each other when the transducer is driven, and the conductive film is exposed to the hollow part.

Another embodiment of the present invention is an ultrasonic transducer comprising a first electrode, a first insulating film disposed on the first electrode, a hollow part provided above the first insulating film, a second insulating film disposed above the hollow part, a second electrode disposed on the second insulating film, a conductive film disposed between the first electrode and the second electrode at such a position that, as seen from above, the conductive film overlaps with a region in which surfaces above and below the hollow part contact with each other when the transducer is driven, and a switch connected to the conductive film for controlling ON/OFF of connection of the conductive film to the ground potential.

Still another embodiment of the present invention is an ultrasonic transducer comprising a first electrode, a first insulating film disposed on the first electrode, an electrically isolated first conductive film disposed on the first insulating film, a hollow part provided above the first conductive film, an electrically isolated second conductive film disposed above the hollow part, a second insulating film disposed on the second conductive film, and a second electrode disposed on the second insulating film, wherein the first conductive film and the second conductive film are disposed in a region in which surfaces above and below the hollow part contact with each other when the transducer is driven, and the first conductive film and the second conductive film do not overlap with each other in that region as seen from above.

As another aspect, the present invention provides an ultrasonic diagnostic device provided with an ultrasonic probe comprising any of the aforementioned ultrasonic transducers, and a control part for controlling the ultrasonic probe.

Effect of the Invention

The present invention provides a structure of CMUT for suppressing accumulation of electrical charge in an insulating film between upper and lower electrodes and reduction of insulation withstand voltage thereof even when surfaces above and below the hollow part contact with each other, and an ultrasonic diagnostic device using it. The present invention also provides a CMUT that can improve reception sensitivity and transmission sound pressure compared with those of conventional CMUTs while securing reliability, and an ultrasonic diagnostic device using it.

MODES FOR CARRYING OUT THE INVENTION

Hereafter, embodiments of the present invention will be explained in detail with reference to the drawings. In all the drawings for explaining the embodiments, the same members are basically indicated with the same numerals, and repetitive explanations for them are omitted.

In the following explanations of the embodiments, explanations are made with several sections or several examples for convenience as required, but they are mutually related, and are in such a relation that one of them is modification, details, supplemental explanation or the like of a part or all of the other, unless especially indicated. Moreover, in the following explanations of the embodiments, when a number of an element or the like (including number, numerical value, quantity, range etc.) is mentioned, the numeral is not limited to that specific number, and may be larger or smaller than the mentioned number, except for the case where it is explicitly indicated that the number should be the specifically mentioned number, or it is theoretically clear that the number should be limited to the specifically mentioned number. Furthermore, in the embodiments mentioned below, it is of course that the constituent elements (including steps as elements etc.) are not necessarily indispensable, except for the case where it is explicitly indicated that a specific element is indispensable, or it is theoretically clear that a specific element is indispensable. Similarly, in the following explanations of the embodiments, when shapes, positional relationship etc. of constituent elements etc. are mentioned, they include substantially similar or analogous shapes and so forth, except for the case where it is explicitly indicated, or it is theoretically clear that the above is not true. This shall also apply to the numerical values and ranges mentioned above. In addition, even in a plane view, hatching may be used for ease of understanding.

In the following embodiments, the object of suppressing accumulation of electrical charge in an insulating film and reduction of insulation withstand voltage thereof even when surfaces above and below the hollow part contact with each other is achieved by disposing a conductive film so as to be exposed to the hollow part from either one or both of upside and downside of the hollow part.

Embodiment 1

In the embodiment 1, the object of suppressing accumulation of electrical charge in an insulating film and reduction of insulation withstand voltage thereof even when surfaces above and below the hollow part contact with each other at the time of driving is achieved by disposing a conductive film so as to be exposed to the hollow part from the underside of the hollow part.

Figure 1:
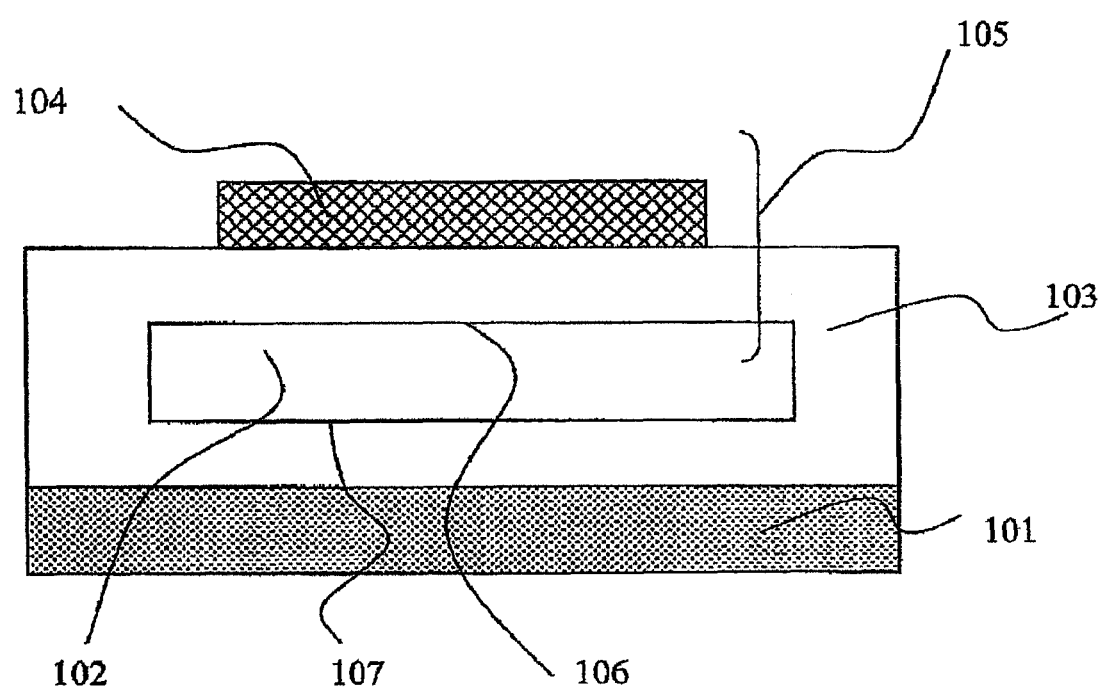
FIG. 1 is a sectional view of an ultrasonic transducer examined by the inventors of the present invention.
Figure 2:
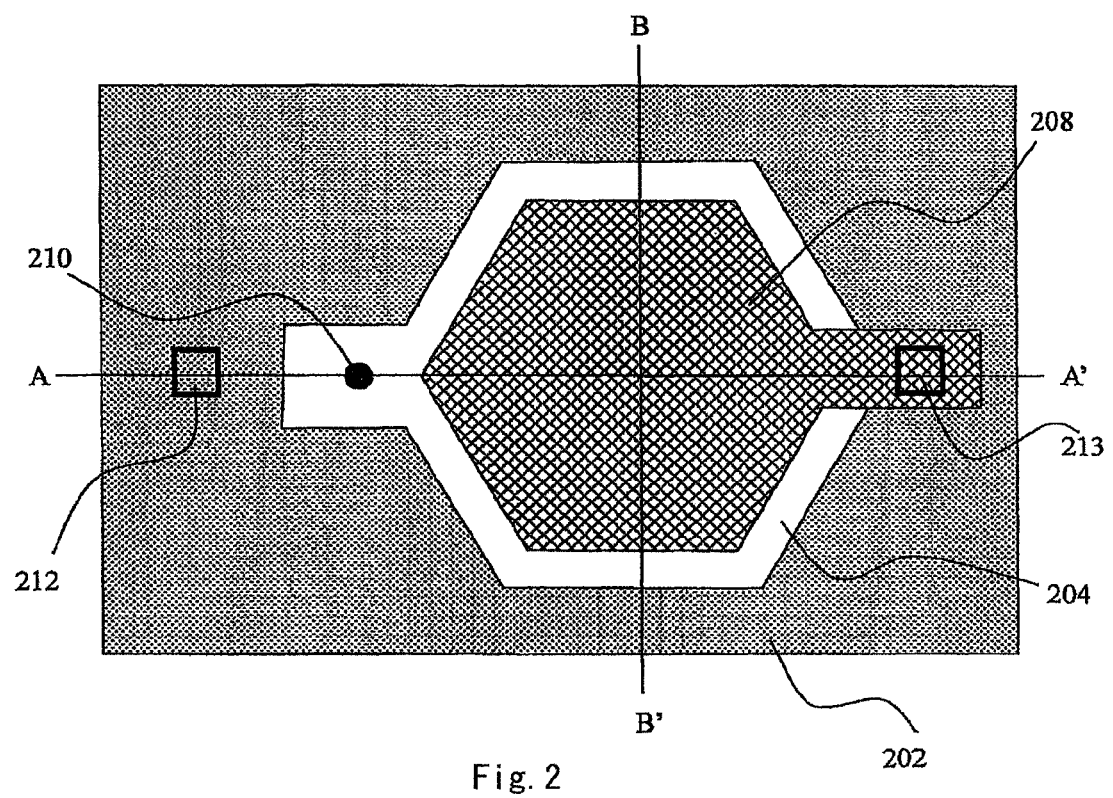
FIG. 2 is a top view of an ultrasonic transducer according to the embodiment 1 of the present invention, in which the hollow part has a hexagonal shape as seen from above.

FIG. 2 is a top view of an ultrasonic transducer (CMUT) according to the embodiment 1. FIG. 2 shows a single CMUT cell. The CMUT cell comprises a lower electrode 202, a hollow part 204 formed above the lower electrode 202, an upper electrode 208 disposed above the hollow part 204, and so forth. An etching hole 210 for forming the hollow part is communicated with a portion to become the hollow part 204. An opening 212 is provided so as to reach the lower electrode 202, and an opening 213 is provided so as to reach the upper electrode 208. Between the lower electrode 202 and the hollow part 204, an insulating film 203 consisting of a silicon oxide film is formed so as to cover the lower electrode 202, and between the upper electrode 208 and the hollow part 204, an insulating film 207 consisting of a silicon oxide film is formed so as to cover the hollow part 204 and the lower electrode 202. However, these insulating films are not shown in the drawing, in order to show the hollow part 204 and the lower electrode 202. Moreover, a conductive film 221 is formed so as to be exposed to the hollow part 204, but it is not shown in the drawing.

Figure 3:
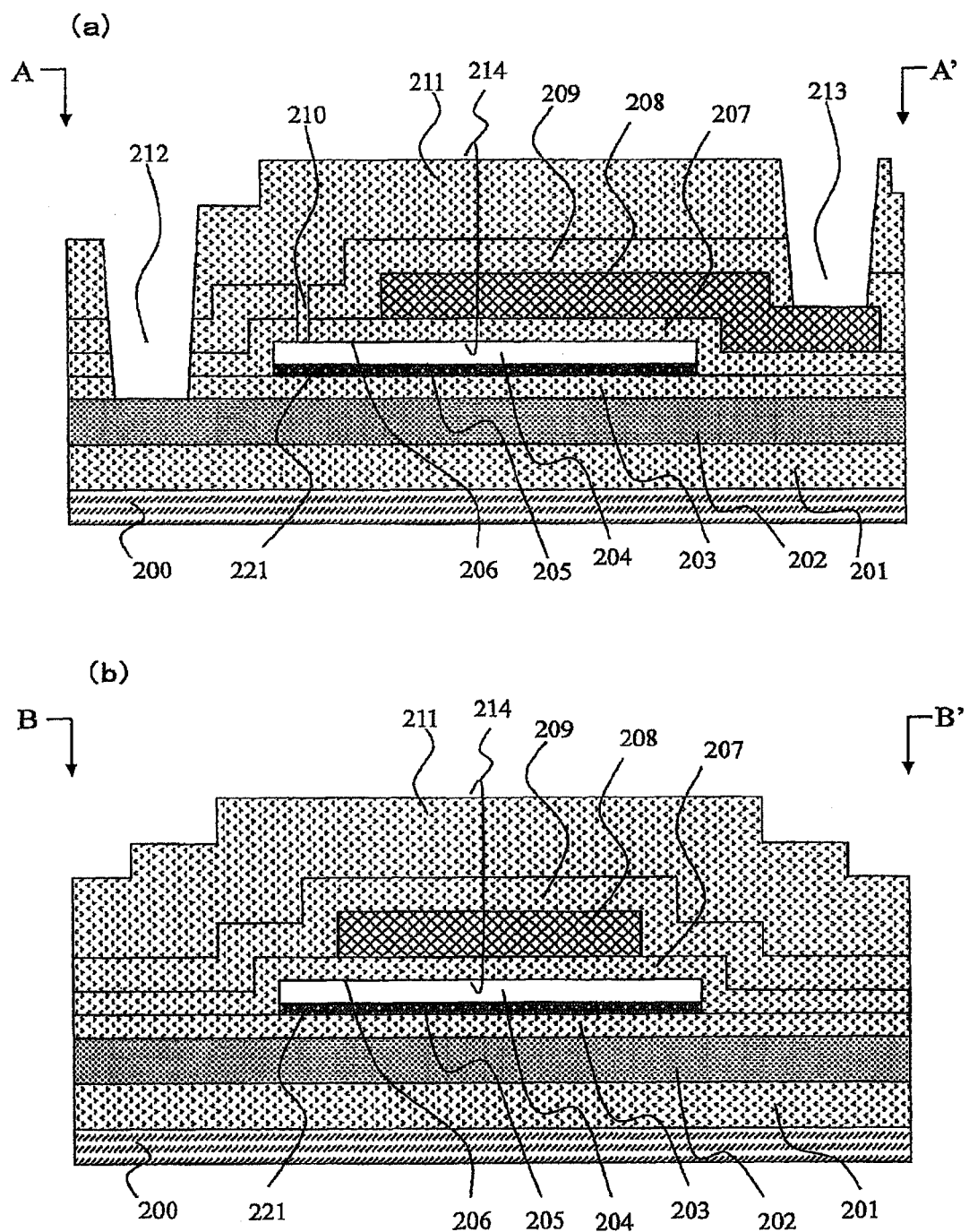
FIG. 3, (a) is a sectional view of the ultrasonic transducer shown in FIG. 2 along the line A-A' drawn in FIG. 2, and (b) is a sectional view of the same along the line B-B' drawn in FIG. 2.

FIG. 3, (a) is a sectional view of the ultrasonic transducer along the line A-A' drawn in FIG. 2, and (b) is a sectional view of the same along the line B-B' drawn in FIG. 2. As shown in FIGS. 3, (a) and (b), the lower electrode 202 of the CMUT is disposed on the insulating film 201 consisting of a silicon oxide film and formed on a semiconductor substrate 200. Above the lower electrode 202, the hollow part 204 is formed through the insulating film 203 consisting of a silicon oxide film. Further, a conductive film 221 is disposed at such a position that it overlaps with the hollow part as seen from above so as to be exposed to the hollow part 204. The surfaces 205 and 206 correspond to upper and lower end planes of the hollow part 204. The insulating film 207 consisting of a silicon oxide film is disposed so as to surround the hollow part 204 and the conductive film 221, and the upper electrode 208 is formed on the insulating film 207. An insulating film 209 and an insulating film 211 consisting of silicon nitride films are disposed on the upper electrode 208. Further, the etching hole 210 is formed in the insulating film 207 and the insulating film 209 so as to penetrate these films, and filled with the insulating film 211. This etching hole 210 is formed for forming the hollow part 204. A membrane 214 according to the embodiment 1 is constituted with the insulating films 207, 209 and 211 and the upper electrode 208.

Figure 4:
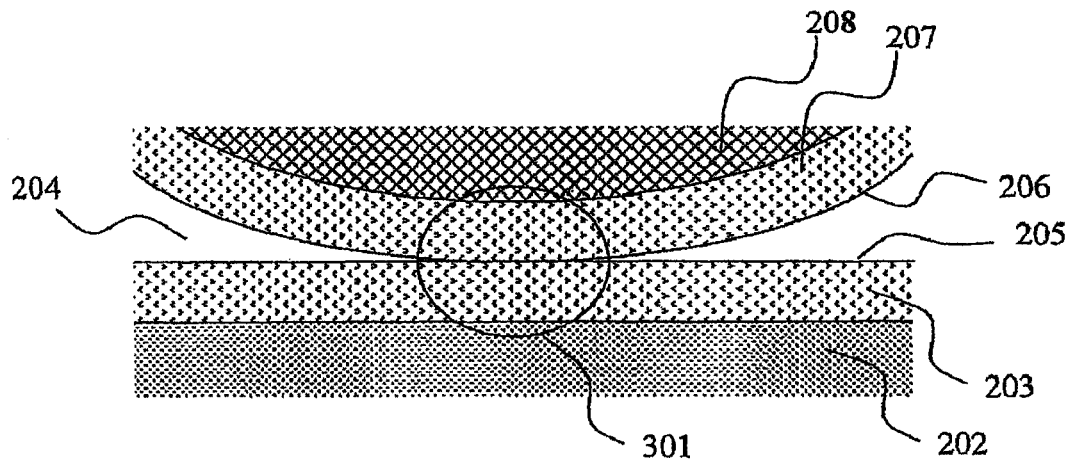
FIG. 4 include enlarged views of a contact region of an ultrasonic transducer according to the embodiment 1 in a state that the surfaces above and below the hollow part contact with each other in that region when the transducer is driven, (a) is such an enlarged view for the case where the conductive film is not disposed, and (b) is such an enlarged view for the case where the conductive film 221 is disposed so as to be exposed to the hollow part.
Figure 4:
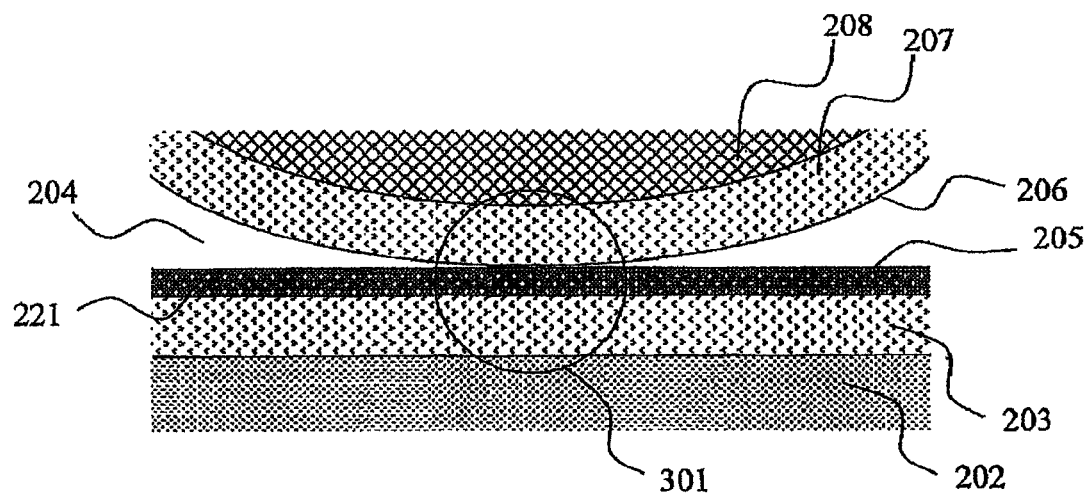

The characteristics of the embodiment 1 will be explained with reference to FIG. 4. FIG. 4 includes enlarged views of a region in which the surface 206 above the hollow part 204 and the surface 205 below the hollow part 204 contact with each other (contact region), when CMUT is driven, and the membrane 214 vibrates. FIG. 4, (a) is for the case where the conductive film is not disposed, and FIG. 4, (b) is for the case where the conductive film 221 is disposed according to the embodiment 1. This conductive film 221 is an electrically isolated film.

As shown in FIG. 4, (a), when CMUT is driven, in the region 301 where the surface 206 above the hollow part 204 and the surface 205 below the hollow part 204 contact with each other, there is provided a structure that there are only the insulating film 203 and the insulating film 207 between the lower electrode 202 and the upper electrode 208, and in the other region, there is also the hollow part 204 between the upper electrode and the lower electrode in addition to the insulating films 203 and 207. As a result, the electric field intensity in the insulating films 203 and 207 of the contact region 301 becomes higher than the electric field intensity in the insulating film 203 and 207 of the region other than the contact region 301. Therefore, extremely weak leak electric currents between the lower electrode 202 and the upper electrode 208 flowing through the insulating films 203 and 207 concentrate in the contact region 301, which leads to degradation of dielectric strength of the insulating films 203 and 207.

On the other hand, when the conductive film 221 is disposed so that it is exposed to the hollow part 204 as shown in FIG. 4, (b), since the conductive film 221 is an electrically isolated conductive film, the conductive film 221 is made to have a potential corresponding to a distributed potential of the potential difference between the lower electrode 202 and the upper electrode 208 by the capacitance of the insulating films 203 and 207 and the hollow part 204 existing between the lower electrode 202 and the upper electrode 208, and the whole conductive film becomes isopotential. Therefore, in the insulating film 203 between the conductive film 221 and the lower electrode 202, electric field intensity is the same in the contact region 301 and the other region, thus concentration of the leak electric currents in the contact region 301 can be suppressed, and accumulation of electrical charge in the insulating film 203 and degradation of dielectric strength thereof can be suppressed. Although the electric field intensity in the insulating film 207 of the contact region 301 is still higher than that of the region except for the contact region 301, if the direction of the flow of electric current, i.e., the polarity of the electric potential between the upper electrode and the lower electrode, is taken into consideration, degradation of the insulating film 207 can also be suppressed. In the CMUT according to the embodiment 1 shown in FIGS. 2, 3, and 4, (b) using, for example, the lower electrode and upper electrode consisting of metals, it is sufficient to make the potential of the lower electrode to be lower than that of the upper electrode. In such a case, since the leak electric currents are produced by electrons, and electrons flow from the electrode of lower potential to the electrode of higher potential, electrons flow from the lower electrode 202 to the insulating film 203, the conductive film 221, the insulating film 207, and then the upper electrode in this order. In this example, since the dielectric strength of the insulating film 203 is not easily degraded, flow amount of electrons constituting leak electric currents itself can also be reduced. Therefore, even if the electric field intensity in the insulating film 207 of the contact region 301 remains to be higher than that in the region except for the contact region 301, the flow amount of electrons (current amount) concentrated in the contact region 301 itself can be made small, and therefore accumulation of electrical charge in the insulating film 207 and degradation of dielectric strength thereof can be suppressed. That is, when the conductive film is disposed on the lower electrode side, degradation of the dielectric strength of the insulating films 203 and 207 can be suppressed by applying a direct voltage between the upper electrode and the lower electrode, so that potential of the lower electrode is lower than that of the upper electrode. Moreover, since degradation of the dielectric strength of the insulating films 203 and 207 can be suppressed even when the surfaces above and below the hollow part contact with each other, the membrane can be vibrated to such an extent that the surfaces above and below the hollow part contact with each other, that is, the membrane can be vibrated by fully utilizing the thickness of the hollow part at maximum, and thus transmission sound pressure can be improved. Further, thickness of the hollow part can be made thinner to the minimum thickness that can secure amplitude of the membrane vibration that can provide sound pressure required for the diagnosis, and thus reception sensitivity can be improved.

Hereafter, the effects of the invention of the embodiment 1 will be explained by contrasting it with the conventional technique disclosed in Patent document 2. In the conventional technique, it is disclosed that a floating electrode is embedded in an insulating film and electrified to make the direct voltage unnecessary or reduce the direct voltage. On the other hand, the invention of the embodiment 1 uses a structure that the conductive film corresponding to the floating electrode is not embedded in an insulating film, but is exposed to the hollow part. In this structure, there is not any insulating film between the conductive film and the hollow part, and the conductive film is exposed to the hollow part. This is because it is indispensable for the invention of the embodiment 1 to use a conductive film that is not charged or is not easily charged in order to achieve the aforementioned object. Therefore, in order to make the conductive film difficult to be charged, there is employed such a structure that even if electrical charge is accumulated in the conductive film, the accumulated electrical charge is easily discharged via the hollow part.

As described above, by using such a structure that electrical charge is hardly accumulated in the conductive film, even when the surfaces above and below the hollow part contact with each other at the time of driving of the transducer, there is extremely little accumulated electrical charge, and therefore it can be prevented from flowing into the insulating film 207. Therefore, accumulation of electrical charge in the insulating film 207 caused by the electric field between the floating electrode and the upper electrode and degradation of dielectric strength thereof can be more suppressed compared with the CMUT of Patent document 2, which comprises the floating electrode charged to such a degree that the direct voltage is effectually reduced. Moreover, while the accumulated electrical charges reduces with lapse of time in this conventional technique, the technique of the embodiment 1 provides very little change of the accumulated electrical charge due to such discharge, therefore the direct voltage set to be an optimal value beforehand is not need to be changed more than necessary, and thus CMUT can be used under a favorable condition, which is substantially the optimal value, for a long period of time.

Next, the method for producing the CMUT cell described as the embodiment 1 will be explained with reference to the drawings. In FIGS. 5 to 14, (a) shows section along the lines A-A' and (b) shows section along the lines B-B' drawn in FIG. 2, respectively.

Figure 5:
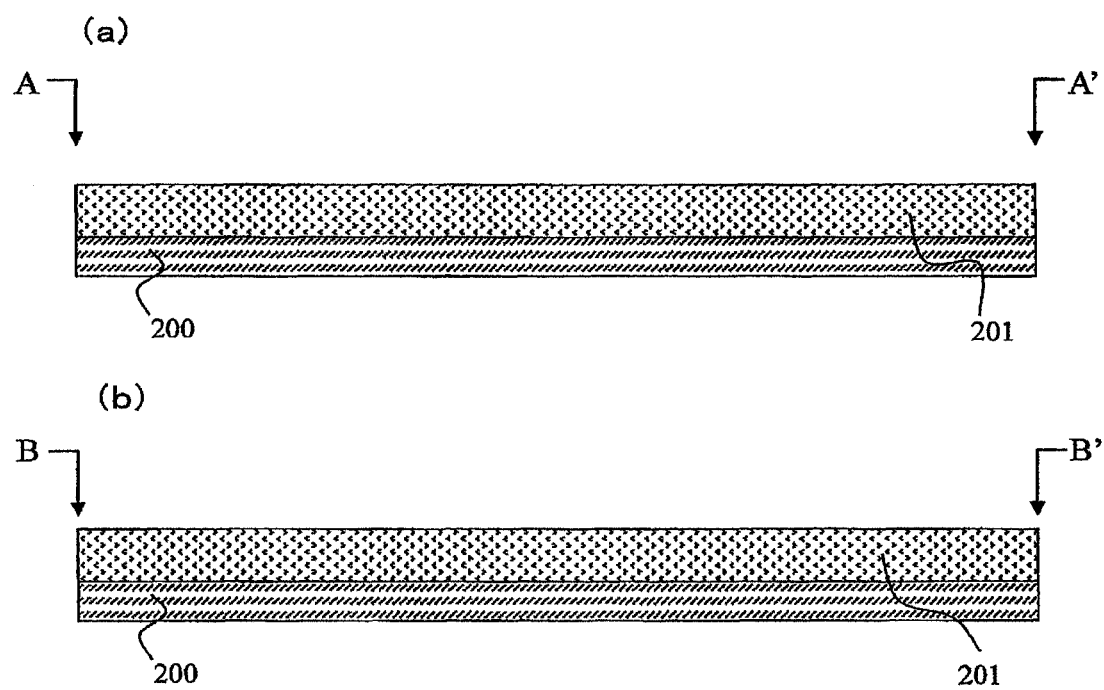
FIGS. 5, (a) and (b) are sectional views for explaining a manufacturing step of the ultrasonic transducer shown in FIG. 2 along the lines A-A' and B-B' drawn in FIG. 2, respectively.
Figure 6:
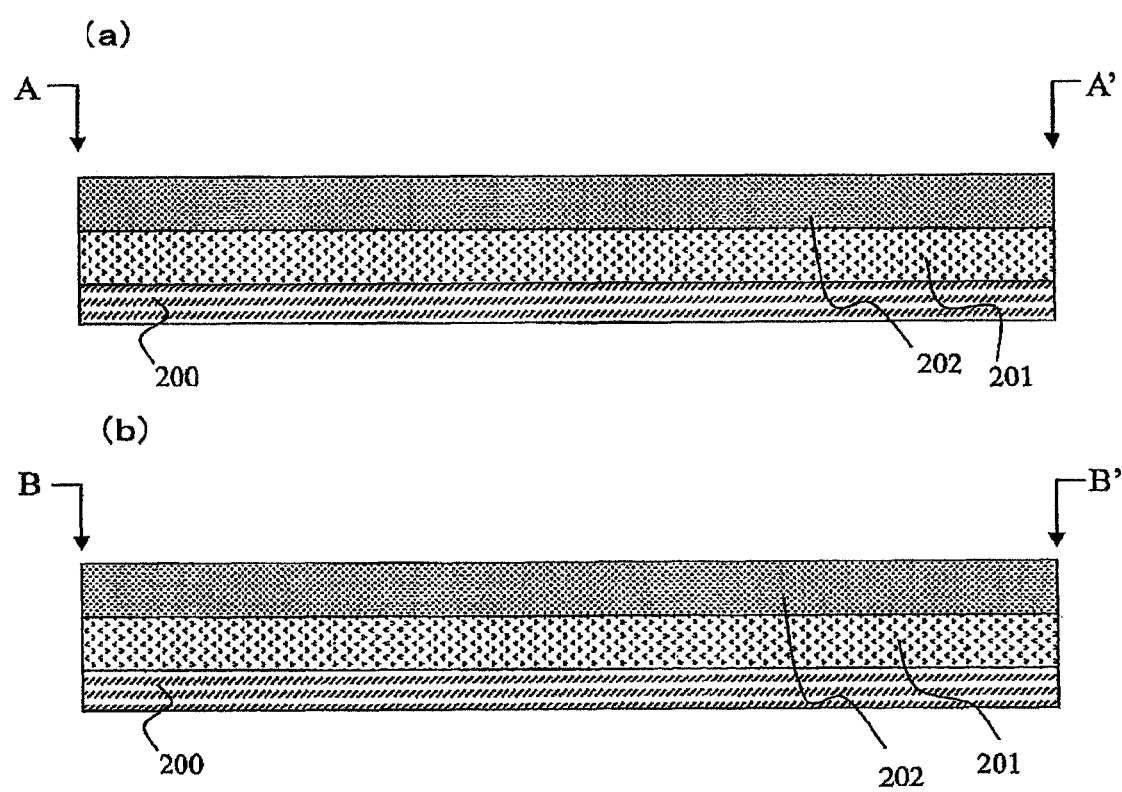
FIGS. 6, (a) and (b) are sectional views for explaining a manufacturing step of the ultrasonic transducer following the step shown in FIGS. 5, (a) and (b).

First, as shown in FIGS. 5, (a) and (b), the insulating film 201 consisting of a silicon oxide film is deposited in 400 nm thickness on the semiconductor substrate 200 by the plasma-CVD (Chemical Vapor Deposition) method. Then, a titanium nitride film, an aluminum alloy film, and a titanium nitride film are deposited in 100 nm, 600 nm and 100 nm thicknesses, respectively, on the insulating film 201 by the sputtering method, and then patterning is performed by the photolithography and dry etching techniques to form the lower electrode 202 (FIGS. 6, (a) and (b)).

Figure 7:
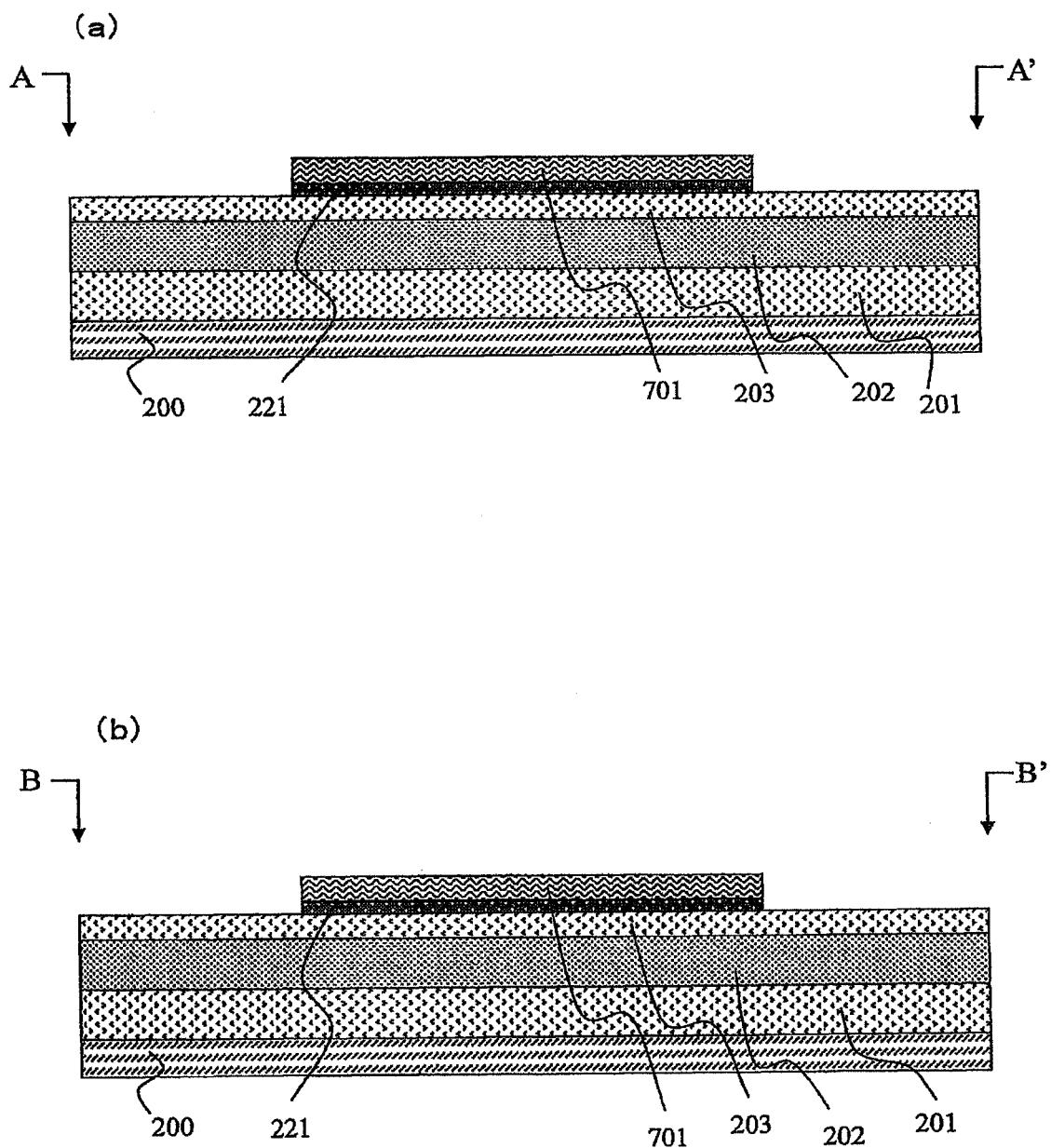
FIGS. 7, (a) and (b) are sectional views for explaining a manufacturing step of the ultrasonic transducer following the step shown in FIGS. 6, (a) and (b).

Then, as shown in FIGS. 7, (a) and (b), the insulating film 203 consisting of a silicon oxide film is deposited in 100 nm thickness on the lower electrode 202 by the plasma-CVD method, then an aluminum alloy film serving as the electrically isolated conductive film 221 is deposited in 50 nm thickness on the upper surface of the insulating film 203 by the sputtering method, a polycrystalline silicon film is further deposited in 100 nm thickness by the plasma-CVD method, and patterning is performed for the aluminum alloy film and the polycrystalline silicon film by photolithography and dry etching techniques to form a sacrificial layer 701 consisting of the conductive film 221 and the polycrystalline silicon film on the insulating film 203. The hollow part is formed at the position of the sacrificial layer 701 in a subsequent step.

Figure 8:
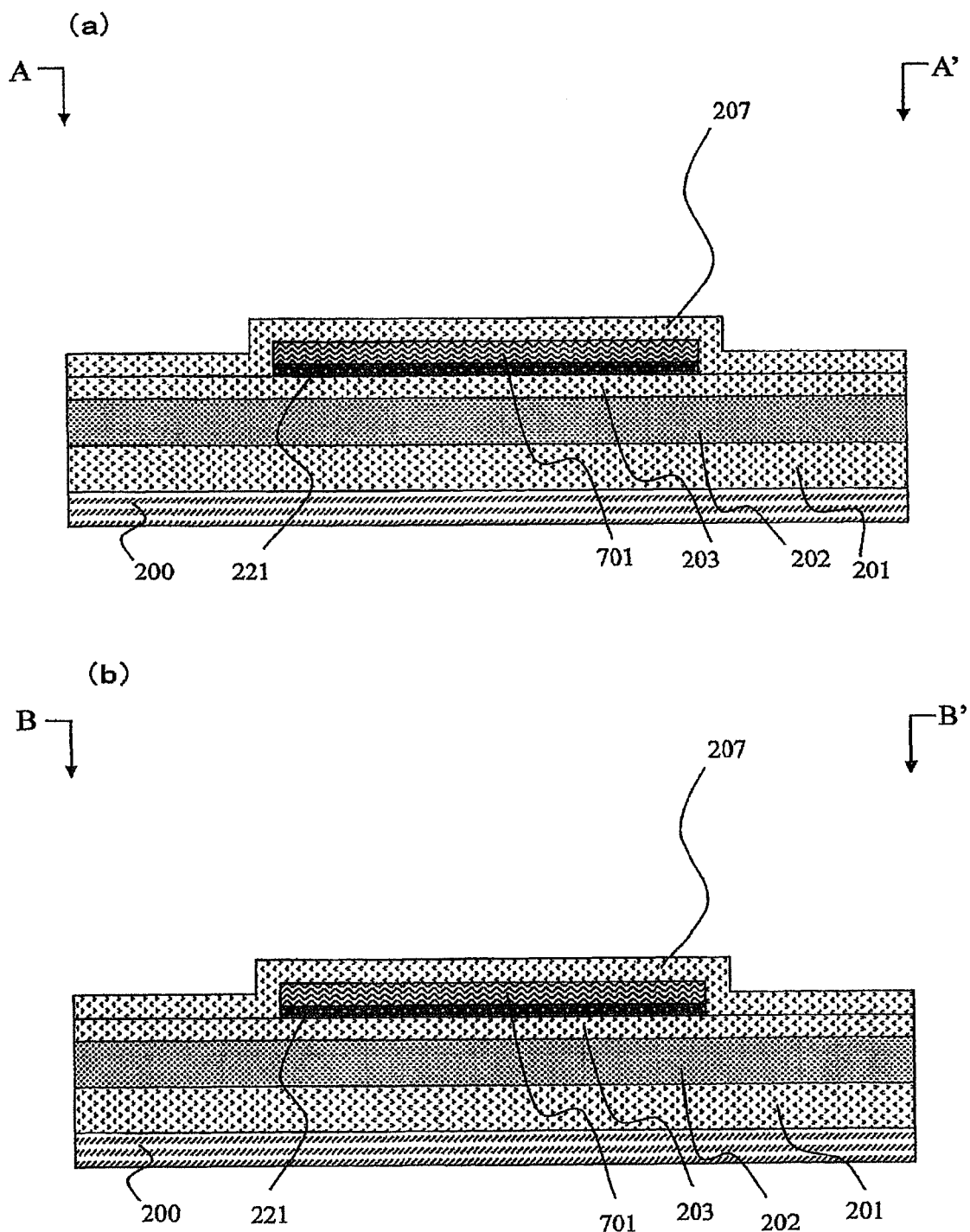
FIGS. 8, (a) and (b) are sectional views for explaining a manufacturing step of the ultrasonic transducer following the step shown in FIGS. 7, (a) and (b).
Figure 9:
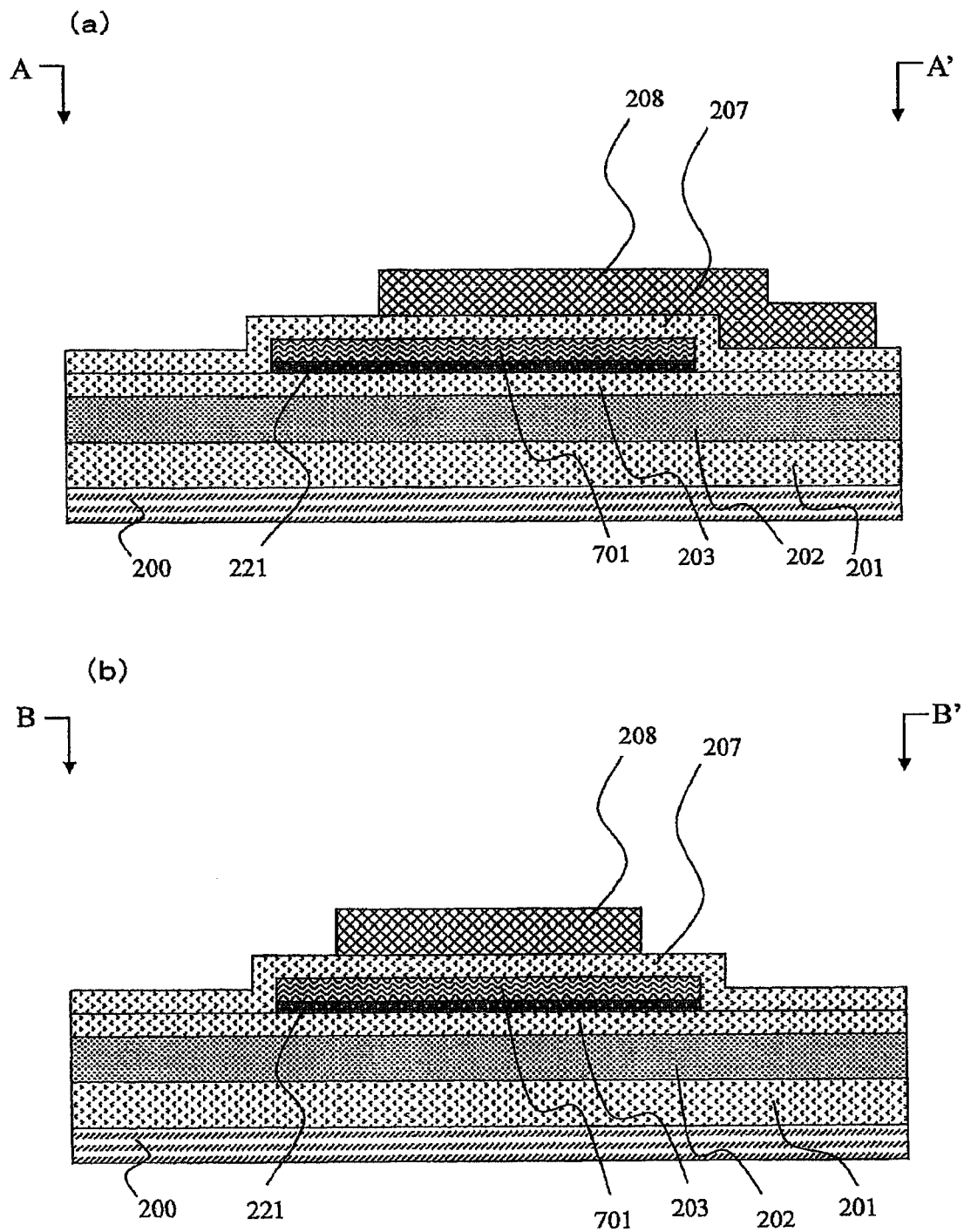
FIGS. 9, (a) and (b) are sectional views for explaining a manufacturing step of the ultrasonic transducer following the step shown in FIGS. 8, (a) and (b).

Then, the insulating film 207 consisting of a silicon oxide film is deposited in 100 nm thickness by the plasma-CVD method so as to cover the conductive film 221, the sacrificial layer 701, and the insulating film 203 (FIGS. 8, (a) and (b)). Then, in order to form the upper electrode 208 of the CMUT cell, a laminate film consisting of a titanium nitride film, an aluminum alloy film, and a titanium nitride film are deposited in 50 nm, 300 nm and 50 nm thicknesses, respectively, by the sputtering method. Then, the upper electrode 208 is formed by the photolithography and dry etching techniques (FIGS. 9, (a) and (b)).

Figure 10:
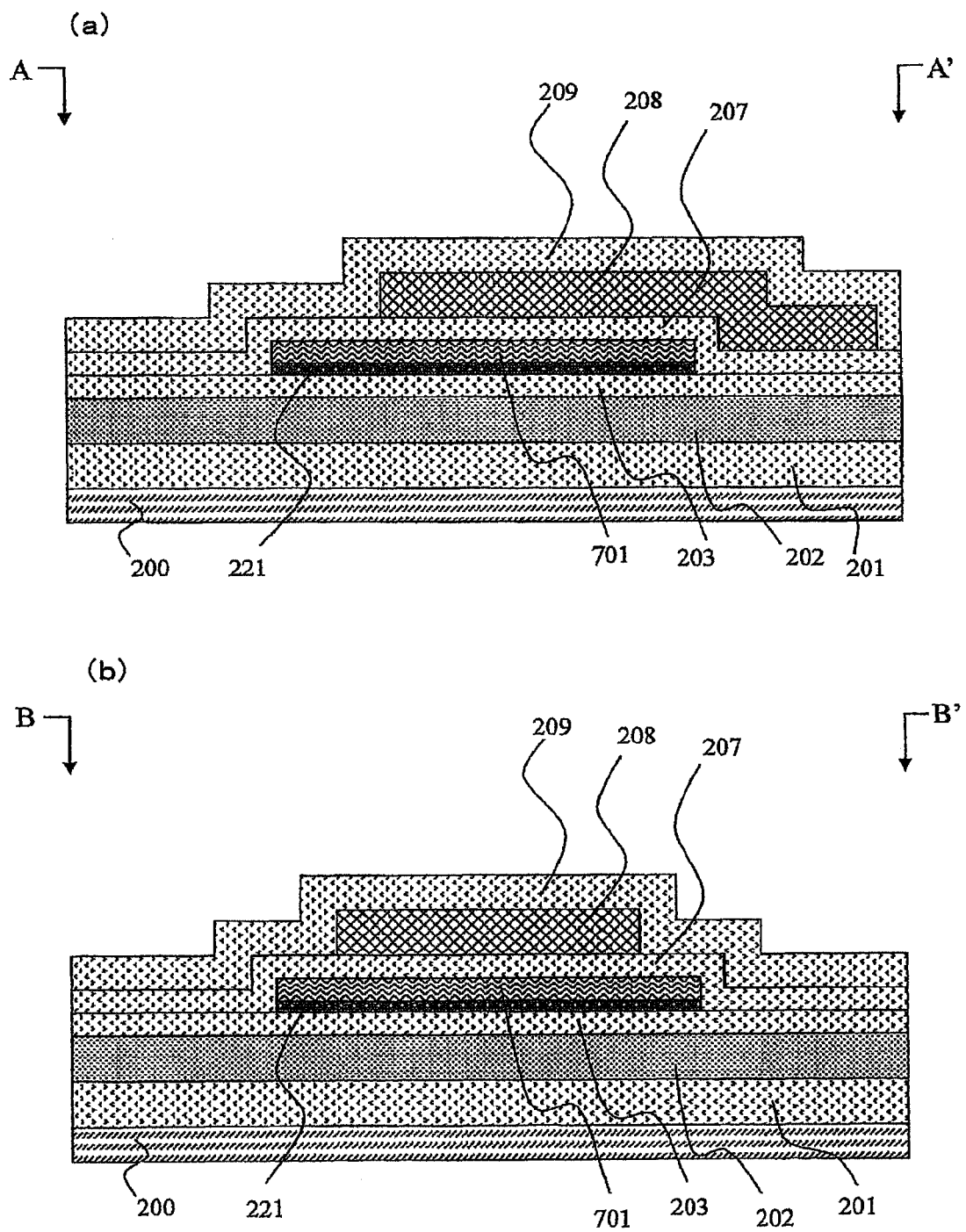
FIGS. 10, (a) and (b) are sectional views for explaining a manufacturing step of the ultrasonic transducer following the step shown in FIGS. 9, (a) and (b).
Figure 11:
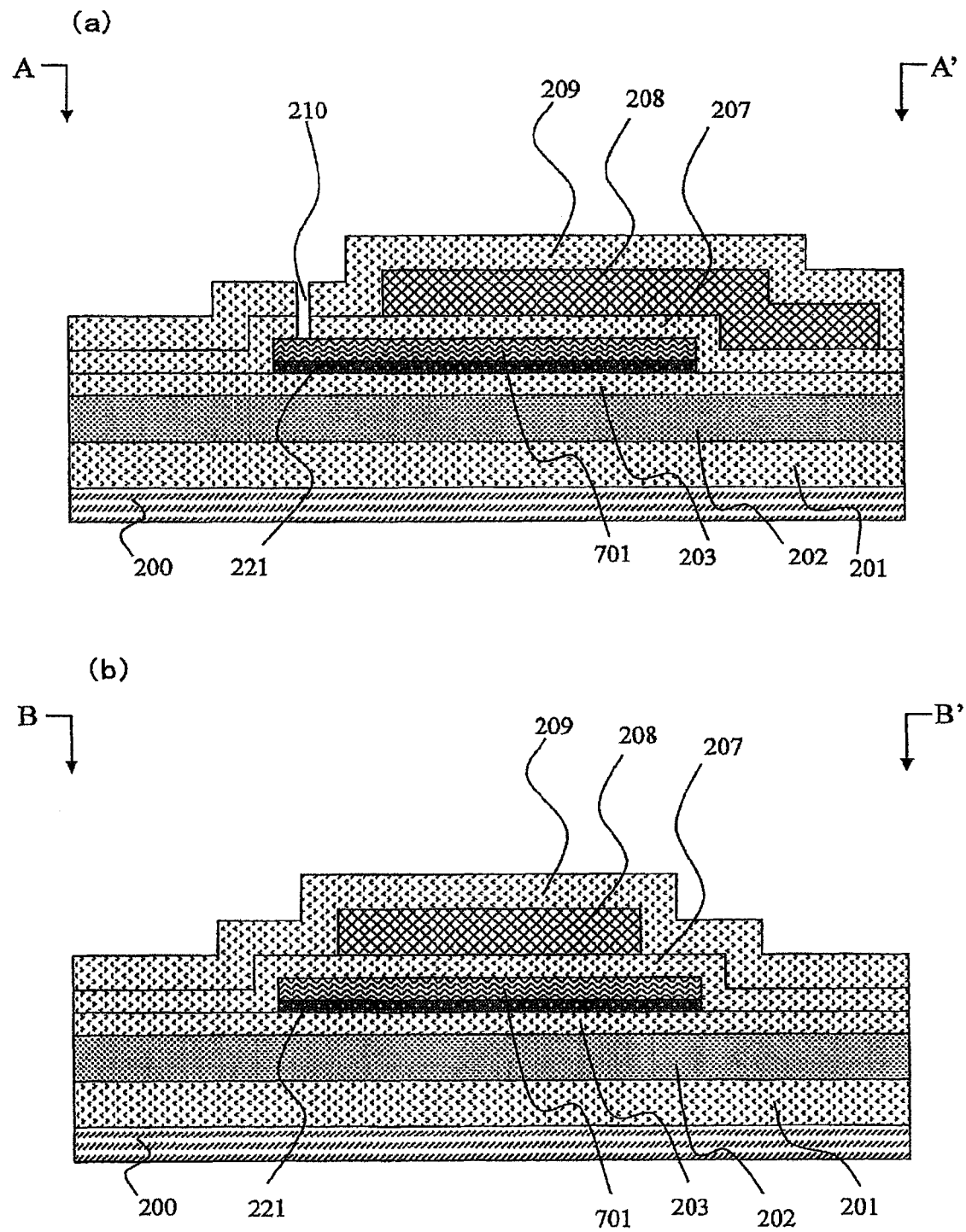
FIGS. 11, (a) and (b) are sectional views for explaining a manufacturing step of the ultrasonic transducer following the step shown in FIGS. 10, (a) and (b).
Figure 12:
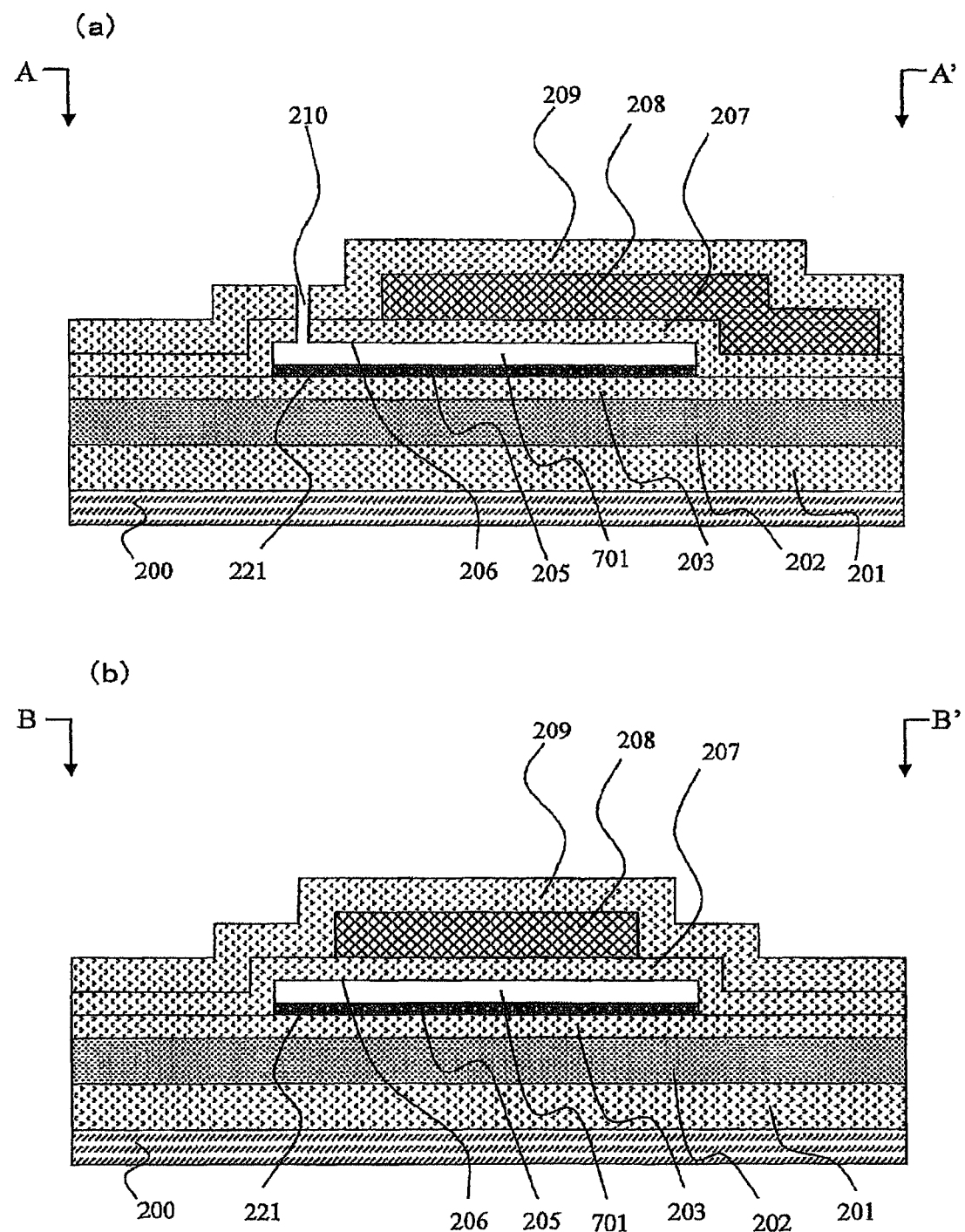
FIGS. 12, (a) and (b) are sectional views for explaining a manufacturing step of the ultrasonic transducer following the step shown in FIGS. 11, (a) and (b).

Then, by the plasma-CVD method, the insulating film 209 consisting of a silicon nitride film is deposited in 500 nm thickness so as to cover the insulating film 207 and the upper electrode 208 (FIGS. 10, (a) and (b)). Next, the etching hole 210 is formed in the insulating films 209 and 207 by using the photolithography and dry etching techniques so as to reach the sacrificial layer 701 (FIGS. 11(a) and (b)). Then, the sacrificial layer 701 is isotropically etched with xenon fluoride ($XeF_2$) gas through the etching hole 210 to form the hollow part 204 (FIGS. 12, (a) and (b)).

Figure 13:
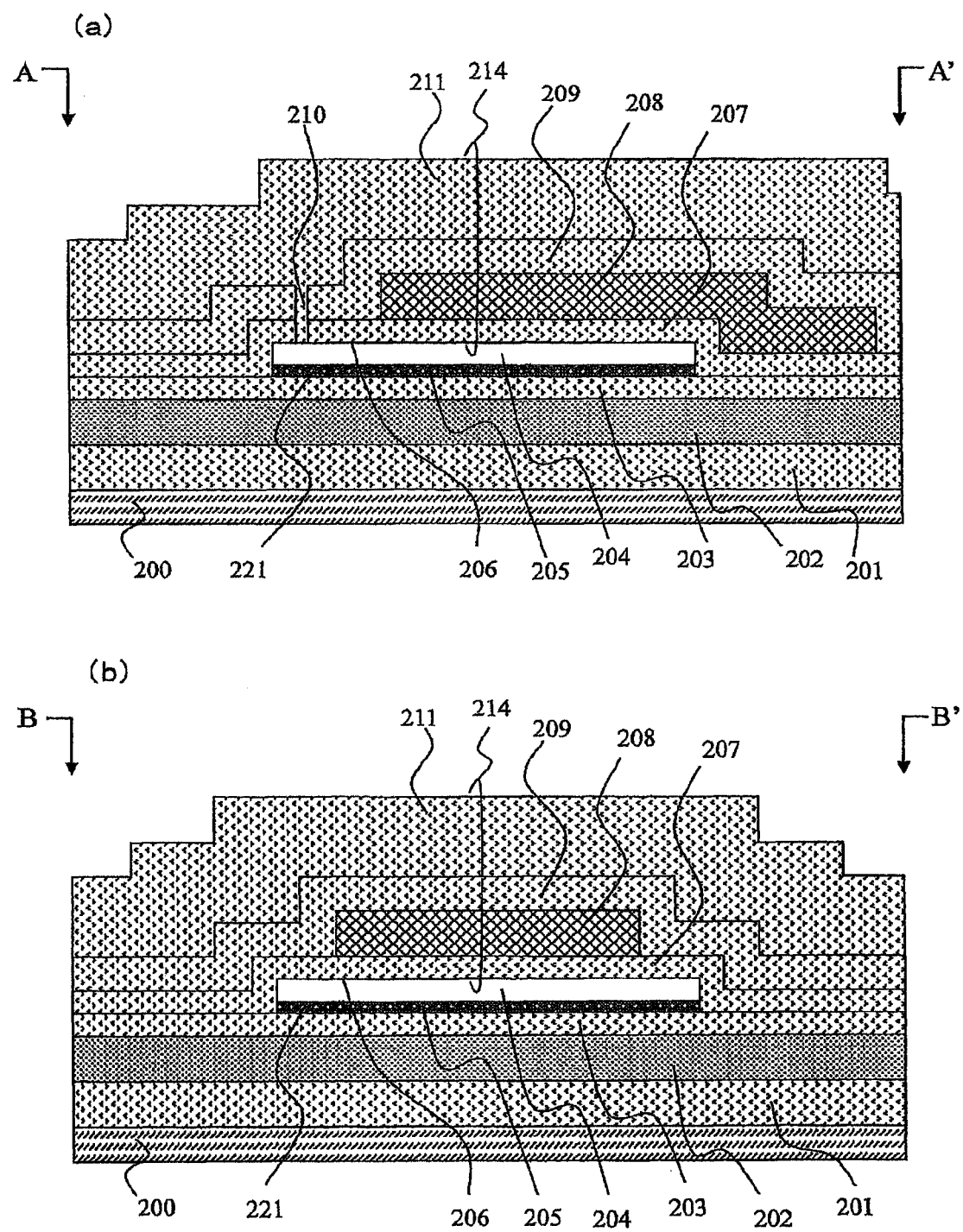
FIGS. 13, (a) and (b) are sectional views for explaining a manufacturing step of the ultrasonic transducer following the step shown in FIGS. 12, (a) and (b).
Figure 14:
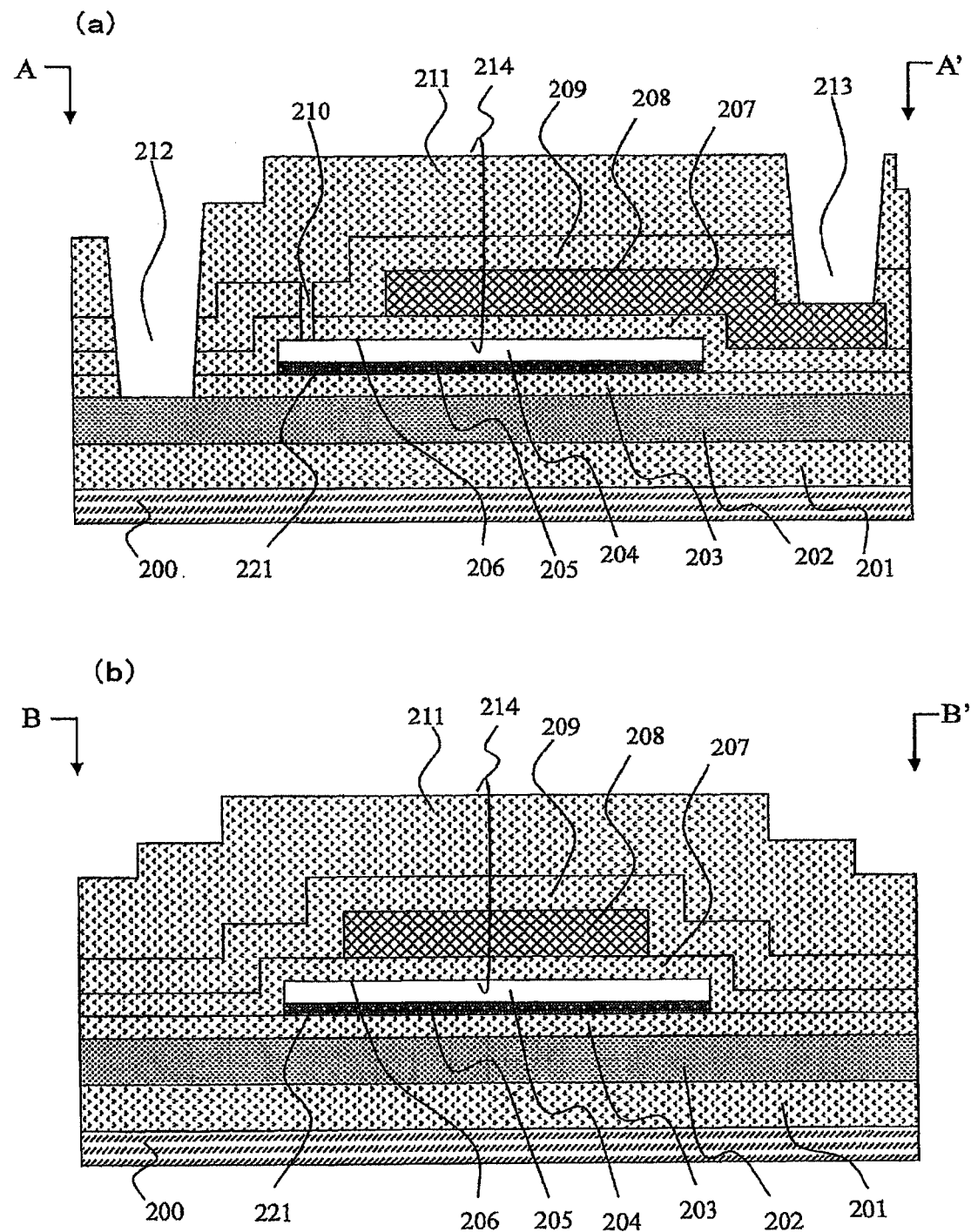
FIGS. 14, (a) and (b) are sectional views for explaining a manufacturing step of the ultrasonic transducer following the step shown in FIGS. 13, (a) and (b).

Then, in order to fill the etching hole 210, the insulating films 211 consisting of a silicon nitride film is deposited in 800 nm thickness by the plasma-CVD method (FIGS. 13, (a) and (b)). By this step, the membrane 214 consisting of the insulating films 203, 209 and 211, and the upper electrode 208 is formed. Then, the opening 212 for providing electric connection to the lower electrode 202 and the opening 213 for providing electric connection to the upper electrode 208 are formed by using the photolithography and dry etching techniques (FIGS. 14, (a) and (b)). In this way, the CMUT cell of the embodiment 1 can be formed.

Figure 15:
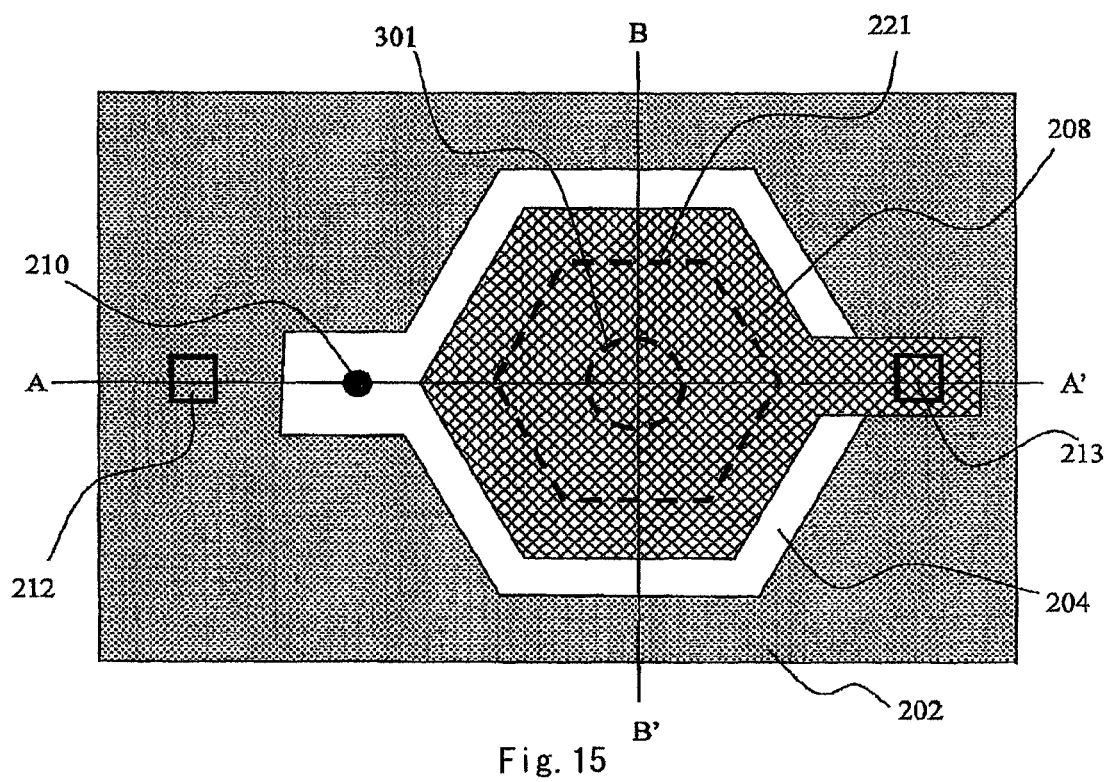
FIG. 15 is a top view of an ultrasonic transducer according to the embodiment 1, in which the hollow part has a hexagonal shape as seen from above, and the conductive film is smaller than the hollow part as seen from above.
Figure 16:
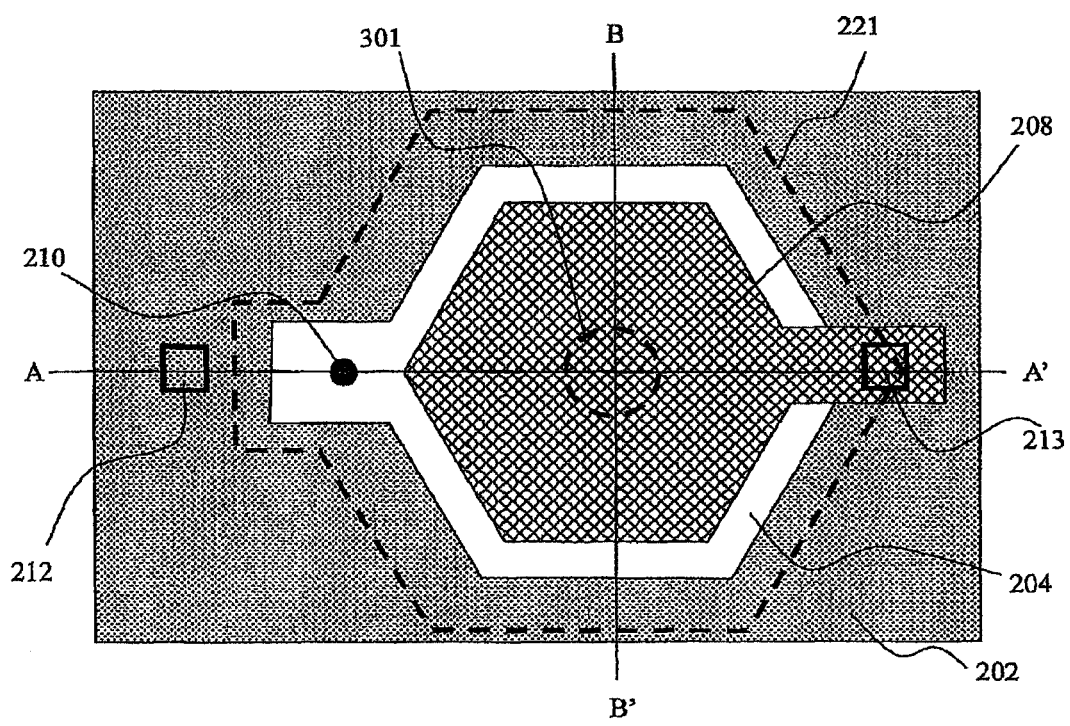
FIG. 16 is a top view of an ultrasonic transducer according to the embodiment 1, in which the hollow part has a hexagonal shape as seen from above, and the conductive film is larger than the hollow part as seen from above.

The size of the conductive film 221 as seen from above will be explained below. In the example shown in FIG. 2, the hollow part 204 and the conductive film 221 have the same shape as seen from above, and are disposed so as to overlap with each other. However, they are not limited to have such a configuration. It is sufficient that the conductive film 221 has a size larger than the region where the surface 206 above the hollow part and the surface 205 below the hollow part contact with each other at least at the time of driving. In other words, this conductive film may be provided so that, in a static state, it exists in a region including a predetermined area of which center is the center of gravity of the membrane, in which the perpendicular displacement of the membrane becomes maximum. This is because concentration of the electric field can be more suppressed compared with the case using no conductive film. If the ultrasonic transducer is used at a voltage in such a range that the surfaces above and below the hollow part contact with each other at a point, it is sufficient that the conductive film is provided for an area including the point. On the other hand, when the ultrasonic transducer is used at a voltage in such a range that the surfaces above and below the hollow part contact with each other in an area, not a point, it is sufficient that the conductive film is provided for a region including the area. For example, it is sufficient that, as shown with broken lines in FIG. 15, the shape of the conductive film 221 is larger than the region 301 in which the surface 206 above the hollow part 204 and the surface 205 below the hollow part 204 contact with each other as seen from above. Alternatively, as shown with the broken lines in FIG. 16, the shape of the conductive film 221 may be larger than the hollow part 204 as seen from above. In this case, concentration of the electric currents in the insulating film of the contact region 301 can be further reduced due to the larger size of the conductive film 221.

In addition, although the CMUT cell shown FIG. 2 has a hexagonal shape as the planar shape, the shape is not limited such a shape, and may be, for example, a circular shape or a rectangular shape. Further, the materials constituting the CMUT cell shown as the embodiment 1 just constitute an example of the combination thereof. The material of the sacrificial layer may also be any material that can secure etching selectivity with respect to the materials for the insulating films and the conductive films surrounding the sacrificial layer. Therefore, the conductive film may be a metal film or the like, rather than a polycrystalline silicon film. Furthermore, it is sufficient that the lower electrode of CMUT is a conductive film, or it may be a semiconductor substrate, or as shown in FIG. 3, a conductive film on an insulating film formed on a semiconductor substrate, or a conductive film on a semiconductor substrate in which a signal processing circuit is formed.

Embodiment 2

Whereas the embodiment 1 is an embodiment in which the conductive film is exposed to the hollow part from the underside of the hollow part, the embodiment 2 is an embodiment in which the conductive film is exposed to the hollow part from the upside of the hollow part.

Figure 17:
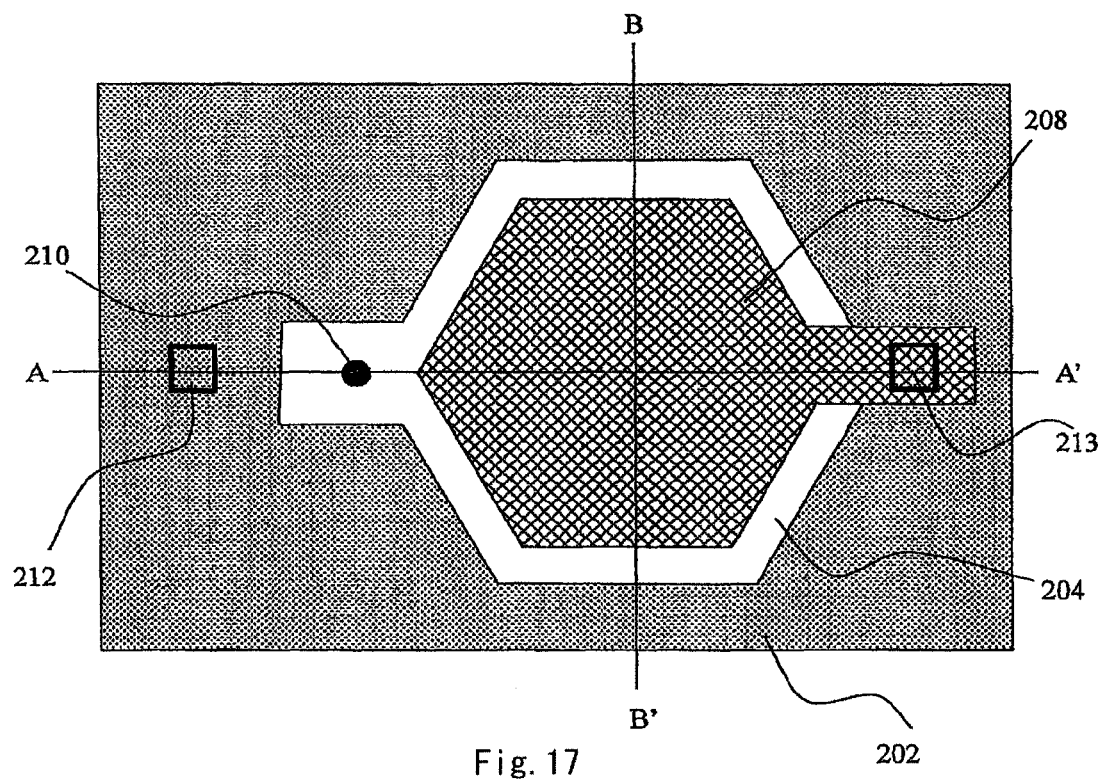
FIG. 17 is a top view of an ultrasonic transducer according to the embodiment 2, in which the hollow part has a hexagonal shape as seen from above.

FIG. 17 is a top view of an ultrasonic transducer (CMUT) according to the embodiment 2. FIG. 17 shows a single CMUT cell. The CMUT cell is constituted with the lower electrode 202, the hollow part 204 formed above the lower electrode 202, the upper electrode 208 formed above the hollow part 204, and so forth. The etching hole 210 for forming the hollow part is communicated with a portion to become the hollow part 204. The opening 212 is provided so as to reach the lower electrode 202, and the opening 213 is provided so as to reach the upper electrode 208. Between the lower electrode 202 and the hollow part 204, the insulating film 203 consisting of a silicon oxide film is formed so as to cover the lower electrode 202, and between the upper electrode 208 and the hollow part 204, the insulating film 207 consisting of a silicon oxide film is formed so as to cover the hollow part 204 and the lower electrode 202. However, these insulating films are not shown in the drawing, in order to show the hollow part 204 and the lower electrode 202. Moreover, the conductive film 221 is formed so as to be exposed to the hollow part 204, but it is not shown in the drawing.

Figure 18:
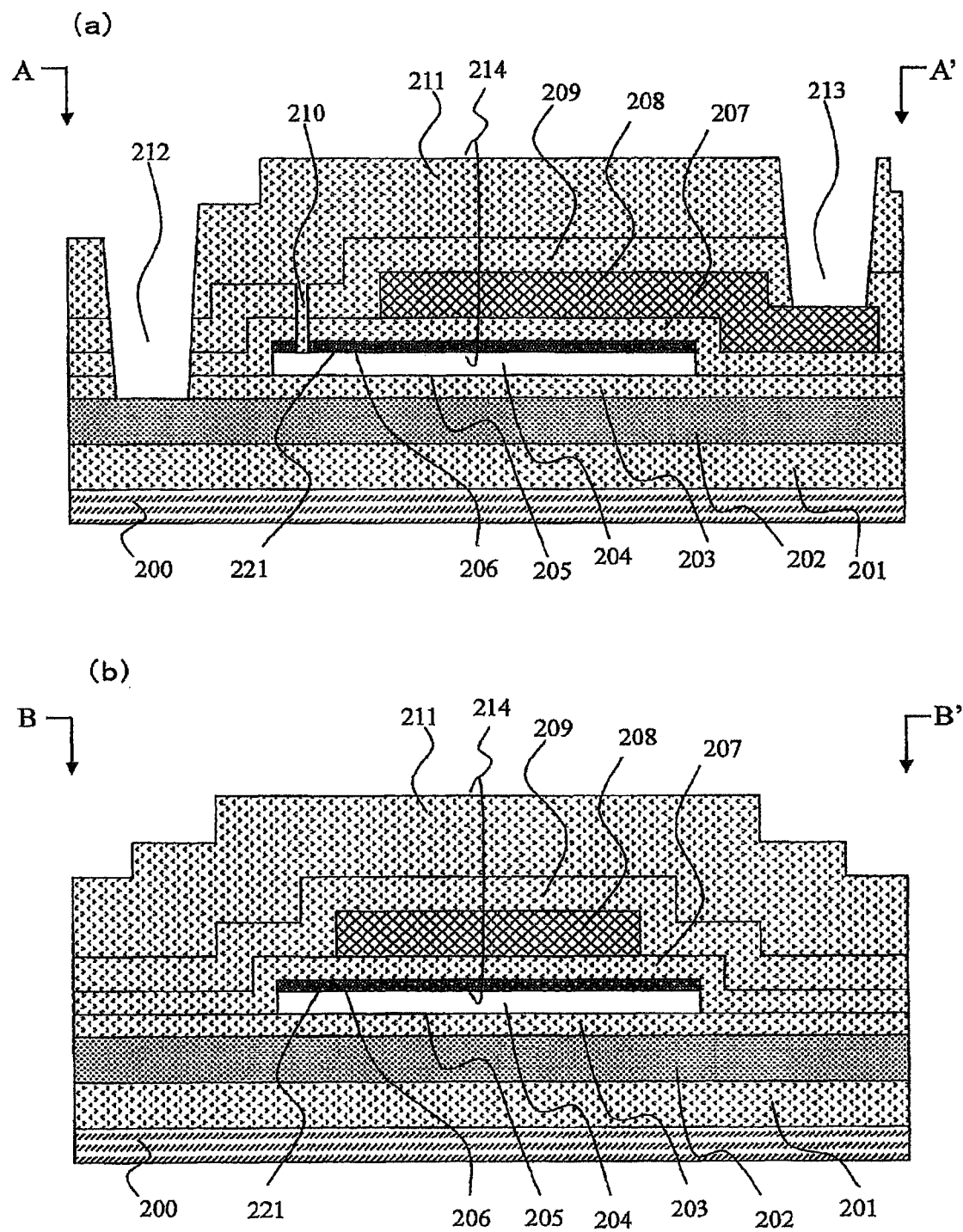
FIG. 18, (a) is a sectional view of the ultrasonic transducer shown in FIG. 17 along the line A-A' drawn in FIG. 17, and (b) is a sectional view of the same along the line B-B' drawn in FIG. 17.

FIG. 18, (a) is a sectional view along the line A-A' drawn in FIG. 17, and FIG. 18, (b) is a sectional view along the line B-B' drawn in FIG. 17. As shown in FIGS. 18, (a) and (b), the lower electrode 202 of the CMUT is disposed on the insulating film 201 consisting of a silicon oxide film and formed on the semiconductor substrate 200. Above the lower electrode 202, the hollow part 204 is formed through the insulating film 203 consisting of a silicon oxide film. Further, the conductive film 221 is disposed so that it is exposed to the hollow part 204 from the upside thereof at such a position that it overlaps with the hollow part as seen from above. The surfaces 205 and 206 correspond to upper and lower end planes of the hollow part. The insulating film 207 consisting of a silicon oxide film is disposed so as to surround the conductive film 221 and the hollow part 204, and the upper electrode 208 is formed on the insulating film 207. The insulating film 209 and the insulating film 211 consisting of silicon nitride films are disposed on the upper electrode 208. Further, the etching hole 210 is formed in the insulating film 207, the insulating film 209 and the conductive film 221 so as to penetrate these films and filled with the insulating film 211. This etching hole 210 is formed for forming the hollow part 204. The membrane 214 according to the embodiment 2 is constituted with the insulating films 207, 209 and 211, the upper electrode 208 and the conductive film 221.

The embodiment 2 is characterized in that the conductive film 221 is disposed to be exposed to the hollow part from the upside of the hollow part 204, contrary to the embodiment 1. When the conductive film 221 is disposed to be exposed to the hollow part from the upside of the hollow part 204, since the conductive film is an electrically isolated conductive film as in the embodiment 1, the conductive film 221 is made to have a potential corresponding to a distributed potential of the potential difference between the lower electrode 202 and the upper electrode 208 by the capacitance of the insulating films 203 and 207, and the hollow part 204 existing between the lower electrode 202 and the upper electrode 208, and the whole conductive film becomes isopotential. Therefore, in the insulating film 207 between the conductive film 221 and the lower electrode 208, electric field intensity is the same in the contact region 301 and the other region, thus concentration of leak electric currents in the contact region 301 can be suppressed, and accumulation of electrical charge in the insulating film 207 and degradation of dielectric strength thereof can be suppressed.

When the conductive film is disposed as described above, and the potential of the lower electrode is higher than that of the upper electrode when the CMUT is driven, electrons constituting the leak electric currents flow from the upper electrode 208 to the insulating film 207, the conductive film 221, the insulating film 207, and then the lower electrode 202 in this order. In this example, since the dielectric strength of the insulating film 207 is not degraded, flow of electrons itself can also be suppressed, and thus the leak electric currents can be reduced. Therefore, even if the electric field intensity of the insulating film 203 in the region in which the surface 206 above the hollow part and the surface 205 below the hollow part contact with each other remains to be higher than that in the region except for the contact region, the flow amount of electrons (current amount) concentrated in the contact region itself can be made small, and therefore accumulation of electrical charge in the insulating film 203 and degradation of dielectric strength thereof can be suppressed. That is, when the conductive film is disposed on the upper electrode side, degradation of the dielectric strength of the insulating films 203 and 207 can be suppressed by applying a direct voltage between the upper electrode and the lower electrode, so that potential of the lower electrode is higher than that of the upper electrode. As other effects, effects similar to those of the embodiment 1 can be obtained, provided that the relation of the upside and downside should be reversed as required.

As for the method for producing the CMUT cell of the embodiment 2, the CMUT cell can be produced by the same steps as shown in FIGS. 5 to 14, except that the order of the depositions of the conductive film and the sacrificial layer shown in FIG. 7 for the embodiment 1 should be reversed.

In the example shown in FIG. 17, the hollow part 204 and the conductive film 221 have the same shape as seen from above, and are disposed so as to overlap with each other. However, similarly to the embodiment 1, they are not limited to have such a configuration, the details of the acceptable size of the conductive film 221 as seen from above, a shape of the CPUT cell and materials constituting the CMUT cell are as described for the embodiment 1, and also similarly to the embodiment 1, the lower electrode may be a semiconductor substrate. Therefore, detailed explanations are omitted.

Embodiment 3

Although the embodiments 1 and 2 are embodiments in which the conductive film is exposed to the hollow part from either one of the upside and underside of the hollow part, the embodiment 3 is an embodiment in which both a conductive film exposed to the hollow part from the upside thereof and a conductive film exposed to the hollow part from the underside thereof are disposed.

Figure 19:
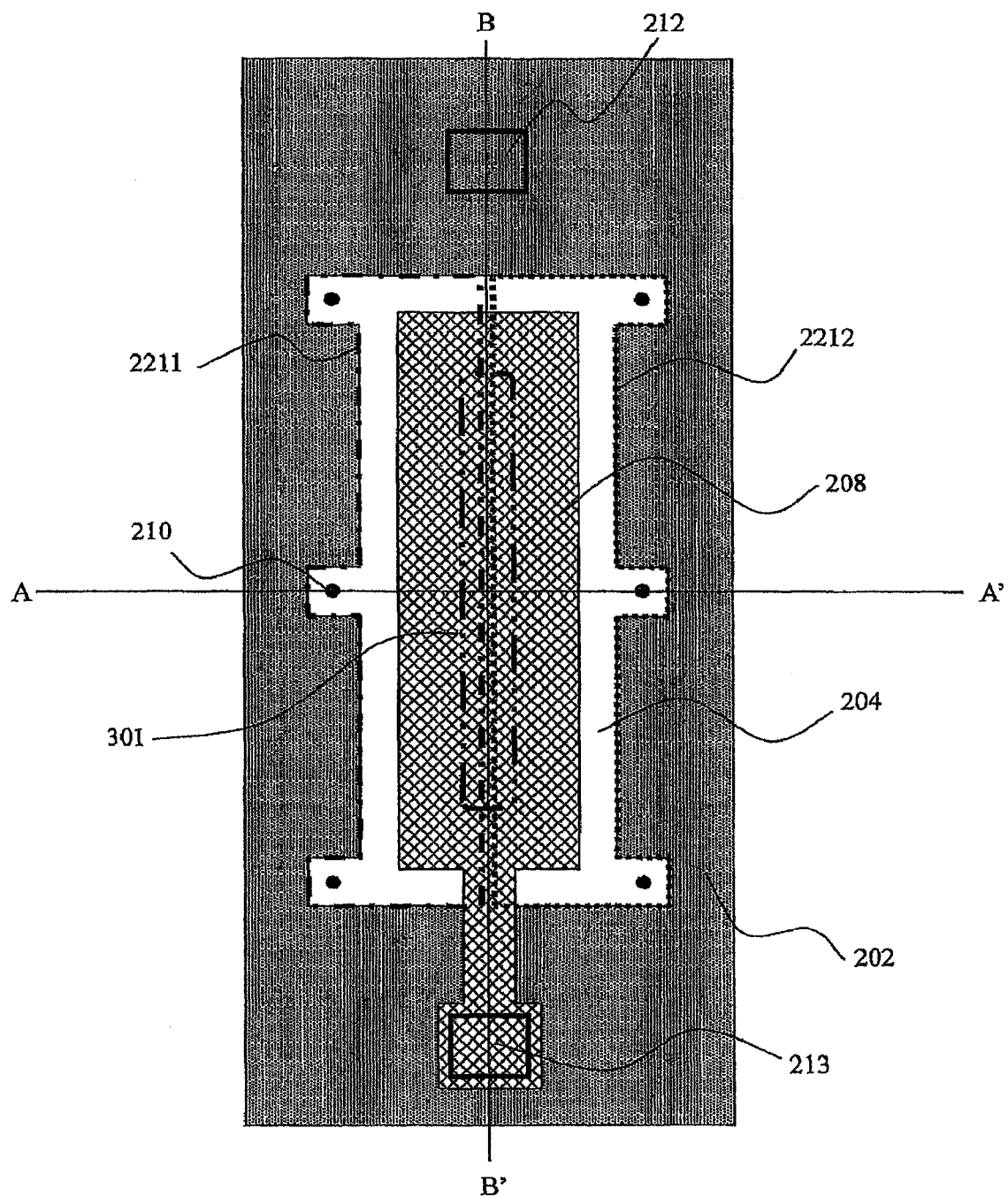
FIG. 19 is a top view of an ultrasonic transducer according to the first example of the embodiment 3, in which the hollow part has a rectangular shape as seen from above.

FIG. 19 is a top view of an example (first example) of ultrasonic transducer (CMUT) according to the embodiment 3. FIG. 19 shows a single CMUT cell as shown for the embodiments 1 and 2, but the shape of the cell of the embodiment 3 is different from those of the cells of the embodiments 1 and 2. The CMUT cell is constituted with the lower electrode 202, the hollow part 204 formed above the lower electrode 202, the upper electrode 208 disposed above the hollow part 204, and so forth. The etching hole 210 for forming the hollow part is communicated with a portion to become the hollow part 204. The opening 212 is provided so as to reach the lower electrode 202, and the opening 213 is provided so as to reach the upper electrode 208. Between the lower electrode 202 and the hollow part 204, the insulating film 203 consisting of a silicon oxide film is formed so as to cover the lower electrode 202, and between the upper electrode 208 and the hollow part 204, the insulating film 207 consisting of a silicon oxide film is formed so as to cover the hollow part 204 and the lower electrode 202. However, these insulating films are not shown in the drawing, in order to show the hollow part 204 and the lower electrode 202.

A conductive film 2211 is disposed so as to be exposed to the hollow part from the underside of the hollow part, and the shape thereof as seen from above is indicated with an alternate long and short dash line. Moreover, a conductive film 2212 is disposed so as to be exposed to the hollow part from the upside of the hollow part, and the shape thereof as seen from above is indicated with a dotted line. Further, the region 301 in which the surface below the hollow part 204 and the surface above the hollow part 204 contact with each other when the CMUT cell is driven is indicated with a two-dot chain line. Since the cell has a rectangular shape, the contact region 301 also has an approximately rectangular shape.

Figure 20:
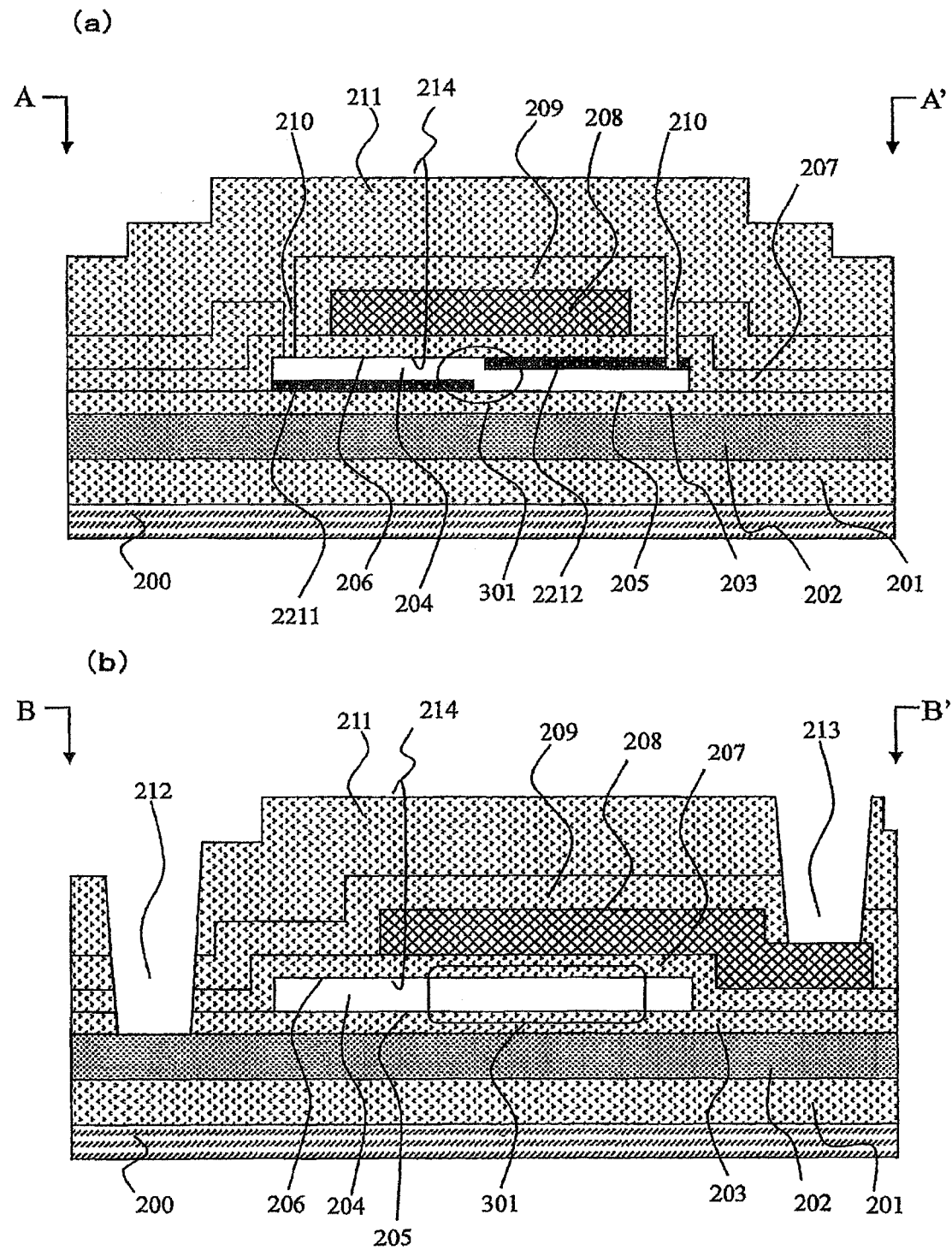
FIG. 20, (a) is a sectional view of the ultrasonic transducer shown in FIG. 19 along the line A-A' drawn in FIG. 19, and (b) is a sectional view of the same along the line B-B' drawn in FIG. 19.

FIG. 20, (a) is a sectional view along the line A-A' drawn in FIG. 19, and FIG. 20, (b) is a sectional view along the line B-B' drawn in FIG. 19. As shown in FIGS. 20, (a) and (b), the lower electrode 202 of the CMUT is disposed on the insulating film 201 consisting of a silicon oxide film and formed on the semiconductor substrate 200. Above the lower electrode 202, the hollow part 204 is formed through the insulating film 203 consisting of a silicon oxide film. Further, the conductive film 2211 is disposed so as to be exposed to the hollow part 204, and the conductive film 2212 is disposed so as to be exposed to the hollow part 204. The insulating film 207 consisting of a silicon oxide film is disposed so as to surround the conductive films 2211 and 2212, and the hollow part 204, and the upper electrode 208 is disposed on the insulating film 207. The insulating film 209 and the insulating film 211 consisting of silicon nitride films are disposed on the upper electrode 208. Further, the etching hole 210 is formed in the insulating film 207, the insulating film 209 and the conductive film 2212 so as to penetrate these films and filled with the insulating film 211. This etching hole 210 is formed for forming the hollow part 204. The membrane 214 according to the embodiment 3 is constituted with the insulating films 207, 209 and 211, the upper electrode 208 and the conductive film 2212.

The embodiment 3 is characterized in that both the conductive film 2211 disposed on the side of the surface 205 below the hollow part 204 and the conductive film 2212 disposed on the side of the surface 206 above the hollow part 204 are disposed so that they are not overlap with each other in the region 301 in which the surface 205 below the hollow part and the surface 206 above the hollow part contact with each other as seen from above, when the CMUT cell is driven, and that the contact region 301 and both the conductive films 2211 and 2212 overlap with each other as seen from above. According to the embodiment 3, for example, in a vertical section including the hollow part (FIG. 20, (a)), the conductive film 2211 is disposed on the left of the center of the hollow part, and the conductive film 2212 is disposed on the right of the center of the hollow part, and parts of these conductive films extend to the contact region 301.

Figure 21:
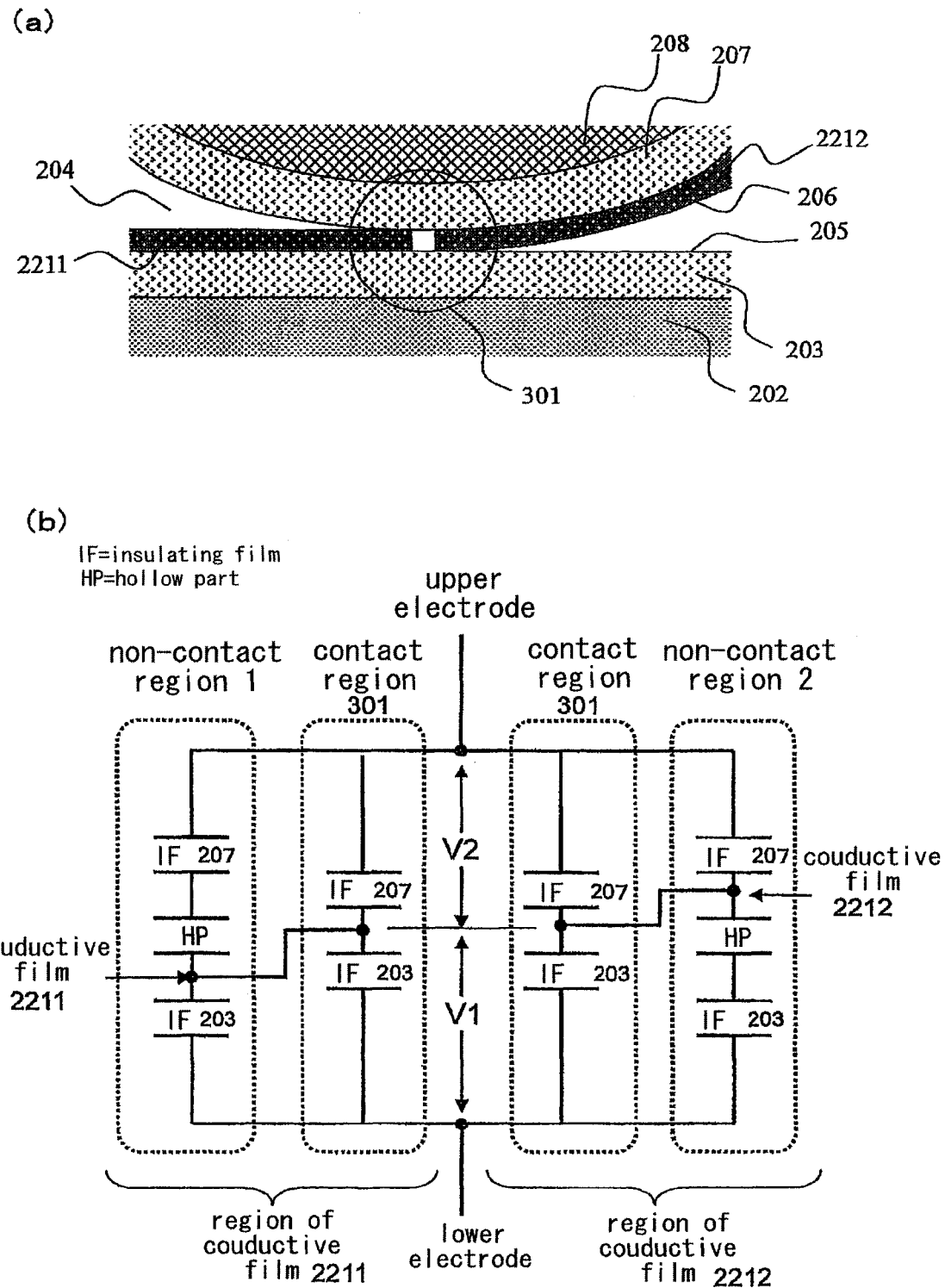
FIG. 21, (a) is an enlarged view of a contact region of the ultrasonic transducer according to the embodiment 3 in a state that the surfaces above and below the hollow part contact with each other in that region when the transducer is driven, and (b) shows an equivalent circuit diagram for the ultrasonic transducer according to the embodiment 3 in a state that the surfaces above and below the hollow part contact with each other when the transducer is driven.

FIGS. 21, (a) and (b) are an enlarged view of the contact region 301 in a state that the surface 205 below the hollow part 204 and the surface 206 above the hollow part 204 contact with each other when the CMUT cell according to the embodiment 3 is driven, and an equivalent circuit diagram, respectively. It is not necessarily required that both the conductive films 2211 and 2212 are exposed to the hollow part 204, and an insulating film may be disposed between the conductive films and the hollow part. However, for convenience of explanation, explanation will be made with reference to a structure in which the conductive films are exposed to the hollow part, like the embodiments 1 and 2. Hereafter, effects of the embodiment 3 will be explained.

When the conductive film 2211 exposed to the hollow part from the side of the surface 205 below the hollow part 204 and the conductive film 2212 exposed to the hollow part from the side of the surface 206 above the hollow part 204 are disposed so that the both overlap with the contact region 301 as seen from above as shown in FIGS. 19 and 20, both the conductive films 2211 and 2212 has the same structure in the contact region, i.e., they are between the lower electrode 202 and the upper electrode 208 through the insulating films 203 and 207, when the CMUT cell is driven. In such a case, potentials of the conductive films 2211 and 2212 are those obtained by distributing the voltage applied between the lower electrode 202 and the upper electrode 208 according to the capacitances of the insulating films 203 and 207 as shown in FIG. 21, (b), and as a result, the conductive films 2211 and 2212 have the same potential V1. This is because the conductive films 2211 and 2212 are electrically isolated conductive films.

At this time, in the region of the conductive film 2211 shown in FIG. 21, (*b*), electric field intensities in the contact region 301 and the region other than the contact region of the insulating film 203 between the conductive film 2211 and the lower electrode 202 become equivalent, thus concentration of the leak electric currents in the contact region 301 can be suppressed, and accumulation of electrical charge in the insulating film 203 and degradation of dielectric strength thereof can be suppressed. On the other hand, electric field intensity of the insulating film 207 in the contact region 301 corresponds to a value obtained by dividing V2 with thickness of the insulating film 207, and is higher than that of the non-contact region other than the contact region 301. However, since the conductive film 2212 having the same electric potential as that of the conductive film 2211 is also disposed, in the region of the conductive film 2212, electric field intensity of the insulating film 207 in the non-contact region other than the contact region 301 also corresponds to a value obtained by dividing V2 with thickness of the insulating film 207, which is equal to the electric field intensity of the insulating film 207 in the contact region in the region of conductive film 2211. As a result, concentration of the leak electric currents in the insulating film 207 in the contact region can be suppressed.

Also in the region of the conductive film 2212, electric field intensities of the contact region 301 and the region other than the contact region of the insulating film 207 between the conductive film 2212 and the upper electrode 208 become equivalent, thus concentration of the leak electric currents in the contact region 301 can be suppressed, and accumulation of electrical charge in the insulating film 207 and degradation of dielectric strength thereof can be suppressed, as in the aforementioned embodiment 2. On the other hand, electric field intensity of the insulating film 203 in the contact region 301 corresponds to a value obtained by dividing V1 with thickness of the insulating film 203, and is higher than that of the non-contact region other than the contact region 301. However, since the conductive film 2211 having the same electric potential as that of the conductive film 2212 is also disposed, electric field intensity of the insulating film 203 in the non-contact region other than the contact region 301 in the region of the conductive film 2211 also corresponds to a value obtained by dividing V1 with thickness of the insulating film 203, which is equal to the electric field intensity of the insulating film 207 in the contact region in the region of conductive film 2212. As a result, concentration of the leak electric currents in the insulating film 203 of the contact region can be suppressed.

That is, even if the surfaces above and below the hollow part contact with each other, the conductive film 2212 exerts an electric field attenuating function for the insulating film 207 with respect to the conductive film 2211, and the conductive film 2211 exerts an electric field attenuating function for the insulating film 203 with respect to the conductive film 2212. Therefore, concentration of the leak electric currents in the insulating films 203 and 207 in the contact region 301 can be suppressed, and accumulation of electrical charge in the insulating films 203 and 207 and degradation of dielectric strength thereof can be suppressed.

Figure 22:
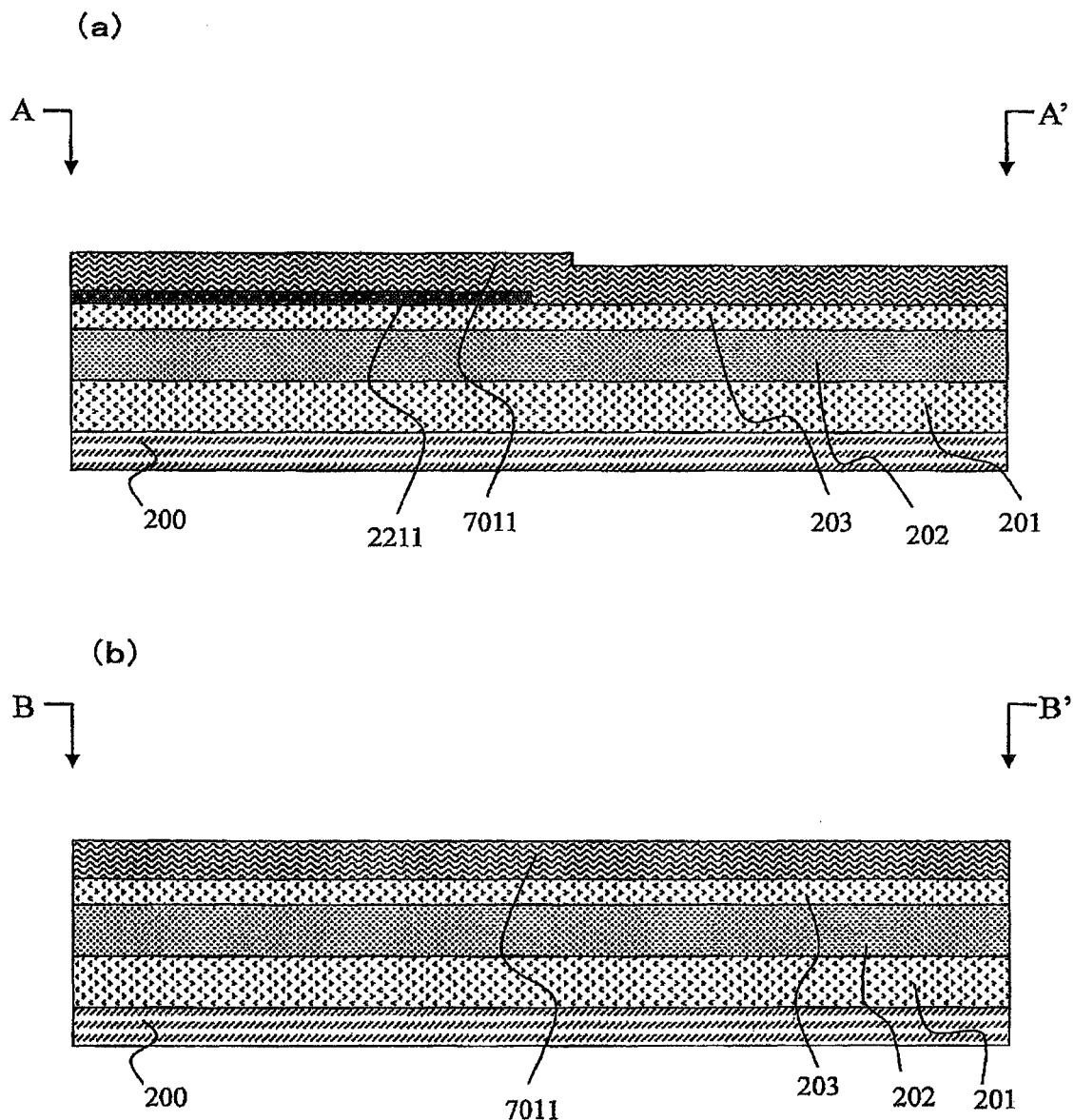
FIGS. 22, (a) and (b) are sectional views for explaining a manufacturing step of the ultrasonic transducer shown in FIG. 19 along the lines A-A' and B-B' drawn in FIG. 19, respectively.
Figure 28:
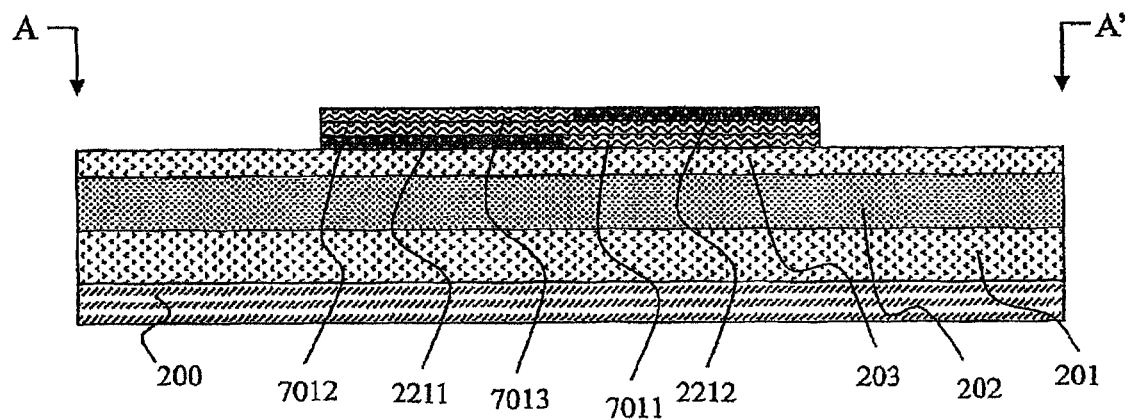
FIGS. 28, (a) and (b) are sectional views for explaining a manufacturing step of the ultrasonic transducer following the step shown in FIGS. 27, (a) and (b).
Figure 28:
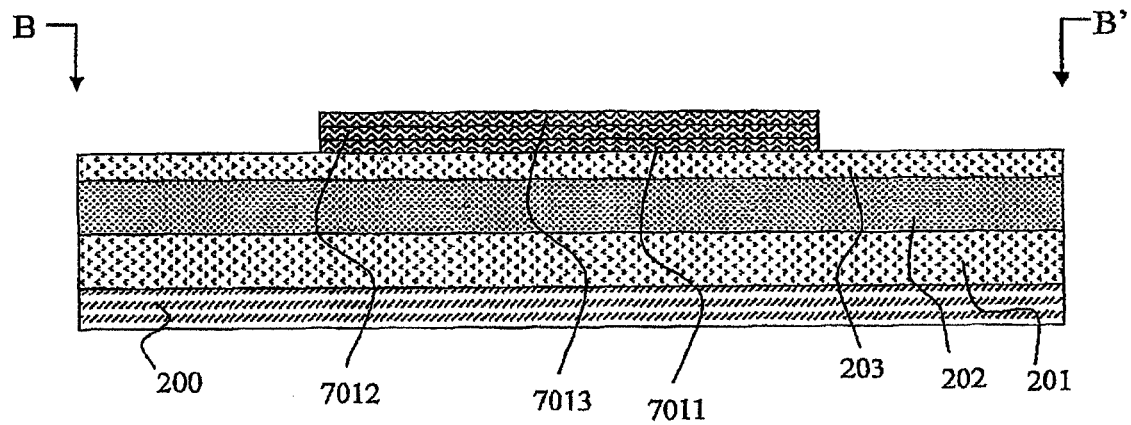

Next, the method for producing the CMUT cell described as the embodiment 3 will be explained with reference to the drawings. The steps up to the formation of the insulating film 203 are the same as those shown in FIGS. 5 and 6 explained for the aforementioned embodiment 1. FIG. 22, (*a*) to FIG. 28, (*a*) show sections along the line A-A' drawn in FIG. 19, and FIG. 22, (*b*) to FIG. 28, (*b*) show sections along the line B-B' drawn in FIG. 19.

Figure 23:
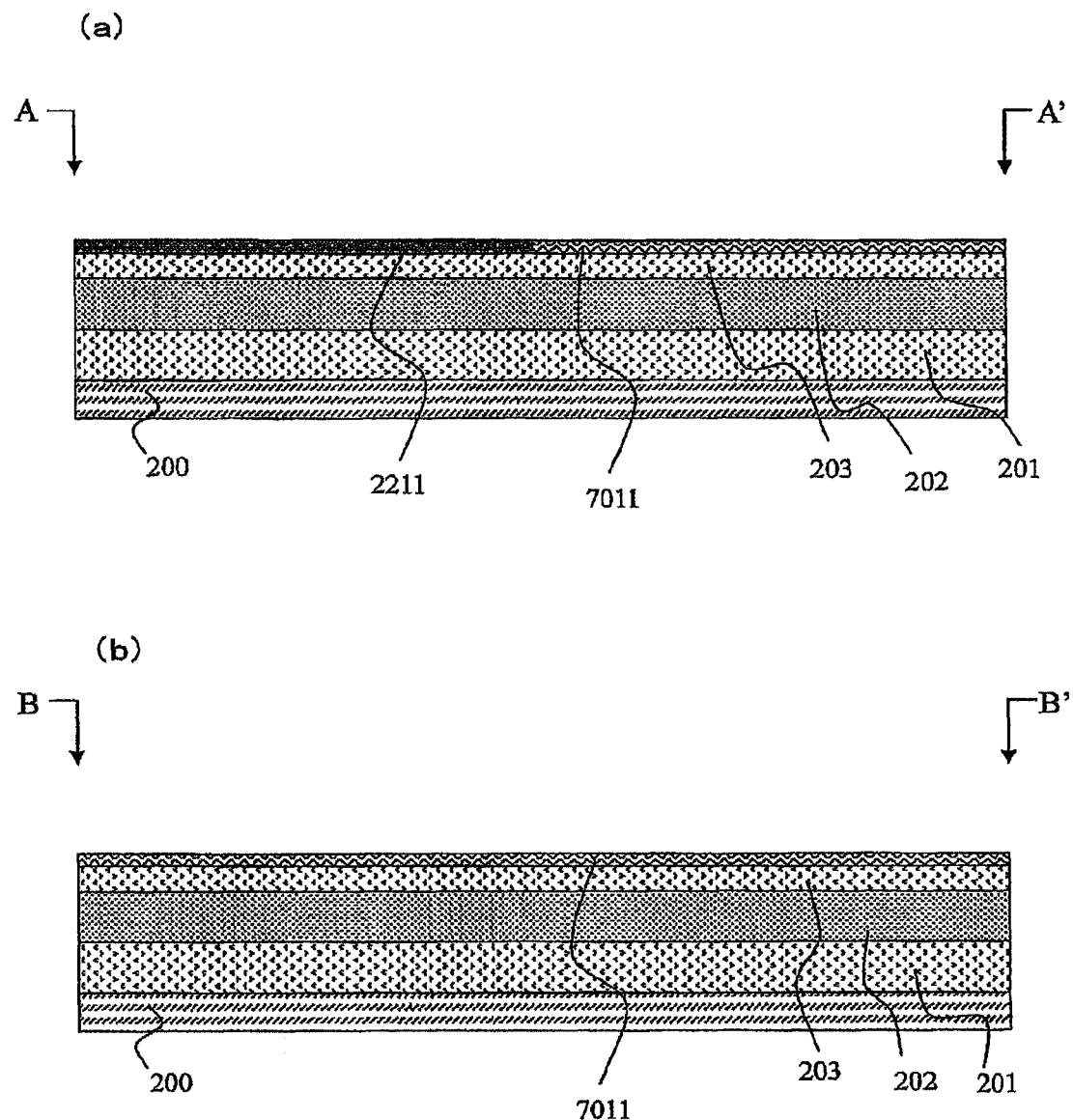
FIGS. 23, (a) and (b) are sectional views for explaining a manufacturing step of the ultrasonic transducer following the step shown in FIGS. 22, (a) and (b).
Figure 24:
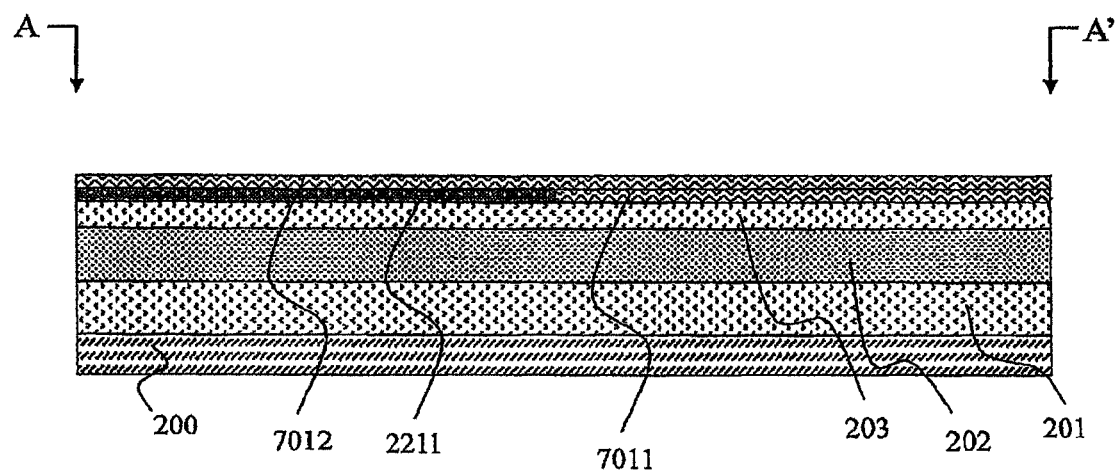
FIGS. 24, (a) and (b) are sectional views for explaining a manufacturing step of the ultrasonic transducer following the step shown in FIGS. 23, (a) and (b).
Figure 24:
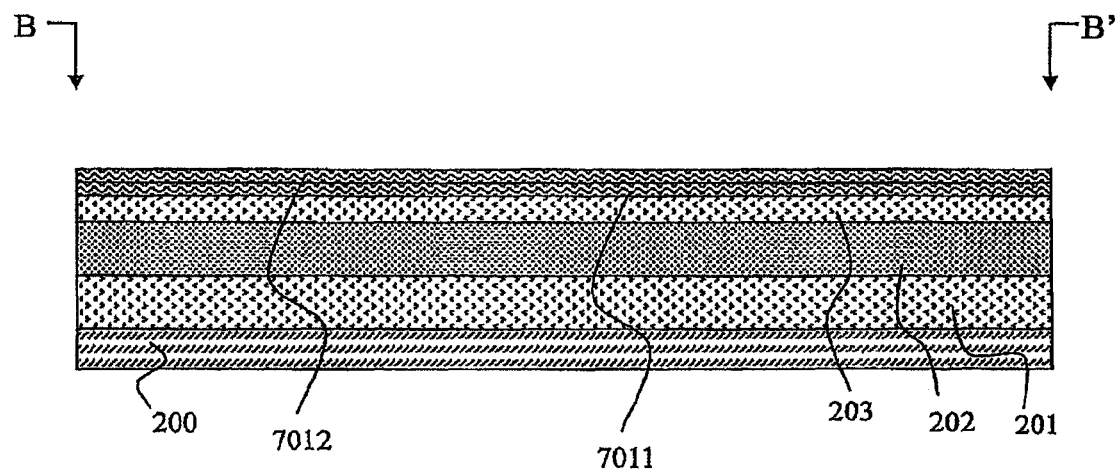

First, as shown in FIGS. 22(*a*) and (*b*), an aluminum alloy film serving as the electrically isolated conductive film 2211 is deposited in 50 nm thickness on the upper surface of the insulating film 203 by the sputtering method, and patterning is performed by photolithography and dry etching techniques. Then, a polycrystalline silicon film 7011 is deposited in 150 nm thickness by the plasma-CVD method. Then, as shown in FIGS. 23, (*a*) and (*b*), the polycrystalline silicon film 7011 is polished by 100 nm by the CMP method (Chemical Mechanical Polishing) to expose the surface of the aluminum alloy film 2211 serving as the electrically isolated conductive film 2211. Then, as shown in FIGS. 24, (*a*) and (*b*), a polycrystalline silicon film 7012 is deposited in 50 nm thickness by the plasma-CVD method.

Figure 25:
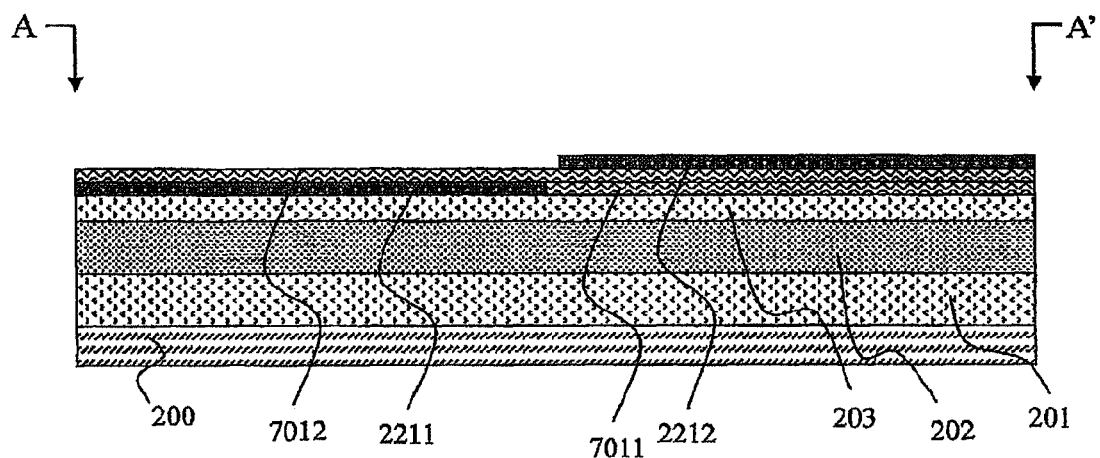
FIGS. 25, (a) and (b) are sectional views for explaining a manufacturing step of the ultrasonic transducer following the step shown in FIGS. 24, (a) and (b).
Figure 25:
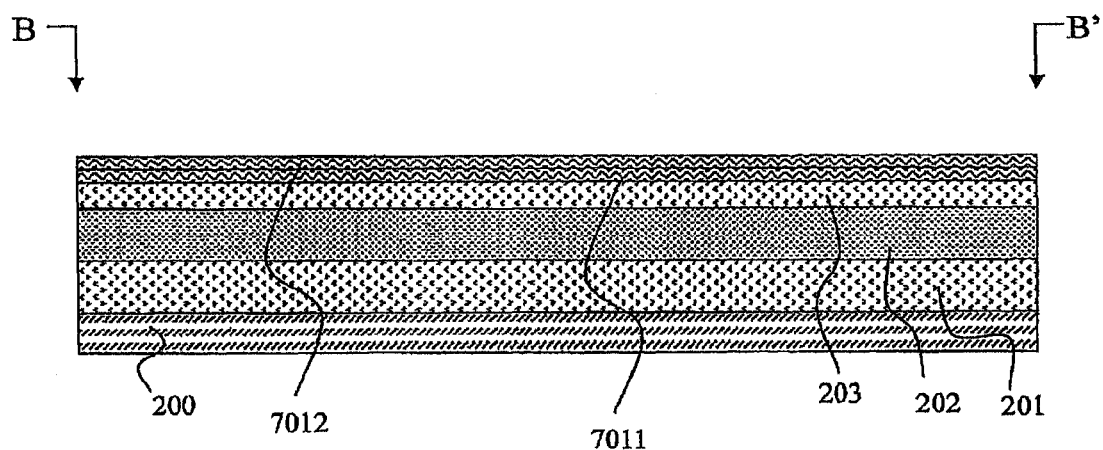

Then, an aluminum alloy film serving as the conductive film 2212 is deposited in 50 nm thickness on the upper surface of the polycrystalline silicon film 7012 and the aluminum alloy film 2211 by the sputtering method, and patterning is performed by the photolithography and dry etching techniques (FIGS. 25, (*a*) and (*b*)). This patterning is performed so that the conductive films 2211 and 2212 do not overlap with each other as seen from above, and they overlap with the region in which the surfaces above and below the hollow part formed by the following steps contact with each other as seen from above when the CMUT cell is driven.

Figure 26:
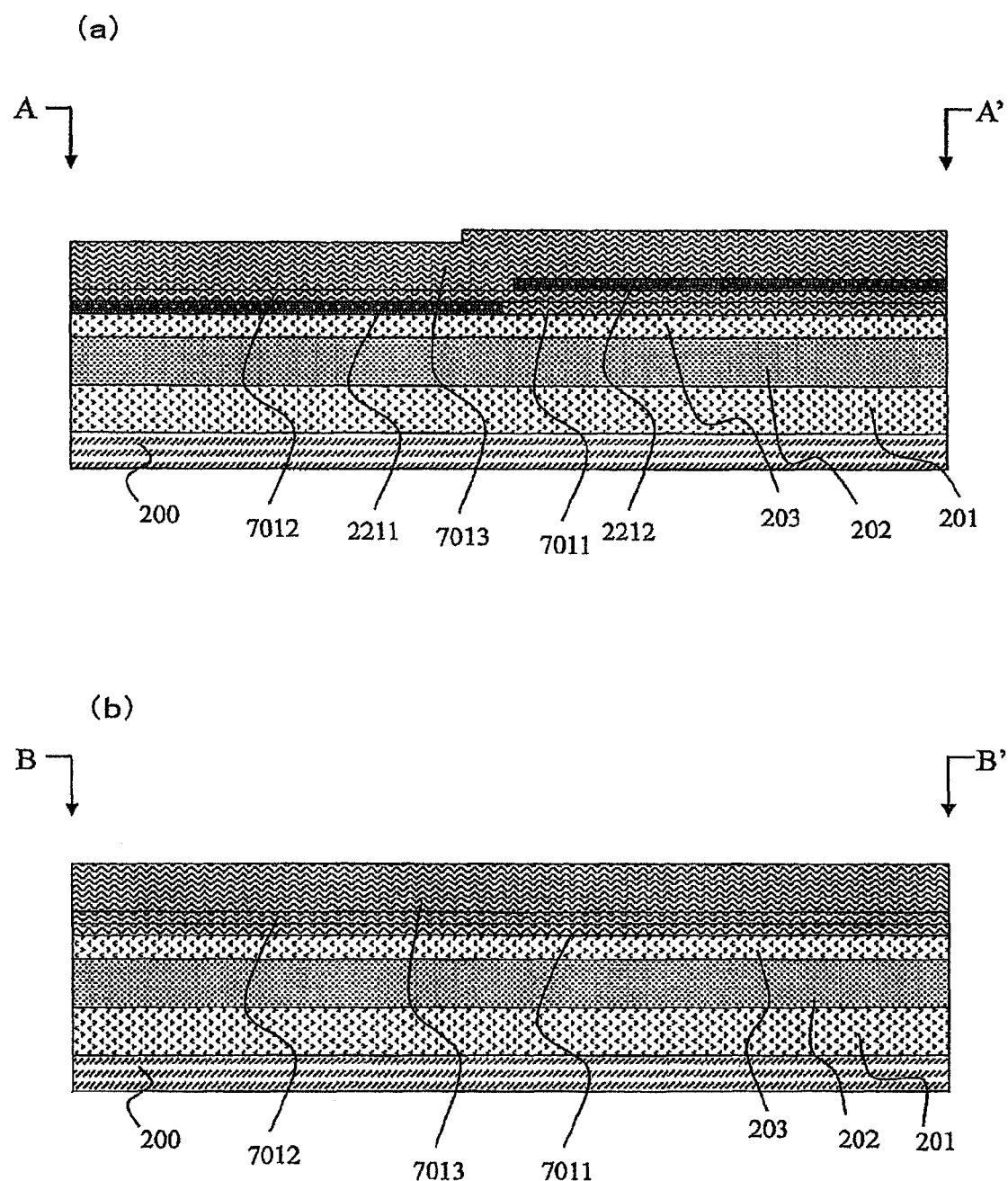
FIGS. 26, (a) and (b) are sectional views for explaining a manufacturing step of the ultrasonic transducer following the step shown in FIGS. 25, (a) and (b).
Figure 27:
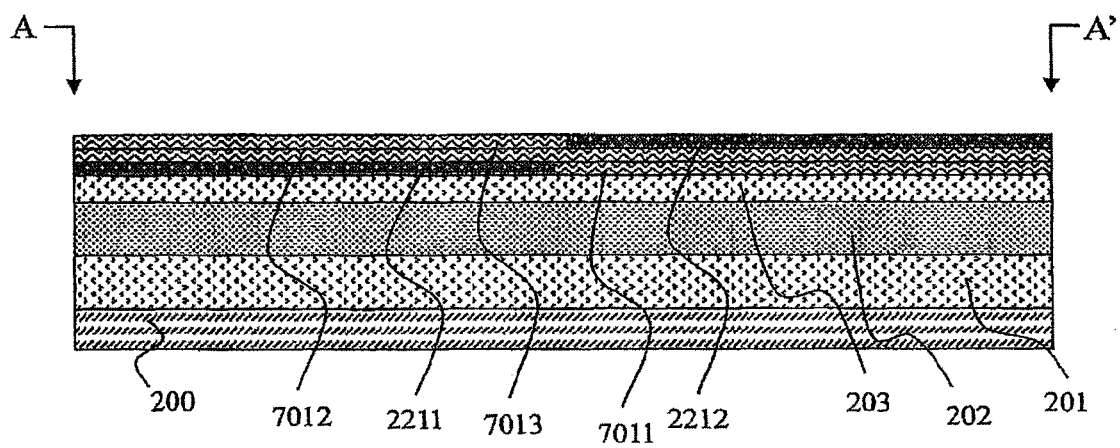
FIGS. 27, (a) and (b) are sectional views for explaining a manufacturing step of the ultrasonic transducer following the step shown in FIGS. 26, (a) and (b).
Figure 27:
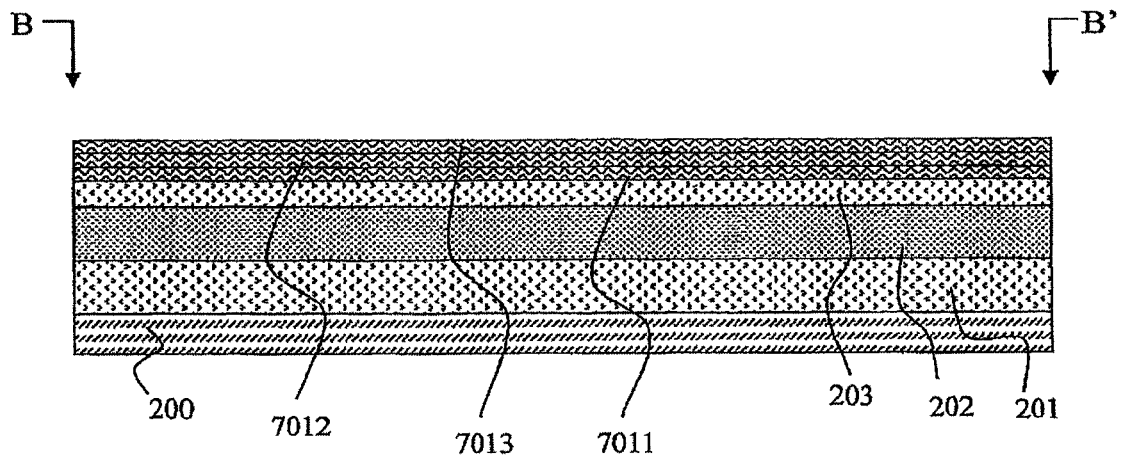

Then, as shown in FIGS. 26, (*a*) and (*b*), a polycrystalline silicon film 7013 is deposited in 150 nm thickness by the plasma-CVD method. Then, as shown in FIGS. 27, (*a*) and (*b*), the polycrystalline silicon film 7013 is polished by 100 nm by the CMP method to expose the surface of the aluminum alloy film serving as the conductive film 2212. Then, patterning is performed for the aluminum alloy films 2211 and 2212 and the polycrystalline silicon films 7011, 7012, and 7013 by the photolithography and dry etching techniques to form a sacrificial layer consisting of the conductive films 2211 and 2212 and the polycrystalline silicon films 7011, 7012, and 7013 on the insulating film 203 (FIGS. 28, (*a*) and (*b*)). The hollow part is formed at the position of the sacrificial layer in a subsequent step. As for the following steps, the CMUT cell of this embodiment 3 shown in FIGS. 19 and 20 can be produced by the same steps as those shown in FIGS. 8 to 14 explained for the embodiment 1.

Figure 29:
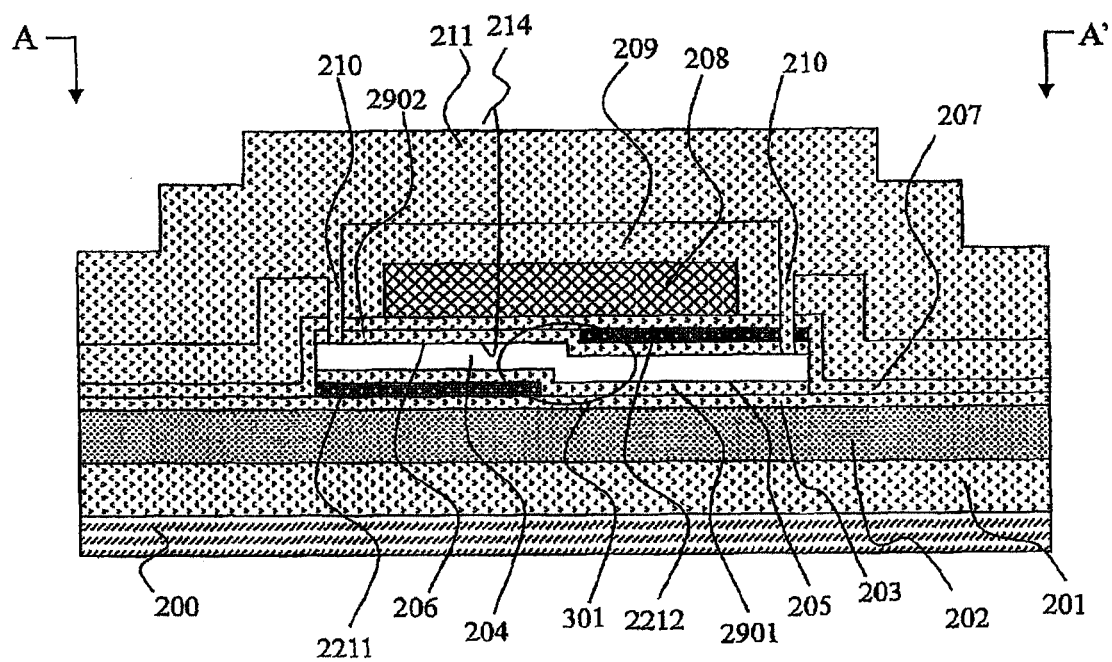
FIG. 29 includes drawings showing an ultrasonic transducer according to the second example of the embodiment 3, FIG. 29, (a) is a sectional view along the line A-A' drawn in FIG. 19, and (b) is a sectional view along the line B-B' drawn in FIG. 19.
Figure 29:
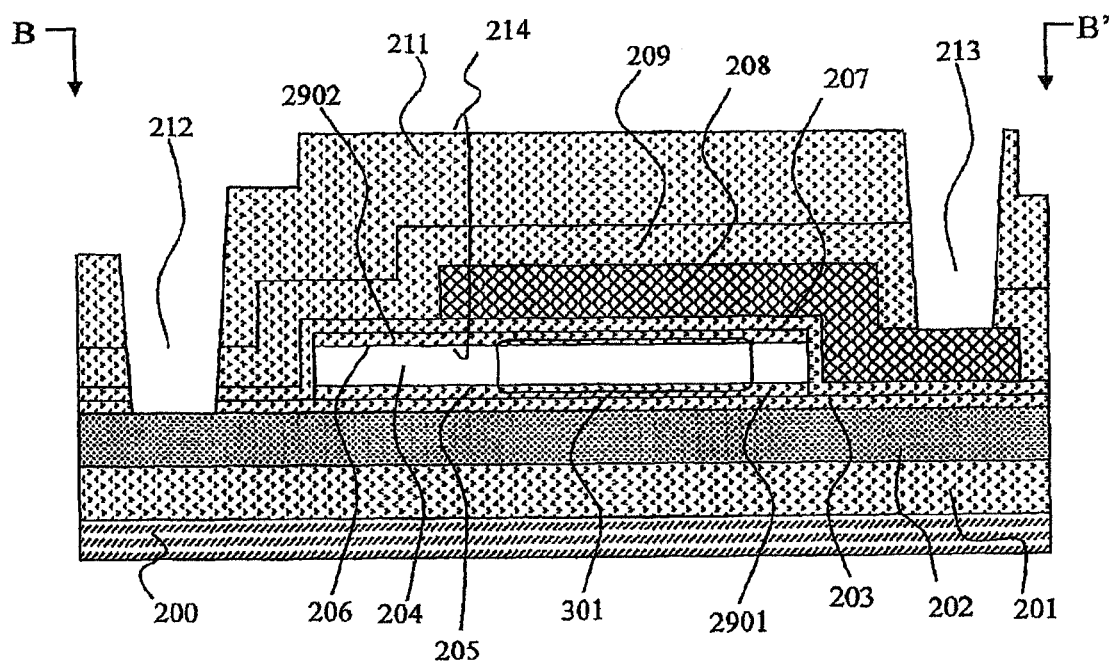

FIG. 29 includes sectional views of the ultrasonic transducer according to the second example of the embodiment 3. The top view of the ultrasonic transducer of this example is the same as that shown in FIG. 19. The difference from the first example is that the conductive films 2211 and 2212 are in contact with the hollow part 204 through the insulating films 2901 and 2902, respectively, and the other structures are the same. Even with such a configuration, concentration of the leak electric currents in the contact region 301 can be suppressed, and accumulation of electrical charge in the insulating films 203, 2901, 207, and 2902, and degradation of dielectric strength thereof can be reduced.

Figure 30:
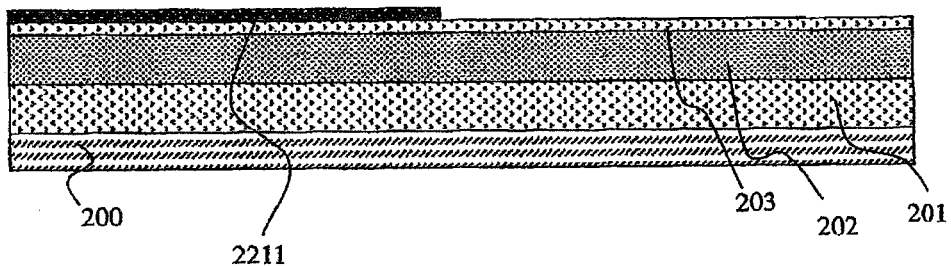
FIGS. 30, (a) and (b) are sectional views for explaining a manufacturing step of the ultrasonic transducer shown in FIG. 29.
Figure 30:
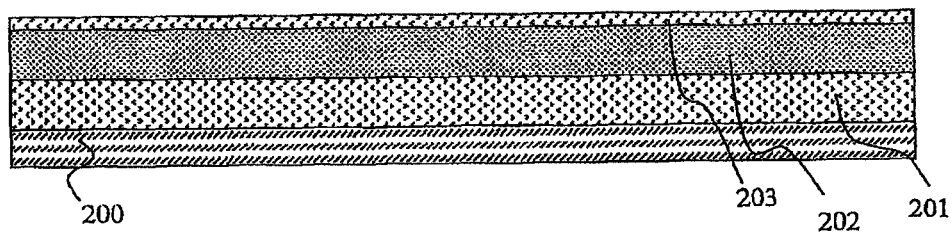
Figure 31:
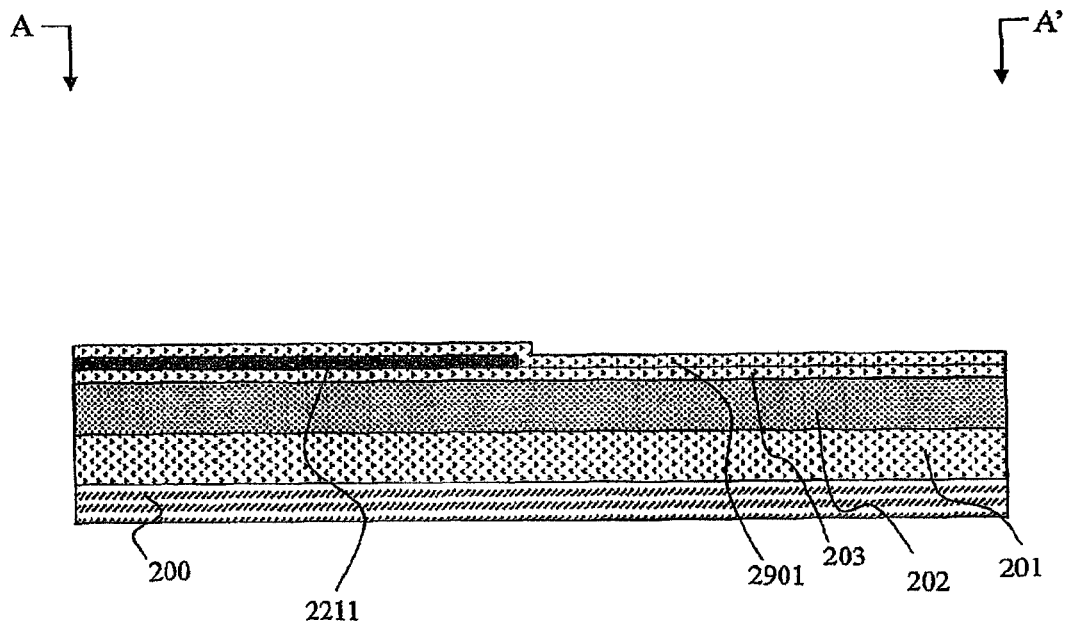
FIGS. 31, (a) and (b) are sectional views for explaining a manufacturing step of the ultrasonic transducer following the step shown in FIGS. 30, (a) and (b).
Figure 31:
Figure 32:
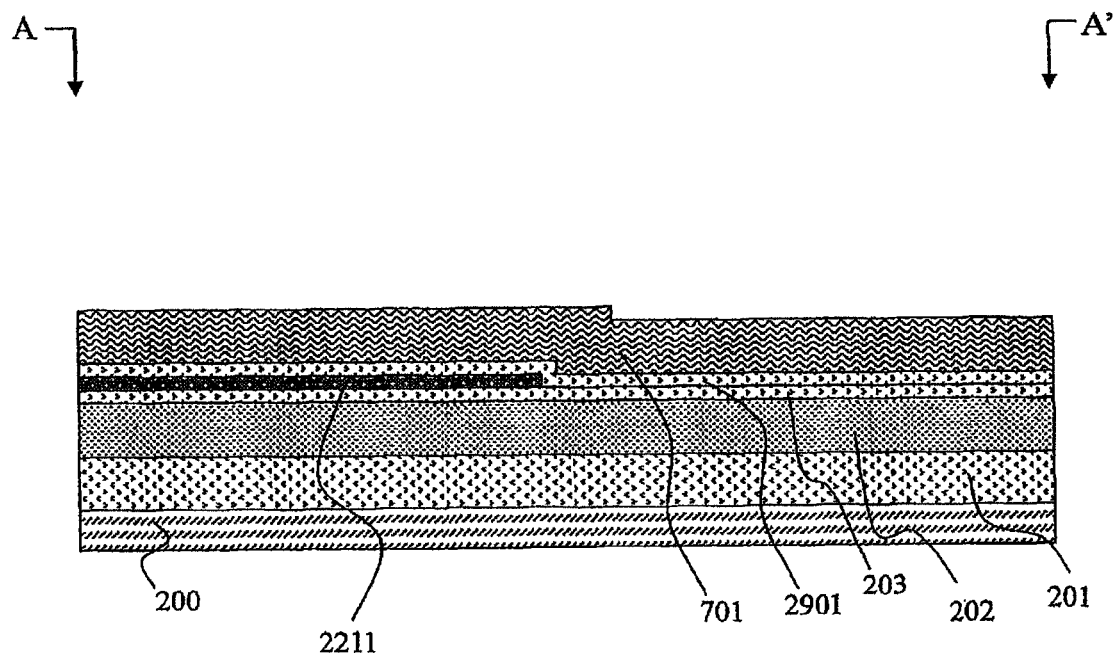
FIGS. 32, (a) and (b) are sectional views for explaining a manufacturing step of the ultrasonic transducer following the step shown in FIGS. 31, (a) and (b).
Figure 32:
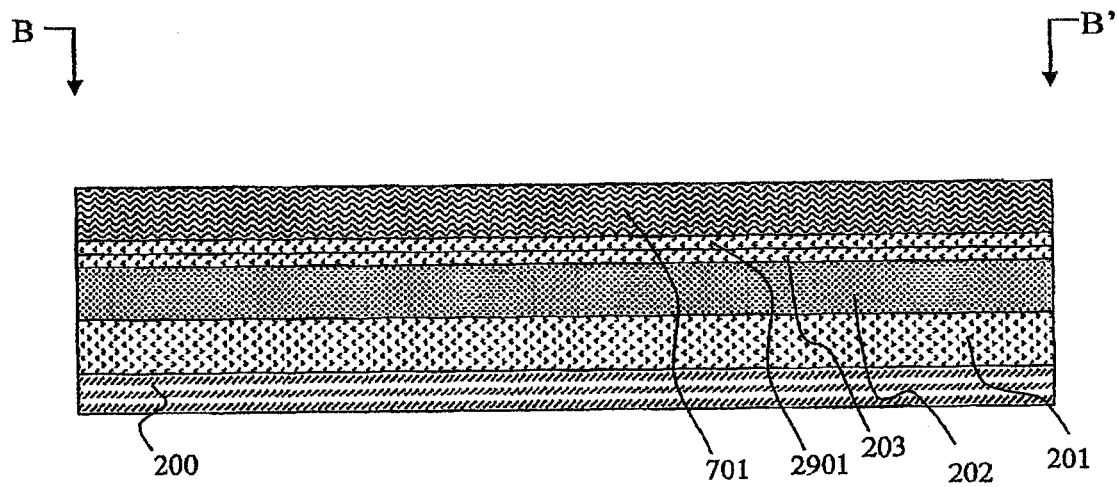

The method for producing the ultrasonic transducer shown in FIG. 29 is shown in FIGS. 30 to 39. The steps up to the formation of the insulating film 203 are the same as those shown in FIGS. 5 and 6 explained for the aforementioned embodiment 1. In this case, thickness of the insulating film consisting of a silicon oxide film between the upper and lower electrodes is set to be the same as that of the first example of this embodiment 3, i.e., 50 nm. First, as shown in FIGS. 30, (*a*) and (*b*), an aluminum alloy film serving as the conductive film 2211 is deposited in 50 nm thickness on the upper surface of the insulating film 203 by the sputtering method, and patterning is performed by the photolithography and dry etching techniques. Then, an insulating film consisting of a silicon oxide film is deposited in 50 nm thickness by the plasma-CVD method (FIGS. 31, (a) and (b)).

Figure 33:
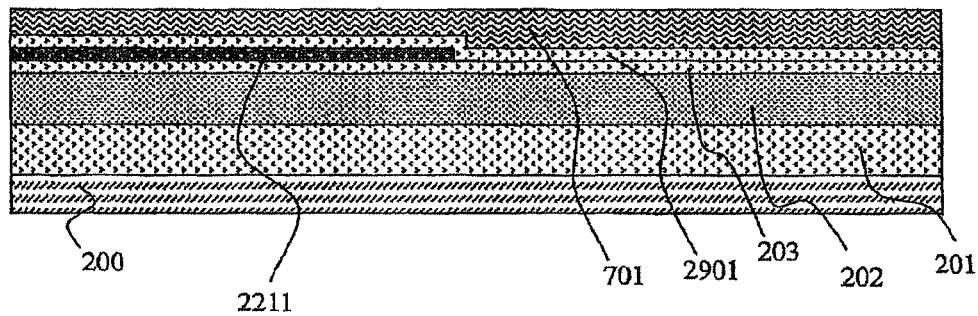
FIGS. 33, (a) and (b) are sectional views for explaining a manufacturing step of the ultrasonic transducer following the step shown in FIGS. 32, (a) and (b).
Figure 33:
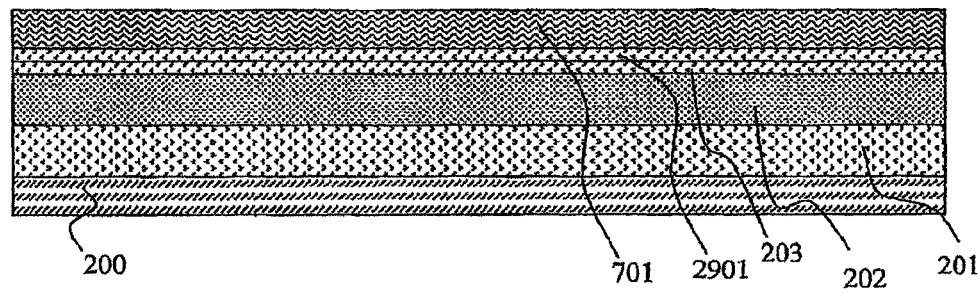
Figure 34:
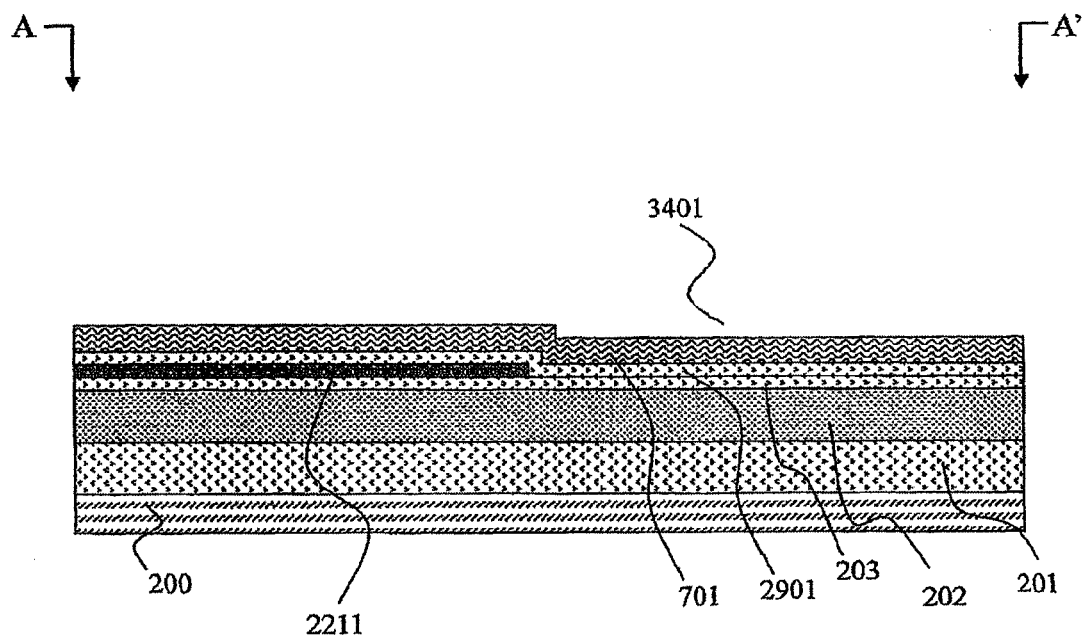
FIGS. 34, (a) and (b) are sectional views for explaining a manufacturing step of the ultrasonic transducer following the step shown in FIGS. 33, (a) and (b).
Figure 34:
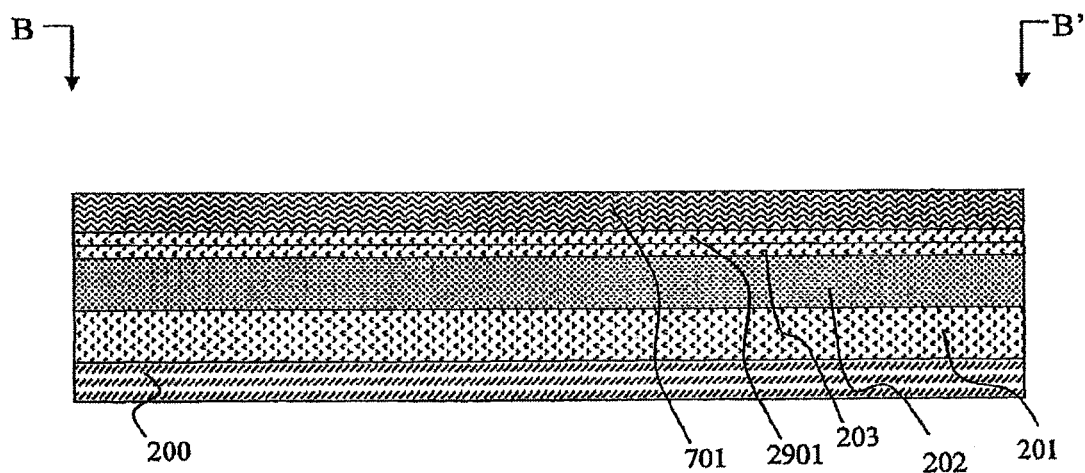

Then, as shown in FIGS. 32(a) and (b), a polycrystalline silicon film 701 is deposited in 200 nm thickness by the plasma-CVD method, and the polycrystalline silicon film 701 is polished by 100 nm by the CMP method (FIGS. 33, (a) and (b)). Then, as shown in FIGS. 34, (a) and (b), patterning is performed for the polycrystalline silicon film 701 by the photolithography and dry etching techniques to form a pit 3401 of 50 nm.

Figure 35:
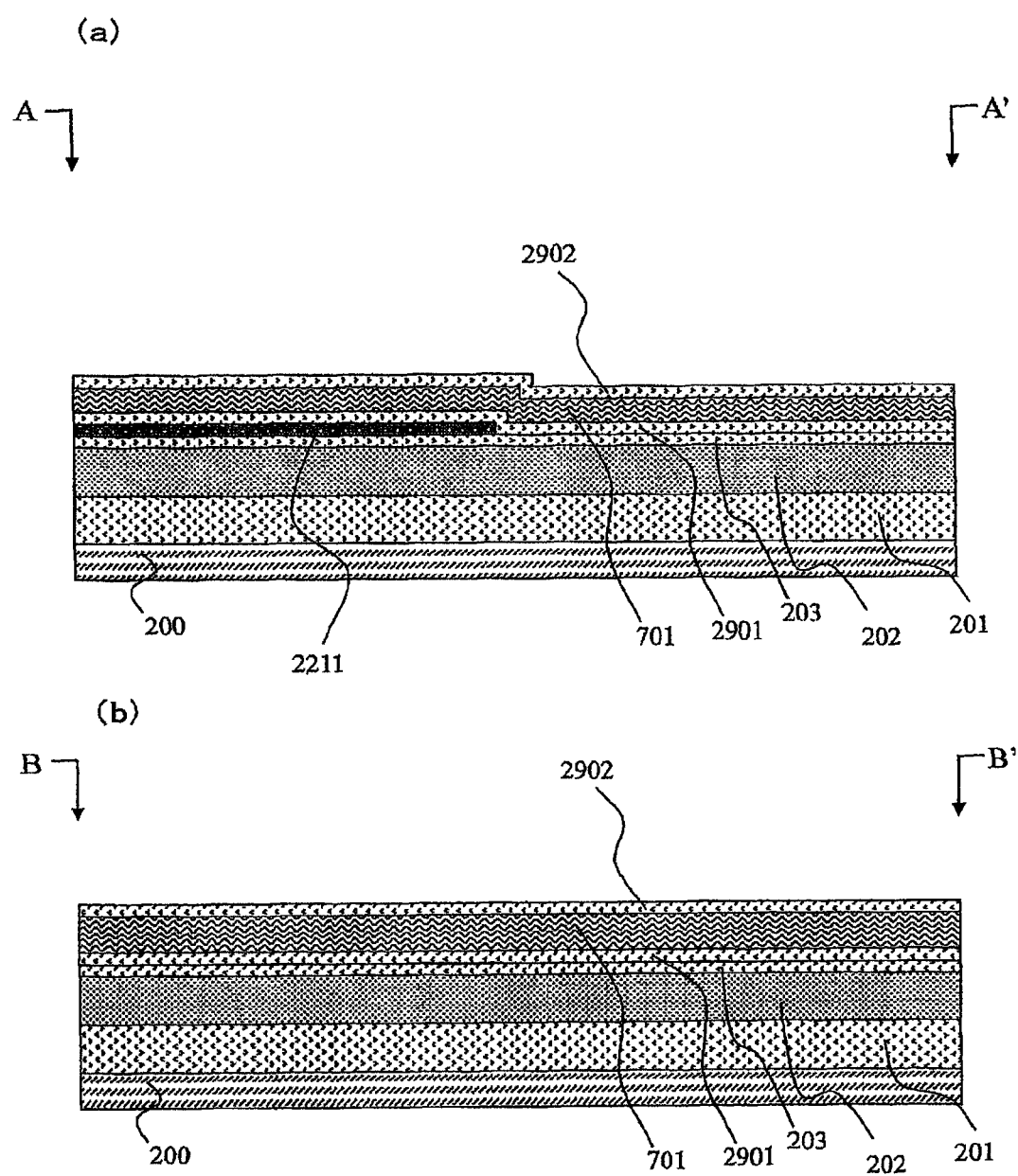
FIGS. 35, (a) and (b) are sectional views for explaining a manufacturing step of the ultrasonic transducer following the step shown in FIGS. 34, (a) and (b).
Figure 36:
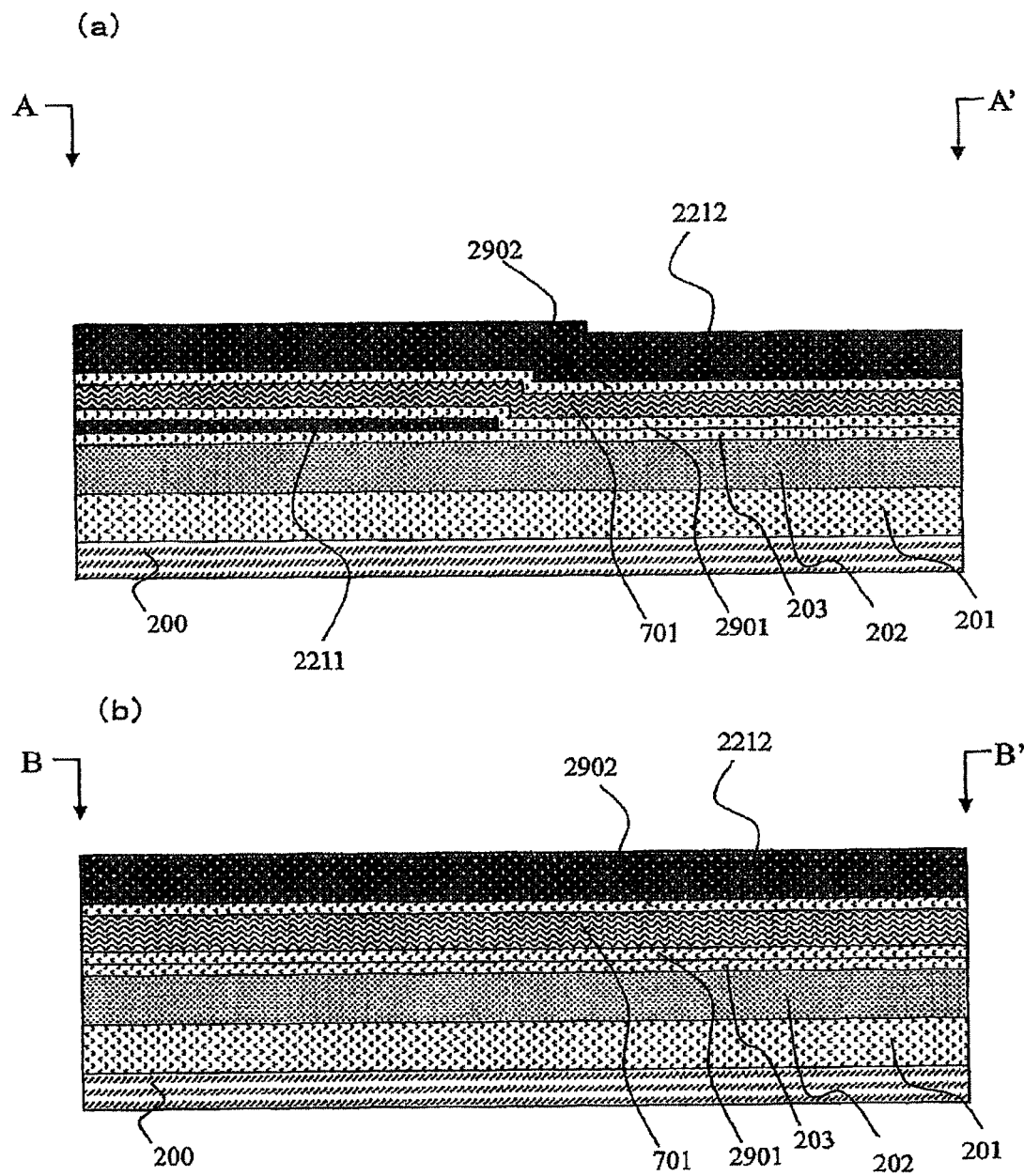
FIGS. 36, (a) and (b) are sectional views for explaining a manufacturing step of the ultrasonic transducer following the step shown in FIGS. 35, (a) and (b).
Figure 37:
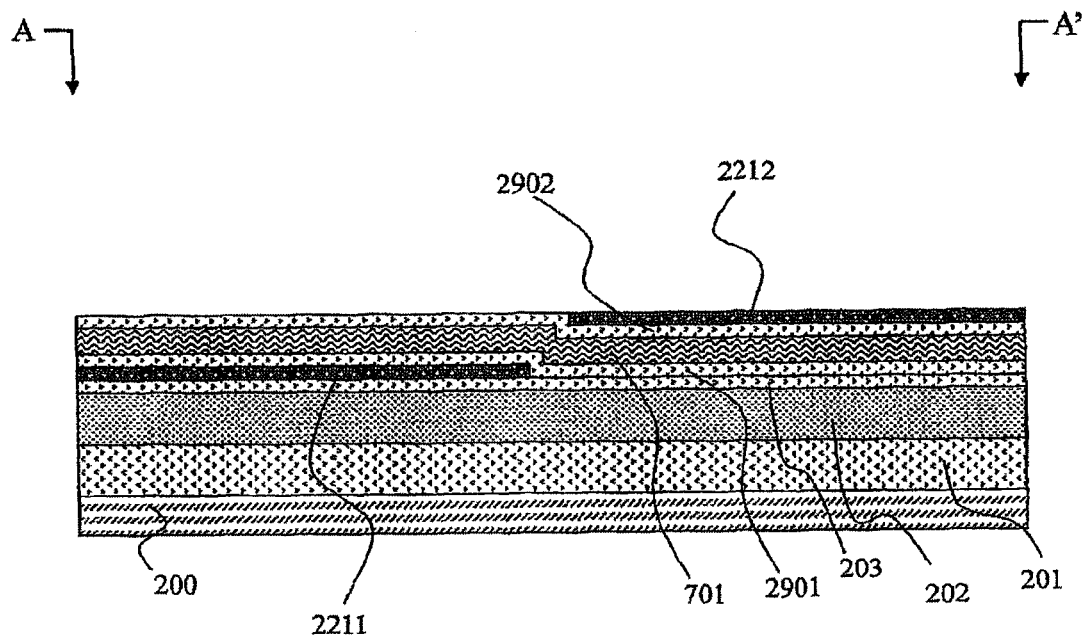
FIGS. 37, (a) and (b) are sectional views for explaining a manufacturing step of the ultrasonic transducer following the step shown in FIGS. 36, (a) and (b).
Figure 37:
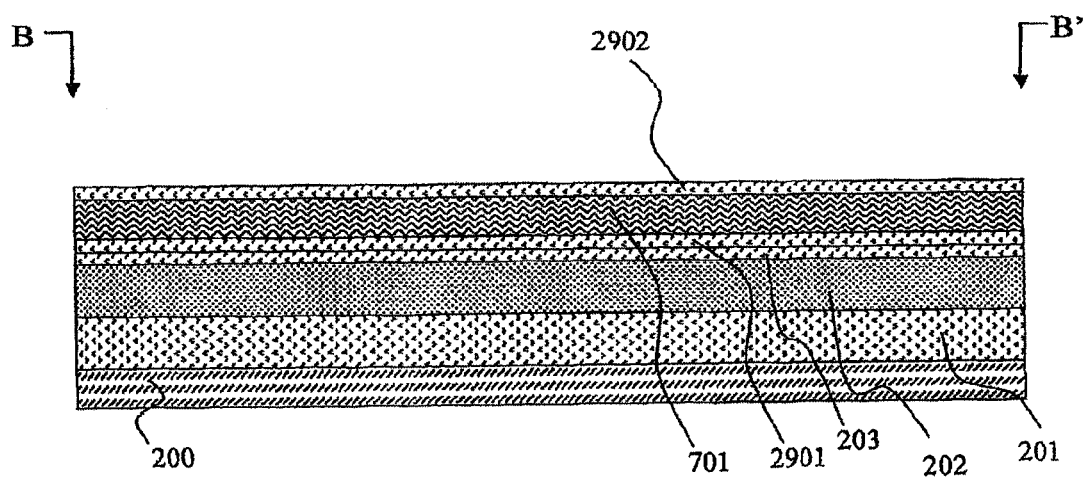

Then, as shown in FIGS. 35, (a) and (b), an insulating film 2902 consisting of a silicon oxide film is deposited by the plasma-CVD method so as to cover the polycrystalline silicon film 701. At the time of this deposition, the insulating film 2902 also deposits in the pit 3401. Then, an aluminum alloy film serving as the conductive film 2212 is deposited in 200 nm thickness on the upper surface of the insulating film 2902 by the sputtering method (FIGS. 36, (a) and (b)), and polished by 150 nm by the CMP method to expose the surface of the insulating film 2902 (FIGS. 37, (a) and (b)).

Figure 38:
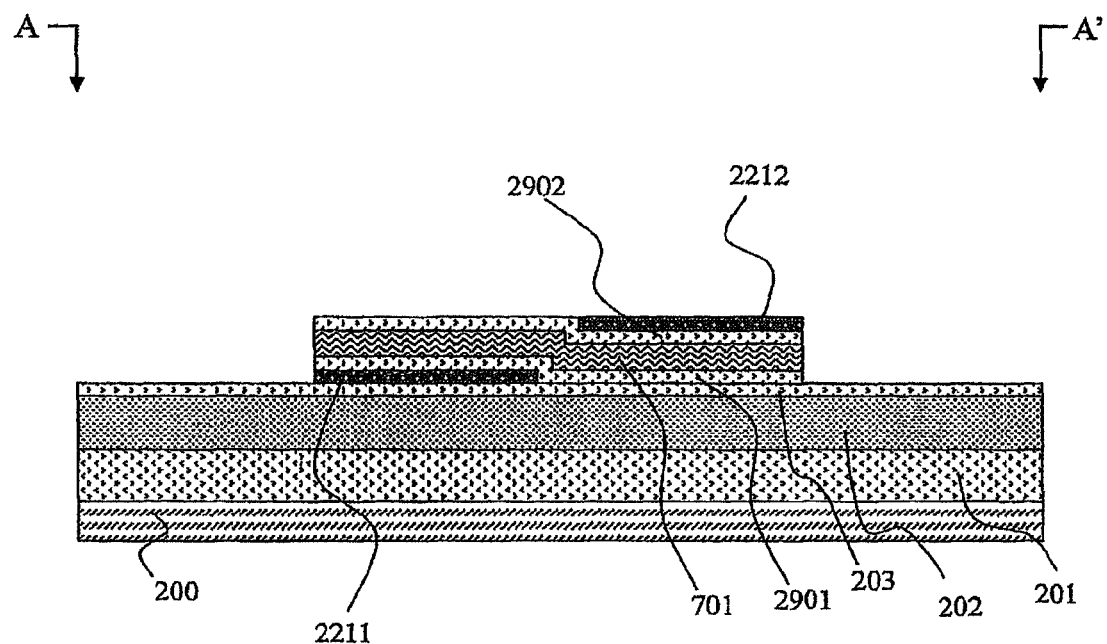
FIGS. 38, (a) and (b) are sectional views for explaining a manufacturing step of the ultrasonic transducer following the step shown in FIGS. 37, (a) and (b).
Figure 38:
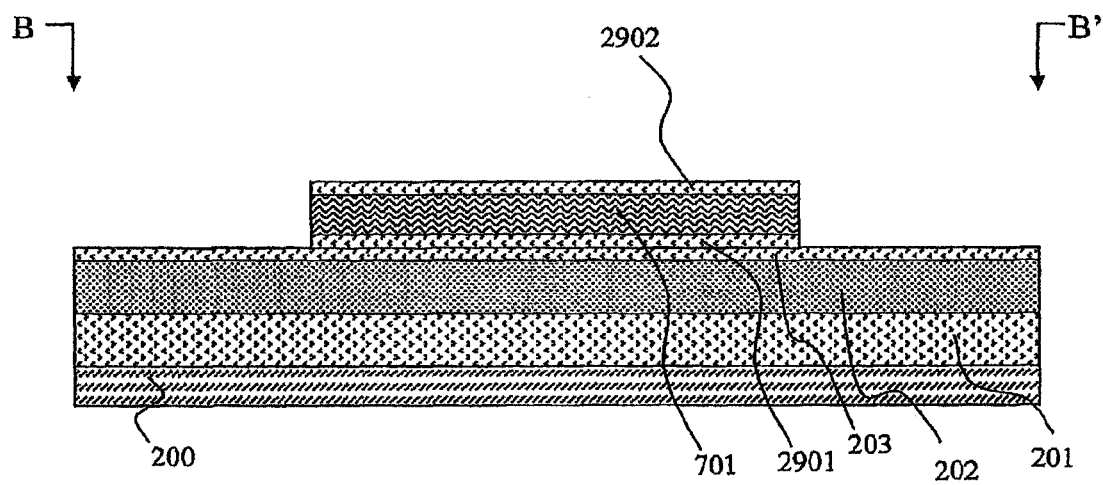
Figure 39:
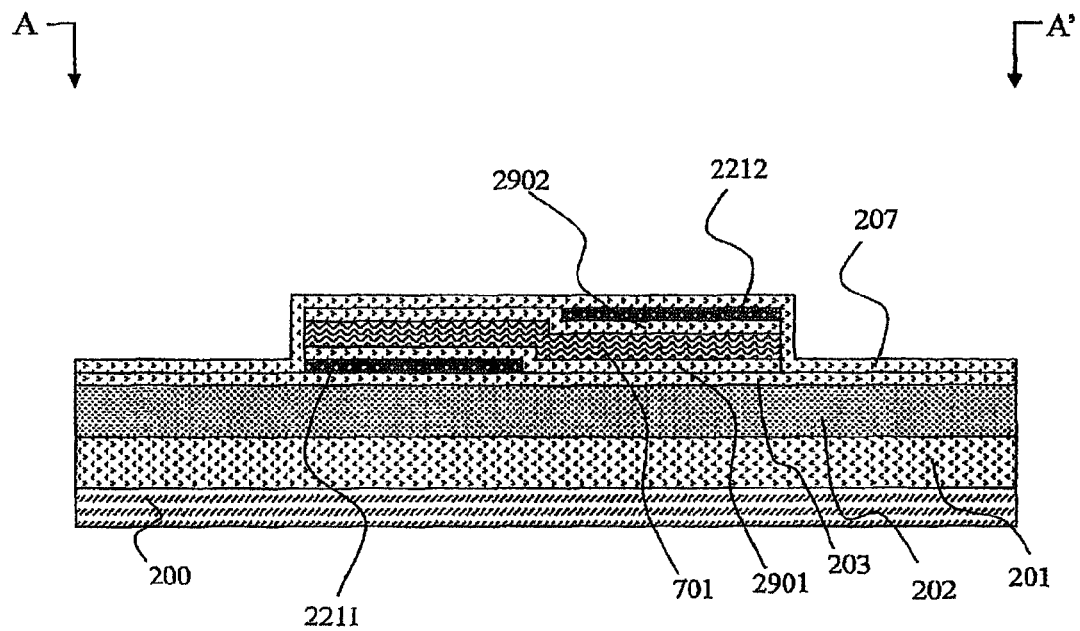
FIGS. 39, (a) and (b) are sectional views for explaining a manufacturing step of the ultrasonic transducer following the step shown in FIGS. 38, (a) and (b).
Figure 39:
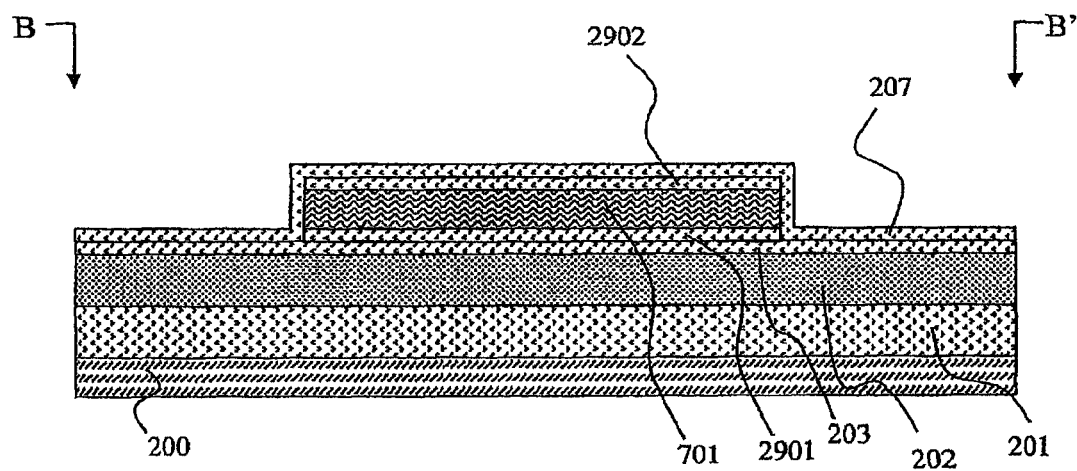

Then, patterning is performed for the insulating films 2901 and 2902, the aluminum alloy films 2211 and 2212, and the polycrystalline silicon film 701 by the photolithography and dry etching techniques to form a sacrificial layer consisting of the conductive films 2211 and 2212 and the polycrystalline silicon film 701 on the insulating film 203 (FIGS. 38, (a) and (b)). The hollow part is formed at the position of the sacrificial layer in a subsequent step. Finally, the insulating film 207 consisting of a silicon oxide film is deposited in 50 nm thickness by the plasma-CVD method (FIGS. 39, (a) and (b)). The following steps are the same steps as those shown in FIGS. 8 to 14 explained for the embodiment 1 to produce the CMUT cell of the second example according to the embodiment 3 shown in FIG. 29.

The characteristics of the embodiment 3 will be further explained in more detail. The effect of the disposition of the conductive films 2211 and 2212 so that both of them overlap with the region 301 in which the surface 205 below the hollow part and the surface 206 above the hollow part contact with each other as seen from above when the CMUT cell is driven is as explained with reference to FIG. 21, (b). Another characteristic effect of the disposition, i.e., such disposition of the conductive film 2211 disposed on the side of the surface 205 below the hollow part 204 and the conductive film 2212 disposed on the side of the surface 206 above the hollow part 204 that they do not overlap with each other in the contact region 301 as seen from above, will be explained below. If the conductive films 2211 and 2212 are disposed so that they overlap with each other in the area of the contact region 301 as seen from above, and the conductive films are not covered with an insulating film, the conductive films 2211 and 2212 directly contact with each other. When the conductive films 2211 and 2212 contact with each other, they have the same potential, and there arises a problem that they are adsorbed by each other due to electrostatic attraction between the electrical charges induced in the conductive films, and cannot be separated.

Further, even if the conductive films are covered with insulating films, the conductive films contact with each other through only the insulating films, and therefore there arises a problem that the conductive films are adsorbed by each other through the insulating films due to strong electrostatic attraction. Therefore, such a disposition as mentioned above is intentionally employed to suppress the mutual adsorption of the conductive films.

That is, in the case of the example in which the conductive films are exposed to the hollow part, since the conductive films are disposed so that they do not overlap with each other as seen from above, even if the surfaces above and below the hollow part contact with each other, the conductive films 2211 and 2212 do not contact with each other, and therefore the aforementioned problem of the adsorption can be avoided. Further, in the case of the example in which the conductive films are exposed to the hollow part through insulating films, that is, the conductive films are embedded in insulating films, if the conductive films do not overlap with each other as seen from above, the aforementioned problem of the adsorption can be avoided. In a more preferred example, the conductive films and the insulating films 2901 and 2902 covering them are formed so that a hollow part is provided between the insulating films 2901 and 2902 in the contact region 301, when the surfaces above and below the hollow part contact with each other. This is because such disposition can further reduce the electrostatic attraction between the conductive films, and suppress the adsorption by the electrostatic attraction.

In addition, in the case of the example in which the conductive films are exposed to the hollow part, the effect that electrical charge does not easily accumulate can of course be further obtained like the embodiment 1. Further, a structure in which electrical charge is more easily accumulated is provided by the insulating films 2901 and 2902 compared with a case where these insulating films are not provided, but even if the surfaces above and below the hollow part contact with each other, the conductive film 2212 exerts an electric field attenuating function for the insulating film 207 with respect to the conductive film 2211, and the conductive film 2211 exerts an electric field attenuating function for the insulating film 203 with respect to the conductive film 2212, as described above. Therefore, concentration of the leak electric currents in the insulating films 203 and 207 in the contact region 301 can be suppressed, and accumulation of electrical charge in the insulating films 203 and 207 and degradation of dielectric strength thereof can be suppressed.

Figure 40:
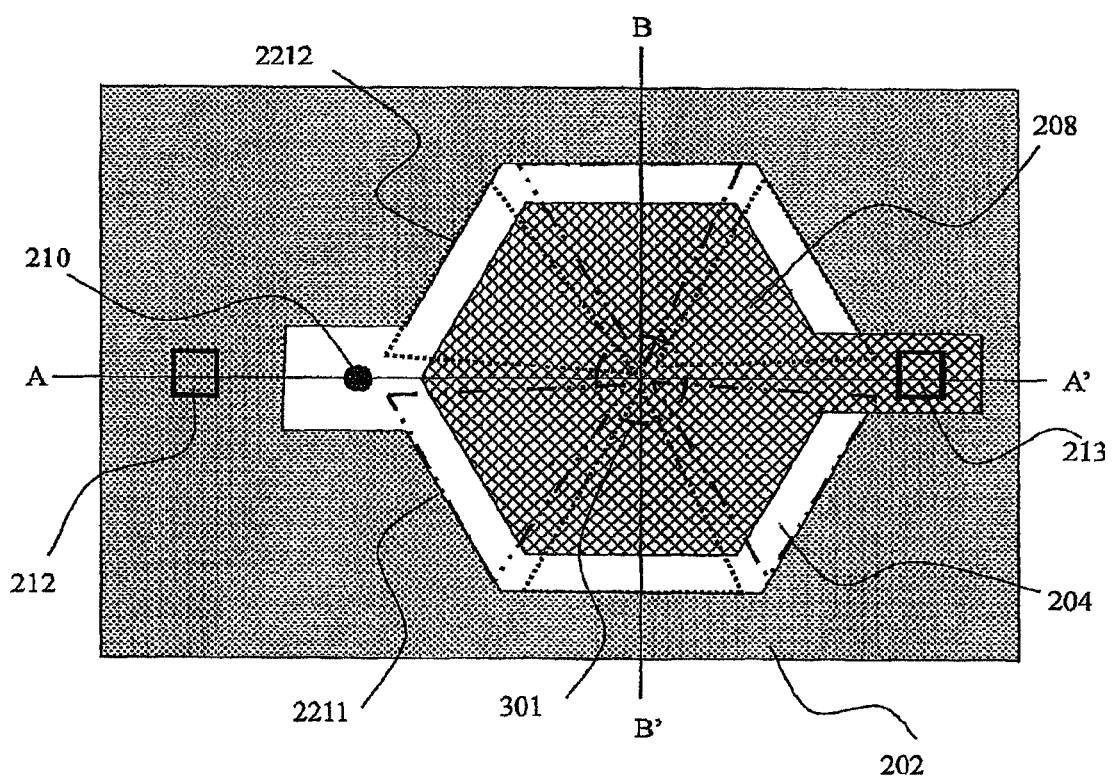
FIG. 40 is a top view of an ultrasonic transducer according to the third example of the embodiment 3.
Figure 41:
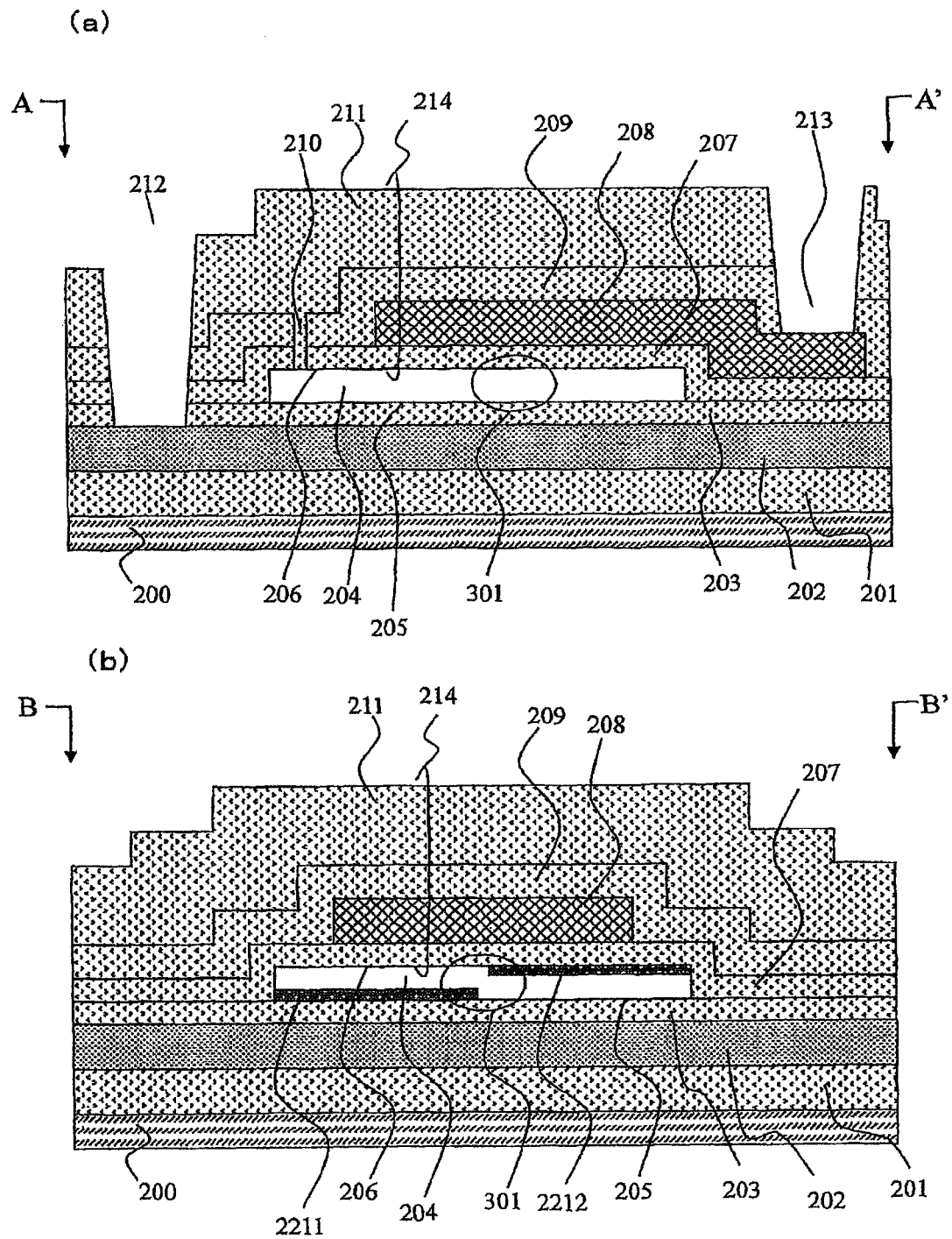
FIG. 41, (a) is a sectional view of the ultrasonic transducer shown in FIG. 40 along the line A-A' drawn in FIG. 40, and (b) is a sectional view of the ultrasonic transducer along the line B-B' drawn in FIG. 40.

In addition, although the CMUT cell according to the embodiment 3 shown FIG. 19 has a rectangular shape as the planar shape, it may have another shape. FIGS. 40 and 41 are a top view and a sectional view of an example where the cell has a hexagonal shape (third example). Also in this case, the conductive film 2211 exposed to the hollow part from the side of the surface below the hollow part 204 and the conductive film 2212 exposed to the hollow part from the side of the surface above the hollow part 204 are disposed so that they do not overlap with each other as seen from above, and both the conductive films 2211 and 2212 overlap with the region 301 where the surfaces below and above the hollow part contact with each other as seen from above, when the CMUT cell is driven. Therefore, concentration of the leak electric currents in the contact region 301 can be suppressed, and accumulation of electrical charge in the insulating films 203 and 207, and degradation of dielectric strength thereof can be suppressed.

Figure 42:
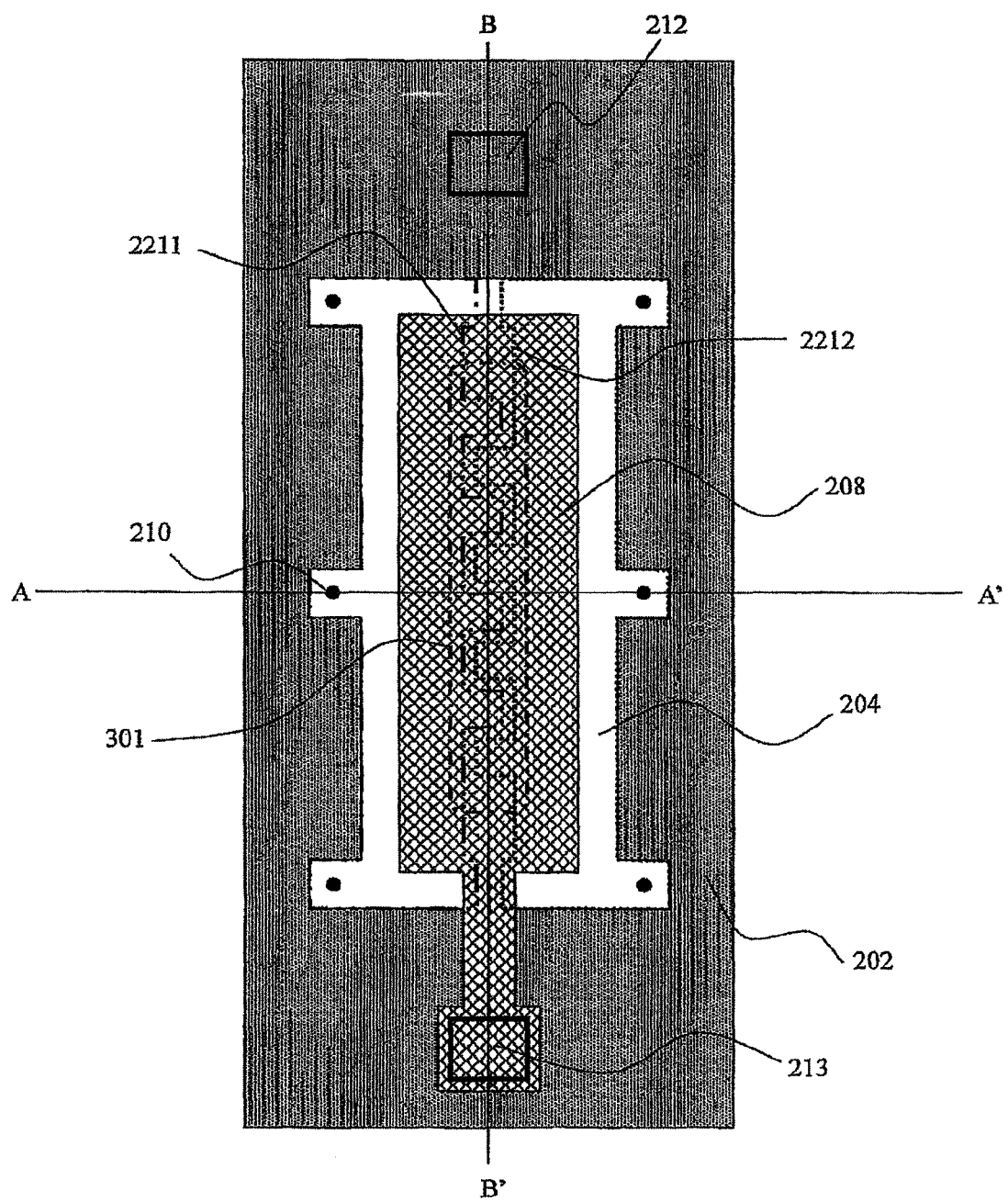
FIG. 42 is a top view of an ultrasonic transducer according to the fourth example of the embodiment 3.
Figure 43:
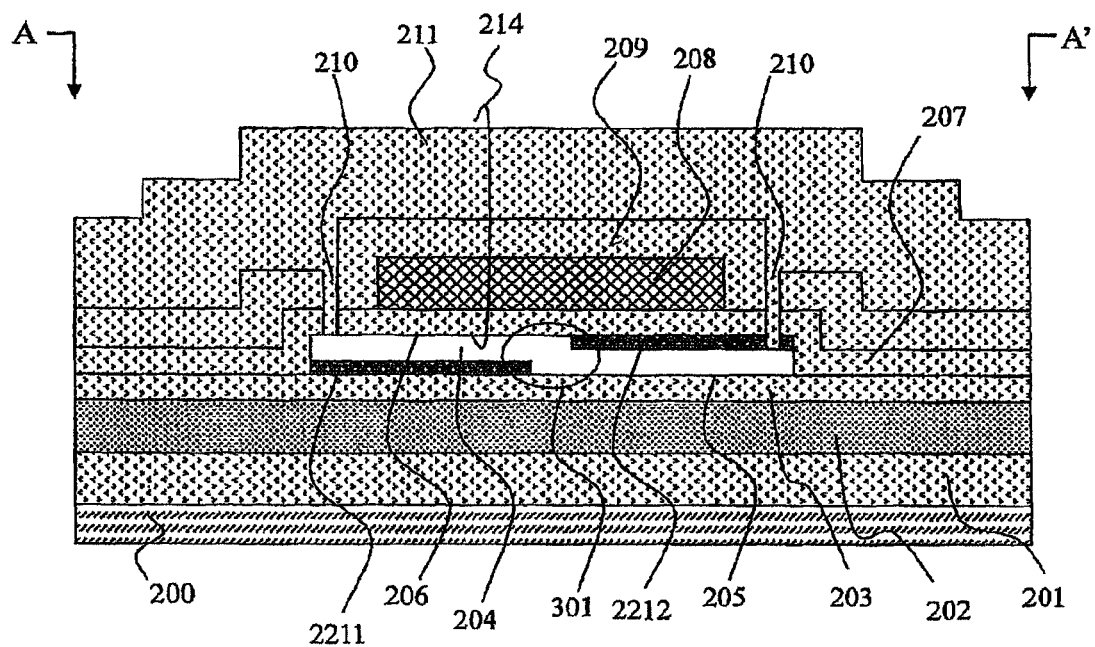
FIG. 43, (a) is a sectional view of the ultrasonic transducer shown in FIG. 42 along the line A-A' drawn in FIG. 42, and (b) is a sectional view of the ultrasonic transducer along the line B-B' drawn in FIG. 42.
Figure 43:
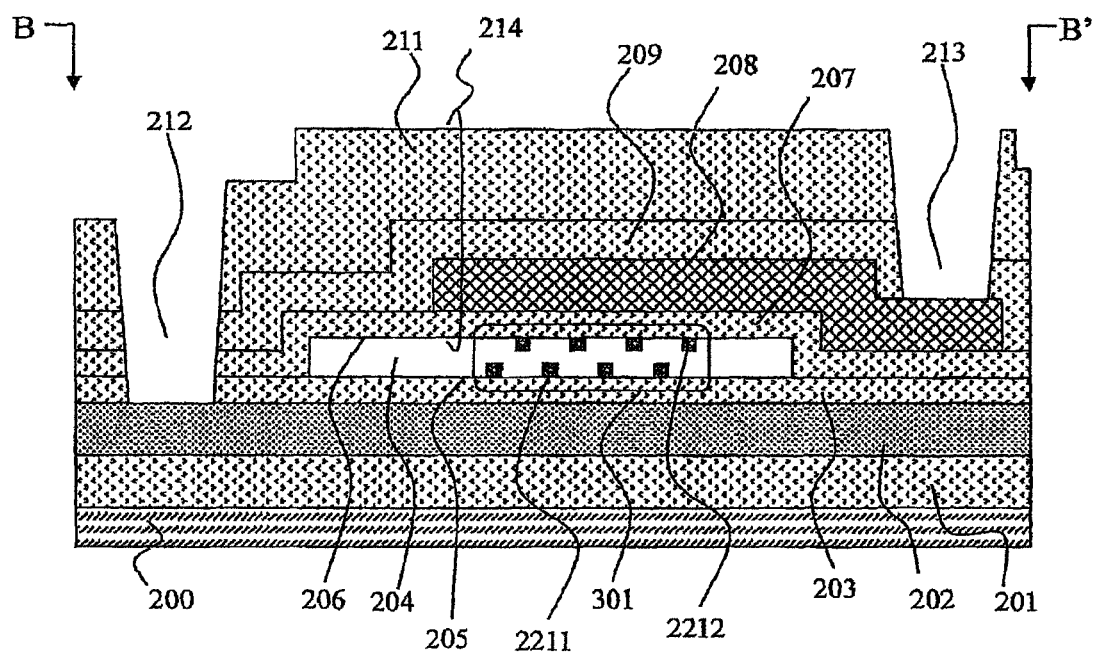

Further, although shapes of the conductive films 2211 and 2212 shown in FIG. 19 are symmetric with respect to the line B-B' as seen from above, they may be unsymmetrical as shown in FIG. 42 (fourth example). If the conductive films 2211 and 2212 are disposed so that the both overlap with the contact region 301 as seen from above, the same effect can be obtained. FIG. 43, (b) is a sectional view along the line B-B' drawn in FIG. 42. In the example shown in FIGS. 40 to 43, the conductive films may contact with the hollow part through insulating films like the relation between the configurations of FIGS. 20 and 29. Moreover, although the end of the conductive film is located at the same position as the end of the hollow part in all the drawings, the structure is not limited to such an example in which the conductive film reaches the end of the hollow part. Furthermore, only one of the conductive films may be exposed to the hollow part, but the other conductive film may contact with the hollow part through an insulating film. In addition, materials constituting the CMUT cell are similar to those explained for the embodiment 1, and similarly to the embodiment 1, the lower electrode may be a semiconductor substrate. Therefore, detailed explanations are omitted.

Embodiment 4

Figure 44:
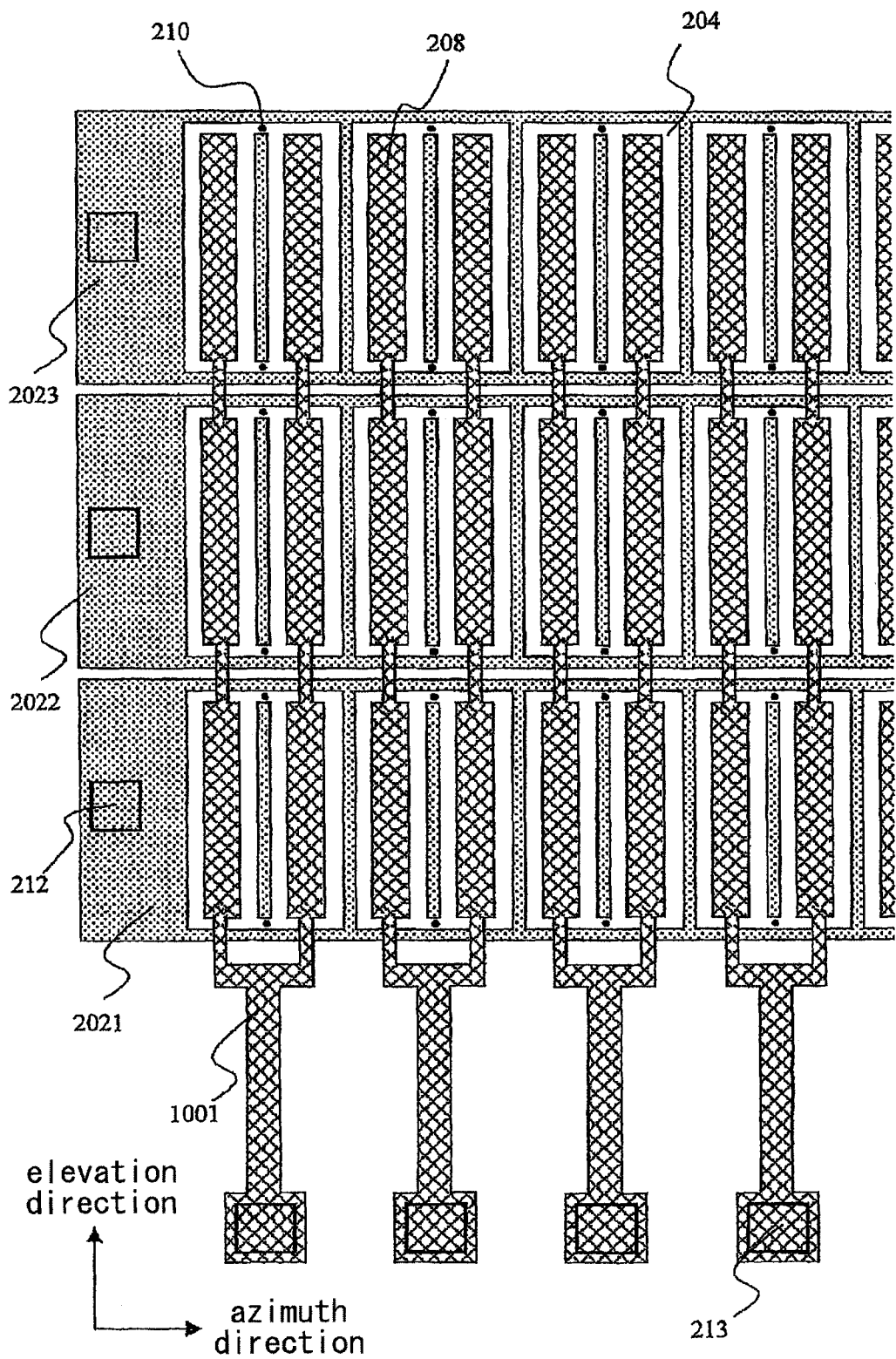
FIG. 44 is a top view of a chip on which the ultrasonic transducers according to the embodiment 4 are disposed in an array.

In the embodiments 1 to 3 mentioned above, single CMUT cells have been explained. However, as the embodiment 4, a chip on which the CMUT cells are integrated and arranged in an array will be explained. FIG. 44 shows a part of a chip comprising rectangular CMUT cells of the embodiment 3 arranged in an array. It comprises the lower electrodes 2021, 2022 and 2023, the hollow parts 204 formed above the lower electrodes, the upper electrodes 208 formed above the hollow parts 204, and so forth. The etching holes 211 for forming the hollow parts are communicated with the spaces serving as the hollow parts 204. The openings 212 are provided so as to reach the lower electrodes 2021, 2022 and 2023, and the openings 213 are provided so as to reach the upper electrodes 208. As explained for FIGS. 19 and 20, the conductive films 2211 are disposed so as to be exposed to the hollow parts, the conductive films 2212 are disposed so as to be exposed to the hollow parts, but they are not shown in the drawing. Between the upper electrodes 208 and the hollow parts 204, the insulating films 207 consisting of silicon oxide films are formed so as to cover the hollow parts 204, the conductive films 2212 and the lower electrodes 202, and between the lower electrodes 202, and the hollow parts 204 and the conductive films 2211, the insulating films 203 consisting of silicon oxide films are formed so as to cover the lower electrodes. However, these insulating films are not shown in the drawing, in order to show the lower electrodes 202 and the hollow parts 204. The layer structure of a section of each CMUT cell shown in FIG. 44 is the same as that shown in FIG. 20.

The disposition directions of the upper electrodes and the lower electrodes are perpendicular to each other, two CMUT cells are disposed at one intersection, and the upper electrodes of them are connected with wirings 1001. In FIG. 44, there is shown a part of the array, which comprises the upper electrodes for four channels in the azimuth direction and the lower electrodes for three channels in the elevation direction. As for a probe used for an ultrasonic diagnostic device, in the case of a general linear probe, for example, upper electrodes for 192 channels are disposed.

In the case of a probe having such a plurality of lower electrodes disposed in the elevation direction as shown in FIG. 44, form and intensity of ultrasonic beam transmitted and received at each intersection of the upper electrode and the lower electrode can be controlled by changing the voltage applied to each lower electrode, and thereby improvement in image quality of diagnostic images can be expected. Although difference of the voltage applied to the upper and lower electrodes changes according to the voltage applied to each lower electrode, since electric potential of the conductive film is determined by difference of potential between those of the upper electrode and lower electrode applied in each CMUT cell, the effect of suppressing accumulation of electrical charge in an insulating film and degradation of dielectric strength thereof obtained by the disposition of the conductive films in each single CMUT cell is also effective for the case in which the CMUT cells are arranged in an array and used as an ultrasonic probe.

The shapes of the conductive films 2211 and 2212 as seen from above may be a shape that includes the region 301 where the surface 206 above the hollow part and the surface 205 below the hollow part contact with each other. They may not have the same size as that of the hollow part 204, but a size included in the area of the hollow part, as seen from above. The size may be appropriately chosen so that concentration of electric fields in the insulating film can be reduced. Further, the sizes of the conductive films 2211 and 2212 may be larger than that of the hollow part 204 as seen from above. In this case, concentration of the electric currents in the insulating film in the contact region 301 can be further reduced by the larger conductive films 2211 and 2212.

Although the CMUT cells shown in FIGS. 19, 40, and 42 have a rectangular shape or a hexagonal shape as the planar shape, the shape is not limited to these, and the CMUT cell may have, for example, a circular shape or a polygonal shape. In addition, materials constituting the CMUT cell are similar to those explained for the embodiment 1, and similarly to the embodiment 1, the lower electrode may be a semiconductor substrate. Therefore, detailed explanations are omitted.

Embodiment 5

As the embodiments 1 to 4, CMUT cells constituting an ultrasonic transducer and a cell array have been explained. As the embodiment 5, an example relating to driving of CMUT cell will be explained.

Figure 45:
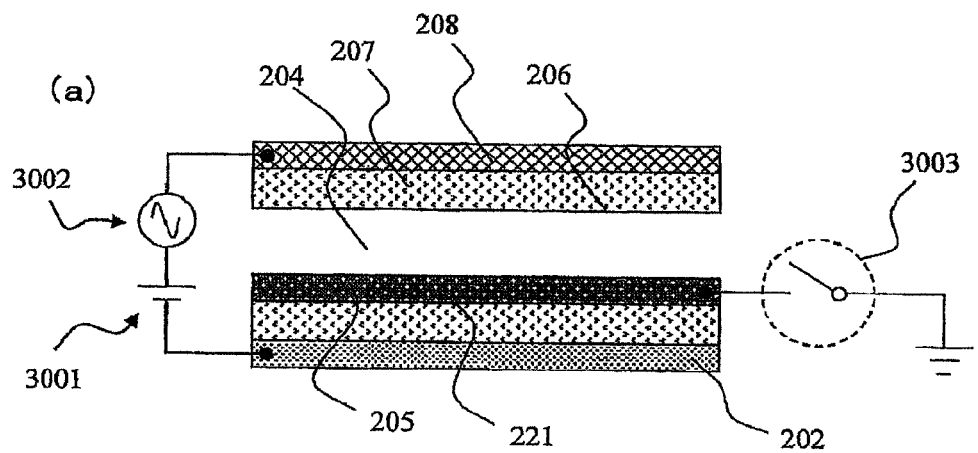
FIG. 45 is a schematic sectional view of an ultrasonic transducer according to the embodiment 5.

FIG. 45 is a schematic sectional view of the CMUT cell of the embodiment 1. The conductive film 221 is disposed on the lower electrode 202 through the insulating film 203 so as to be exposed to the hollow part. Further, the upper electrode is disposed above the hollow part 204 through the insulating film 207. A direct voltage 3001 and an alternating voltage 3002 are superimposingly applied to the lower electrode and the upper electrode, and a switch 3003 is connected to the conductive film 221 to provide a configuration that the conductive film 221 can be grounded via the switch 3003.

At the time of driving the CMUT cell, if the surface 206 above the hollow part contacts with the surface 205 below the hollow part, and the conductive film is charged with weak leak electric currents flowing in the insulating films 203 and 207, effectual potential difference between the upper and lower electrodes may be changed. The embodiment 5 is characterized in that the state of the conductive film 221 is made to be switchable between a grounded state and a floating state by connection and disconnection with the switch 3003, so that electrical charge charged in the conductive film 221 can be discharged. Since the transducer of this embodiment is provided with such a switch with which electrical charge can be discharged from the conductive film, the effect of disposing the conductive film so as to be exposed to the hollow part as shown in FIG. 45 can be similarly obtained even when an insulating film is disposed between the conductive film and the hollow part, i.e., even when the conductive film is embedded in the insulating film.

Figure 46:
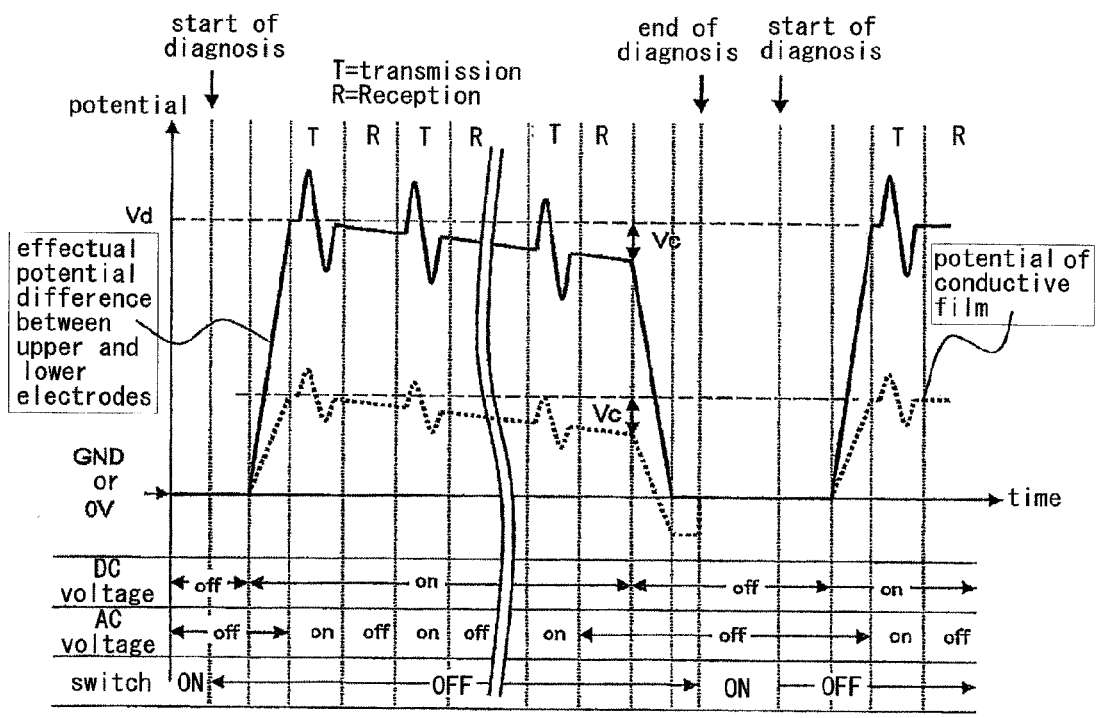
FIG. 46 is a graph showing effectual potential difference between the upper electrode and the lower electrode, electric potential of the conductive film, ON/OFF of direct voltage and alternating voltage, and switching of a switch(s) at the time of ultrasonic diagnosis using the ultrasonic transducer according to the embodiment 5.

The operation of the switch 3003 at the time of carrying out ultrasonic diagnosis with a probe using the ultrasonic transducer constituted with the CMUT cells according to this embodiment will be explained with reference to FIG. 46. FIG. 46 shows effectual potential difference between the upper electrode 208 and the lower electrode 202, electric potential of the conductive film 221, ON/OFF of the direct voltage 3001 and the alternating voltage 3002, and disconnection and connection (OFF/ON) of the switch 3003 at the time of ultrasonic diagnosis.

Before starting the diagnosis, the switch 3003 is made to be in the ON state to ground the conductive film 221. At the time of starting the diagnosis, the state of the switch 3003 is changed to the OFF state from the ON state to make the conductive film 221 in a floating state, i.e., a state that it is electrically isolated, and the diagnosis is performed. Degradation of the insulating films 203 and 207 can be thereby suppressed as explained for the embodiments 1, 2 and 3. If the conductive film 221 is gradually charged during the diagnosis, and charged for a potential of Vc at the end of the diagnosis, the effectual potential difference Vd between the upper and lower electrodes set at the time of the start of the diagnosis in order to obtain transmission sound pressure of supersonic waves and reception sensitivity required for the diagnosis is lowered by Vc. If the switch 3003 is continuously maintained to be in the OFF state, i.e., the conductive film 221 is in a state that it cannot be grounded, the conductive film 221 is further charged at the time of the next diagnosis, thus the effectual potential difference is further reduced from that reduced by Vc, and transmission sound pressure of supersonic waves and reception sensitivity required for the diagnosis can no longer be obtained. However, since this embodiment employs a configuration that the conductive film 221 can be grounded via the switch 3003, the switch 3003 can be made to be in the ON state at the end of the diagnosis to ground the conductive film 221, and thereby the charged electrical charge can be discharged. Therefore, the effectual potential difference between the upper and lower electrodes can be returned to Vd at the time of the next diagnosis, and the transmission sound pressure of supersonic waves and reception sensitivity required for the diagnosis can be obtained.

The timing for turning on or off the switch 3003 may be determined according to the electrification amount Vc of the conductive film. Although the state of the switch is changed in a period between one diagnosis and a subsequent diagnosis in the example shown in FIG. 46, the switch may be turned on or off when it becomes impossible to obtain the transmission sound pressure of supersonic waves and reception sensitivity required for the diagnosis due to reduction by Vc. Therefore, it may be changed in a shorter cycle, for example, between transmission and reception or between sets of transmission and reception, or it may be changed in a longer cycle, for example, once a day.

Further, although this embodiment was explained with reference to the CMUT cell in which the conductive film 221 is disposed so as to be exposed to the hollow part mentioned for the embodiment 1, the same effect can also be obtained for the CMUT cells or array mentioned as the embodiments 2, 3 and 4 by providing the configuration that the conductive film can be grounded via a switch. When there are two conductive films as in, for example, the embodiments 3 and 4, a switch for controlling grounding and no grounding may be connected to each of the both conductive films, or only one of them.

Embodiment 6

Figure 47:
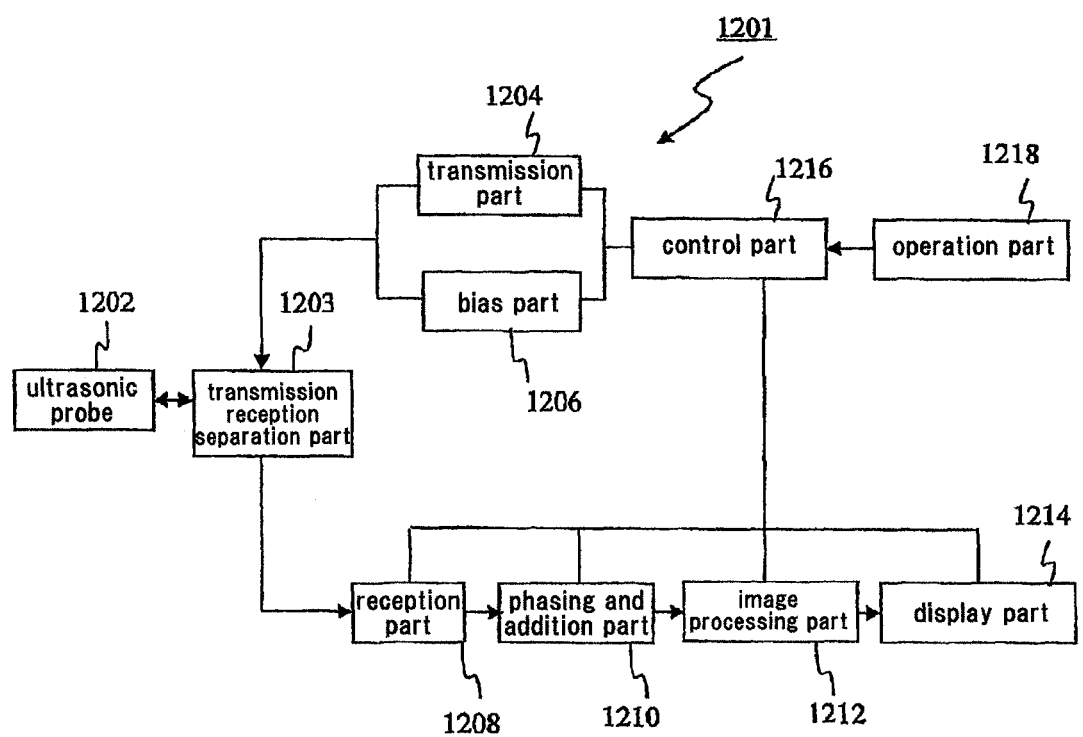
FIG. 47 is a configurational diagram of an ultrasonic diagnostic device according to the embodiment 6.

Finally, configuration and role of an ultrasonic diagnostic device provided with the ultrasonic transducer of the present invention will be explained with reference to FIG. 47. The ultrasonic diagnostic device 1201 comprises an ultrasonic probe 1202, a transmission and reception separation part 1203, a transmission part 1204, a bias part 1206, a reception part 1208, a phasing and addition part 1210, an image processing part 1212, a display part 1214, a control part 1216, and an operation part 1218.

The ultrasonic probe 1202 is a device for transmitting and receiving ultrasonic waves to and from a subject, which is used by being contacted with the subject. Ultrasonic waves are transmitted to the subject from the ultrasonic probe 1202, and reflected echo signals emitted from the subject are received by the ultrasonic probe 1202. The ultrasonic transducer according to any one of the embodiments 1 to 5 is disposed inside the ultrasonic probe 1202 and electrically connected with the transmission and reception separation part 1203 explained later. The transmission part 1204 and the bias part 1206 are devices for supplying driving signals to the ultrasonic probe 1202. The reception part 1208 is a device for receiving the reflected echo signals outputted from the ultrasonic probe 1202. The reception part 1208 further performs processings such. as analog-to-digital conversion for the received reflected echo signals. The transmission and reception separation part 1203 is for switching and separating transmission and reception, so that the driving signals are passed from the transmission part 1204 to the ultrasonic probe 1202 at the time of transmission, and received signals are passed from the ultrasonic probe 1202 to the reception part 1208 at the time of reception. The phasing and addition part 1210 is a device for performing phasing and addition of the received reflected echo signals. The image processing part 1212 is a device for constituting a diagnosis image (for example, tomographic images and angiographic images) on the basis of the reflected echo signals subjected to the phasing and addition. The display part 1214 is a display device for displaying a diagnostic image produced by image processing. The control part 1216 is a device for controlling the elements mentioned above. The control part 1216 has a role of controlling the ultrasonic probe 1202 as well as a roll of controlling ON/OFF of the switch for controlling grounding and no grounding of the conductive film of the embodiment 5. The operation part 1218 is a device for giving directions to the control part 1216. The operation part 1218 may be, for example, an inputting device such as trackball, keyboard and mouse.

INDUSTRIAL APPLICABILITY

The ultrasonic transducer and ultrasonic diagnostic device of the present invention can be widely used as medical diagnostic devices or diagnostic devices for structures.

DESCRIPTION OF NUMERICAL NOTATIONS

101, 202, 2021, 2022, 2023 Lower electrode
102, 204 Hollow part
200 Semiconductor substrate
103, 201, 203, 207, 209, 211, 2901, 2902 Insulating film
104, 208 Upper electrode
105, 214 Membrane
106, 206 Surface above hollow part
107, 205 Surface below hollow part
210 Etching hole
212 Opening reaching lower electrode
213 Opening reaching upper electrode
221, 2211, 2212 Conductive film
301 Region for contact of surface above hollow part and surface below hollow part
701, 7011, 7012, 7013 Sacrificial layer
1001 Wiring connecting upper electrodes
3001 Direct voltage
3002 Alternating voltage
3003 Switch connected to conductive film
3401 Pit
1201 Ultrasonic diagnostic device
1202 Ultrasonic probe
1203 Transmission and reception separation part
1204 Transmission part
1206 Bias part
1208 Reception part
1210 Phasing and addition part 1212 Image processing part
1214 Display part
1216 Control part
1218 Operation part

The invention claimed is:
1. An ultrasonic transducer, comprising:
a first electrode;
a first insulating film disposed on the first electrode;
a cavity provided above the first insulating film;
a second insulating film disposed above the cavity, wherein the cavity is disposed between the first and second insulating films;
a second electrode disposed on the second insulating film; and
an electrically isolated conductive film disposed between the first electrode and the second electrode, and wherein:
the conductive film is disposed at such a position that, a surface of the conductive film overlaps a surface of a region, wherein in the region, surfaces above and below the cavity are in contact with each other when the transducer is driven, and
the conductive film is in contact with the cavity.
2. The ultrasonic transducer according to claim 1, wherein:
the surface of the conductive film has a larger area than the surface of the region.
3. The ultrasonic transducer according to claim 1,
wherein the conductive film is disposed on a surface of the first insulating film; and
wherein a voltage lower than that applied to the second electrode is applied to the first electrode.
4. The ultrasonic transducer according to claim 1, wherein:
wherein the conductive film is disposed on a surface of the second insulating film; and
wherein a voltage higher than that applied to the second electrode is applied to the first electrode.
5. An ultrasonic diagnostic device, comprising:
an ultrasonic probe including the ultrasonic transducer according to claim 1; and
a controller configured to control the ultrasonic probe.
6. An ultrasonic transducer, comprising:
a first electrode;
a first insulating film disposed on the first electrode;
a cavity provided above the first insulating film;
a second insulating film disposed above the cavity, wherein the cavity is disposed between the first and second insulating films;
a second electrode disposed on the second insulating film;
a conductive film disposed between the first electrode and the second electrode, at such a position that, a surface of the conductive film overlaps a surface of a region;
wherein in the region, surfaces above and below the cavity are in contact with each other when the transducer is driven; and
a switch connected to the conductive film, configured to open and close a connection from the conductive film to a ground potential.
7. The ultrasonic transducer according to claim 6, wherein the conductive film is in contact with the cavity.
8. The ultrasonic transducer according to claim 6, wherein the conductive film is embedded in either one of the first insulating film and the second insulating film.
9. The ultrasonic transducer according to claim 6, wherein the surface of the conductive film has a larger area than the surface of the region.
10. The ultrasonic transducer according to claim 6, wherein the conductive film is disposed on a surface of the first insulating film; and
wherein a voltage lower than that applied to the second electrode is applied to the first electrode.
11. The ultrasonic transducer according to claim 6, wherein the conductive film is disposed on a surface of the second insulating film; and
wherein a voltage higher than that applied to the second electrode is applied to the first electrode.
12. An ultrasonic diagnostic device, comprising:
an ultrasonic probe including the ultrasonic transducer according to claim 6; and
a controller configured to control the ultrasonic probe.
13. An ultrasonic diagnostic device, comprising:
an ultrasonic probe including the ultrasonic transducer according to claim 6; and
a controller configured to, at the time of start of diagnosis, control the switch so as to disconnect the conductive film from the ground potential, thereby switching from a closed state in which the conductive film is connected to the ground potential, to an open state in which the conductive film is disconnected from the ground potential.
14. An ultrasonic transducer, comprising:
a first electrode;
a first insulating film disposed on the first electrode;
an electrically isolated first conductive film disposed on the first insulating film;
a cavity provided above the first conductive film;
an electrically isolated second conductive film disposed above the cavity;
a second insulating film disposed on the second conductive film, wherein the cavity is disposed between the first and second insulating films; and
a second electrode disposed on the second insulating film;
wherein the first conductive film and the second conductive film are disposed in a region, wherein in the region, surfaces above and below the cavity are in contact with each other when the transducer is driven; and
wherein the first conductive film and the second conductive film do not overlap with each other in that region.
15. The ultrasonic transducer according to claim 14, wherein the first and second conductive films are in contact with the cavity.
16. The ultrasonic transducer according to claim 14, wherein the first conductive film is embedded in the first insulating film; and
wherein the second conductive film is embedded in the second insulating film.
17. The ultrasonic transducer according to claim 14, further comprising:
a first switch connected to the first conductive film configured to connect and disconnect the first conductive film to the ground potential; and
a second switch connected to the second conductive film configured to connect and disconnect the second conductive film to the ground potential.
18. An ultrasonic diagnostic device, comprising:
an ultrasonic probe including the ultrasonic transducer according to claim 14; and
a controller configured to control the ultrasonic probe.
19. An ultrasonic diagnostic device, comprising:
an ultrasonic probe including the ultrasonic transducer according to claim 17; and
a controller configured to control the ultrasonic probe, the first switch and the second switch;
wherein the controller switches states of the first and second switches from connected states to disconnected states at the time of start of diagnosis.

* * * * *